(12) United States Patent
Ma et al.

(10) Patent No.: US 11,832,457 B2
(45) Date of Patent: Nov. 28, 2023

(54) NITROGEN-CONTAINING COMPOUND, AND ORGANIC ELECTROLUMINESCENT DEVICE AND ELECTRONIC APPARATUS THEREOF

(71) Applicant: Shaanxi Lighte Optoelectronics Material Co., Ltd., Xi'an (CN)

(72) Inventors: Tiantian Ma, Xi'an (CN); Min Yang, Xi'an (CN); Kongyan Zhang, Xi'an (CN); Lei Yang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/028,900

(22) PCT Filed: Feb. 11, 2022

(86) PCT No.: PCT/CN2022/076099
§ 371 (c)(1),
(2) Date: Mar. 28, 2023

(87) PCT Pub. No.: WO2023/005191
PCT Pub. Date: Feb. 2, 2023

(65) Prior Publication Data
US 2023/0337534 A1 Oct. 19, 2023

(30) Foreign Application Priority Data

Jul. 30, 2021 (CN) .......................... 202110868392.3
Nov. 23, 2021 (CN) .......................... 202111394660.9

(51) Int. Cl.
C07D 487/04 (2006.01)
H01L 51/00 (2006.01)
(Continued)

(52) U.S. Cl.
CPC ....... *H10K 85/6572* (2023.02); *C07D 487/04* (2013.01); *H10K 85/654* (2023.02); *C07B 2200/05* (2013.01); *H10K 50/11* (2023.02)

(58) Field of Classification Search
CPC .......................... C07D 487/04; C07B 2200/05
See application file for complete search history.

(56) References Cited

U.S. PATENT DOCUMENTS

| 11,588,116 B2* | 2/2023 | Suh ........ C07D 209/86 |
| 2022/0006022 A1* | 1/2022 | Suh ........ H10K 85/6576 |
| 2022/0259208 A1* | 8/2022 | Suh ........ H10K 85/6572 |

FOREIGN PATENT DOCUMENTS

| CN | 103204846 A | 7/2013 |
| KR | 20160069934 A | 6/2016 |

(Continued)

OTHER PUBLICATIONS

Songpo Xiang et al., "To improve the efficiency of thermally activated delayed fluorescence OLEDs by controlling the horizontal orientation through optimizing stereoscopic and linear structures of indolocarbazole isomers," Journal of Materials Chemistry C, 6, 5812-5810, dated 2018, 9 pages.

(Continued)

*Primary Examiner* — Vu A Nguyen
(74) *Attorney, Agent, or Firm* — TUCKER ELLIS LLP

(57) ABSTRACT

The present disclosure provides a nitrogen-containing compound, and an organic electroluminescent device and an electronic device including the same, and belongs to the field of organic electroluminescence. A transport group in the nitrogen-containing compound of the present disclosure has an overlapping spatial positional relationship, which can improve the carrier transport properties, and when the mate- (Continued)

rial is applied to an organic electroluminescent device, the performance of the organic electroluminescent device can be significantly improved.

7 Claims, 1 Drawing Sheet

(51) Int. Cl.
*H01L 51/50* (2006.01)
*H10K 85/60* (2023.01)
*H10K 50/11* (2023.01)

(56) References Cited

FOREIGN PATENT DOCUMENTS

| KR | 2054806 B1 | * | 12/2019 | ........... C07D 487/04 |
| KR | 2193015 B1 | * | 12/2020 | ........... C07D 209/86 |
| WO | 2021125649 A1 | | 6/2021 | |
| WO | WO-2021125649 A1 | * | 6/2021 | ........... C07D 487/04 |

OTHER PUBLICATIONS

Yong-Chen Ning, "Structural Identification of Organic Compounds with Spectroscopic Techniques," dated 2005, 8 pages including translation.

International Search Report from corresponding International Patent Application No. PCT/CN2022/076099, dated Mar. 22, 2022, 4 pages including translation.

* cited by examiner

NITROGEN-CONTAINING COMPOUND, AND ORGANIC ELECTROLUMINESCENT DEVICE AND ELECTRONIC APPARATUS THEREOF

CROSS REFERENCE TO RELATED APPLICATIONS

This application claims the priority of Chinese patent application No. CN202110868392.3, filed on Jul. 30, 2021, and Chinese patent application No. CN202111394660.9, filed on Nov. 23, 2021, the contents of which are incorporated herein by reference in their entirety as a part of this disclosure.

FIELD

The present disclosure relates to the technical field of organic electroluminescence, in particular to a nitrogen-containing compound, and an organic electroluminescent device and an electronic apparatus thereof.

BACKGROUND

Organic electroluminescent materials (OLED) have the advantages of ultra-thinness, self-illumination, wide viewing angle, fast response, high luminous efficiency, good temperature adaptability, simple production process, low driving voltage, low energy consumption, and the like as a new-generation display technology, and have been widely used in industries such as flat panel display, flexible display, solid state lighting, and vehicle display.

Currently, in terms of organic electroluminescent devices, a phosphorescent organic electroluminescent device is a main development direction, and is mainly used in display devices such as mobile phones, vehicles, and the like. However, with respect to the organic electroluminescent devices, problems such as reduced luminous efficiency and shortened service life still exist, resulting in decreased device performance. Thus, these problems of efficiency or service life must be solved for phosphorescent host materials, and there is a constant need to develop new materials for organic electroluminescence devices which are highly efficient, long in service life and suitable for mass production.

SUMMARY

The present disclosure provides a nitrogen-containing compound, and an organic electroluminescent device and an electronic apparatus thereof to solve the problems of low luminous efficiency and shortened service life existing in the prior art.

In order to achieve the above object, the present disclosure employs the following technical solutions:

according to a first aspect of the present disclosure, provided is a nitrogen-containing compound, having a structure as shown in a formula 1:

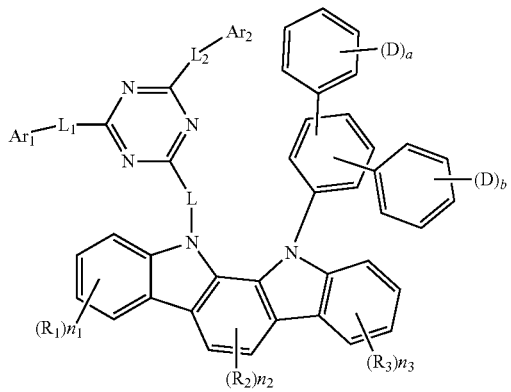

Formula 1 wherein L, $L_1$ and $L_2$ are each independently selected from a single bond and substituted or unsubstituted arylene with 6 to 30 carbon atoms;
$Ar_1$ and $Ar_2$ are each independently selected from substituted or unsubstituted aryl with 6 to 30 carbon atoms;
a and b are each independently selected from 0, 1, 2, 3, 4 or 5, and a+b≥1;
substituents in the L, the $L_1$, the $L_2$, the $Ar_1$ and the $Ar_2$ are each independently selected from a halogen group, cyano, aryl with 6 to 12 carbon atoms, trialkylsilyl with 3 to 12 carbon atoms, triphenylsilyl, alkyl with 1 to 10 carbon atoms, haloalkyl with 1 to 10 carbon atoms, cycloalkyl with 3 to 10 carbon atoms, heterocycloalkyl with 2 to 10 carbon atoms or alkoxy with 1 to 10 carbon atoms;
optionally, in $Ar_1$ and $Ar_2$, any two adjacent substituents form a ring;
each $R_1$, each $R_2$, and each $R_3$ are each independently selected from hydrogen, deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms, or cycloalkyl with 3 to 10 carbon atoms;
$n_1$ represents the number of $R_1$, $n_1$ is selected from 1, 2 or 3, and when $n_1$ is greater than 1, any two $R_1$ are the same or different;
$n_2$ represents the number of $R_2$, $n_2$ is selected from 1 or 2, and when $n_2$ is greater than 1, any two $R_2$ are the same or different; and
$n_3$ represents the number of $R_3$, $n_3$ is selected from 1, 2, 3 or 4, and when $n_3$ is greater than 1, any two $R_3$ are the same or different.

The nitrogen-containing compound of the present disclosure has an indolocarbazolyl in a specific fusing mode, which combines diaryl-substituted triazinyl with a deuterated diphenyl-substituted phenyl. Aryl on the triazinyl in this molecular structure does not contain a deuterium atom, and diaryltriazinyl and the diphenylbenzenyl have an overlapping spatial positional relationship and spatial conjugation characteristics, such that the material has an enhanced electron transport ability. And deuteration of phenyl in the periphery of diphenylbenzenyl can reduce the size of diphenyl-substituted phenyl, resulting in a more compact spatial overlap with the triazinyl and further enhancing the electron transport characteristics. The nitrogen-containing compound is used as a host material for a luminescent layer of a phosphorescent organic electroluminescent device, so that the luminescent layer has good electron transport characteristics, the charge balance and exciton recombination efficiency are promoted, the device has a lower voltage, and the luminous efficiency and service life characteristics of the device are improved.

A second aspect of the present disclosure provides an organic electroluminescent device, including an anode and a cathode which are oppositely disposed, and a functional layer disposed between the anode and the cathode; where the functional layer includes the nitrogen-containing compound according to the first aspect.

A third aspect of the present disclosure provides an electronic apparatus, including the organic electroluminescent device according to the second aspect.

BRIEF DESCRIPTION OF THE DRAWINGS

The drawings here are incorporated into and constitute part of the description, illustrating the examples conforming to the present disclosure, and used together with the description to interpret the principles of the present disclosure.

Figure 1:
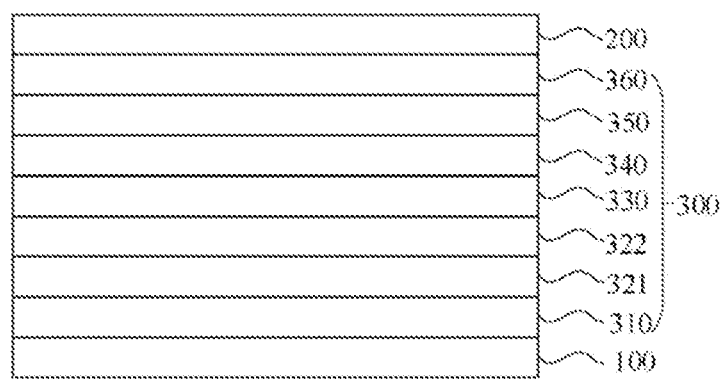
FIG. 1 is a structural schematic diagram of an organic electroluminescent device according to one embodiment of the present disclosure.

DESCRIPTION OF REFERENCE SIGNS 100, anode; 200, cathode; 300, functional layer; 310, hole injection layer; 321, hole transport layer; 322, hole auxiliary layer; 330, organic luminescent layer; 340, hole blocking layer; 350, electron transport layer; 360, electron injection layer; and 400, electronic device.

DETAILED DESCRIPTION

Embodiments will now be described more fully with reference to the accompanying drawings. However, the embodiments can be implemented in a variety of forms, and should not be understood as a limitation to the instances set forth here; and on the contrary, these embodiments are provided such that the present disclosure will be more comprehensive and complete, and the concepts of the embodiments are comprehensively conveyed to those skilled in the art. The described features, structures, or characteristics may be incorporated in one or more embodiments in any suitable manner. In the following description, many specific details are provided to give a sufficient understanding of the embodiments of the present disclosure.

The described features, structures, or characteristics may be incorporated in one or more embodiments in any suitable manner. In the following description, many specific details are provided to give a sufficient understanding of the embodiments of the present disclosure. However, those skilled in the art will realize that the technical solution of the present disclosure may be practiced without one or more of the specific details, or other methods, components, materials, etc. may be employed. In other cases, well-known structures, materials, or operations are not shown or described in detail to avoid obscuring the primary technical ideas of the present disclosure.

The present disclosure provides a nitrogen-containing compound, having a structure as shown in a formula 1:

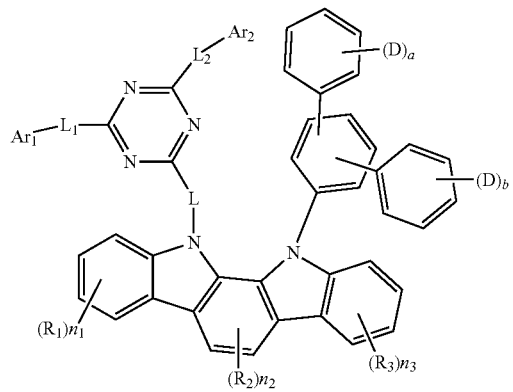

Formula 1 where L, $L_1$ and $L_2$ are each independently selected from a single bond and substituted or unsubstituted arylene with 6 to 30 carbon atoms;

$Ar_1$ and $Ar_2$ are each independently selected from substituted or unsubstituted aryl with 6 to 30 carbon atoms;

a and b are each independently selected from 0, 1, 2, 3, 4 or 5, and a+b≥1;

substituents in the L, the $L_1$, the $L_2$, the $Ar_1$ and the $Ar_2$ are each independently selected from a halogen group, cyano, aryl with 6 to 12 carbon atoms, trialkylsilyl with 3 to 12 carbon atoms, triphenylsilyl, alkyl with 1 to 10 carbon atoms, haloalkyl with 1 to 10 carbon atoms, cycloalkyl with 3 to 10 carbon atoms, heterocycloalkyl with 2 to 10 carbon atoms or alkoxy with 1 to 10 carbon atoms;

optionally, in $Ar_1$ and $Ar_2$, any two adjacent substituents form a ring;

each $R_1$, each $R_2$, and each $R_3$ are each independently selected from hydrogen, deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms, or cycloalkyl with 3 to 10 carbon atoms;

$n_1$ represents the number of $R_1$, $n_1$ is selected from 1, 2 or 3, and when $n_1$ is greater than 1, any two $R_1$ are the same or different;

$n_2$ represents the number of $R_2$, $n_2$ is selected from 1 or 2, and when $n_2$ is greater than 1, any two $R_2$ are the same or different; and $n_3$ represents the number of $R_3$, $n_3$ is selected from 1, 2, 3 or 4, and when $n_3$ is greater than 1, any two $R_3$ are the same or different.

In the formula 1, a and b represent the number of a deuterium (D) substituent on a benzene ring, and are each independently selected from 0, 1, 2, 3, 4, or 5, and 10≥a+b≥1.

In the present disclosure, the adopted description modes " . . . are each independently selected from", and " . . . are each independently selected from" can be interchanged, and should be understood in a broad sense, which means that in different groups, specific options expressed between the same symbols do not influence each other, or in a same group, specific options expressed between the same symbols do not influence each other. For example, the meaning of "

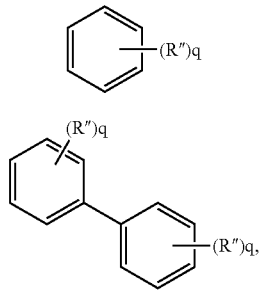

where each q is independently 0, 1, 2 or 3, and each R" is independently selected from hydrogen, deuterium, fluorine and chlorine" is as follows: a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as "substituted or unsubstituted" means that a functional group described behind the term may have or do not have a substituent (in the following, the substituent is collectively referred to as Rc in order to facilitate description). For example, the "substituted or unsubstituted aryl" refers to aryl having the substituent Rc or unsubstituted aryl. The above substituent, i.e., Rc, can be, for example, deuterium, a halogen group, cyano, aryl with 6 to 12 carbon atoms, trialkylsilyl with 3 to 12 carbon atoms, triphenylsilyl, alkyl with 1 to 10 carbon atoms, haloalkyl with 1 to 10 carbon atoms, cycloalkyl with 3 to 10 carbon atoms, heterocycloalkyl with 2 to 10 carbon atoms or alkoxy with 1 to 10 carbon atoms.

In the present disclosure, a "substituted" functional group can be substituted by one or two or more substituents of the above Rc; when two substituents Rc are connected to a same atom, the two substituents Rc may independently exist or may connect to each other to form a spirocyclic ring with the atom; and when substituent Rc is present on each of two adjacent carbon atoms in the functional group, two adjacent substituents Rc may independently exist or are fused with the functional group to which they are connected to form a ring.

In the present disclosure, the terms "optional" and "optionally" mean that the subsequently described event may occur but do not have to occur, and that the description includes instances where the event occurs or does not occur. For example, "optionally, two adjacent substituents form a ring", which means that the two substituents can, but do not have to, form a ring, including scenarios in which two adjacent substituents form a ring and scenarios in which two adjacent substituents do not form a ring.

In the present disclosure, "any two adjacent" in the condition that "any two adjacent substituents form a ring" can include the condition that a same atom has two substituents, and the condition that two adjacent atoms each have one substituent; when the same atom has two substituents, the two substituents may form a saturated or unsaturated spirocyclic ring with the atom to which they are jointly connected; and when two adjacent atoms each have one substituent, the two substituents may be fused to form a ring.

In the present disclosure, "optionally, in Ar$_1$ and Ar$_2$, any two adjacent substituents form a ring", which means that in Ar$_1$ or Ar$_2$, any two adjacent substituents may or may not form a ring. For example, when two adjacent substituents in Ar$_1$ form a ring, the number of carbon atoms in the ring may be 5 to 13, and the ring may be saturated or unsaturated; and the ring is, for example, cyclohexane, cyclopentane, adamantane, a benzene ring, a naphthalene ring, a fluorene ring or the like, but is not limited to this.

In the present disclosure, the number of carbon atoms in a substituted or unsubstituted functional group refers to the number of all carbon atoms. For example, if L is selected from substituted arylene with 12 carbon atoms, the number of all carbon atoms of the arylene and substituents on the arylene is 12. For example: if Ar$_1$ is

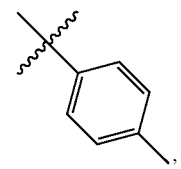 [SMILES: *c1ccc(C)cc1]

then the number of carbon atoms is 7; and if L is

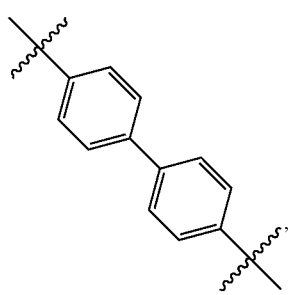 [SMILES: *c1ccc(-c2ccc(*)cc2)cc1]

the number of carbon atoms is 12.

In the present disclosure, the "alkyl" may include linear alkyl or branched alkyl. The alkyl may have 1 to 10 carbon atoms, and in the present disclosure, the range of values such as "1 to 10" refers to each integer in a given range; for example, "alkyl with 1 to 10 carbon atoms" refers to alkyl that may include 1, 2, 3, 4, 5, 6, 7, 8, 9 or 10 carbon atoms. In addition, the alkyl may be substituted or unsubstituted.

Optionally, the alkyl is alkyl with 1 to 5 carbon atoms, and specific examples include, but are not limited to, methyl, ethyl, propyl, isopropyl, n-butyl, isobutyl, sec-butyl, tert-butyl, and pentyl.

In the present disclosure, cycloalkyl refers to saturated hydrocarbon containing an alicyclic structure, including monocyclic and fused structures. The cycloalkyl can have 3 to 10 carbon atoms, and the range of values such as "3 to 10" refers to each integer in a given range; for example, "cycloalkyl with 3 to 10 carbon atoms" refers to cycloalkyl that may include 3, 4, 5, 6, 7, 8, 9, or 10 carbon atoms. The cycloalkyl may be substituted or unsubstituted. Examples of the cycloalkyl, such as cyclopentyl, cyclohexyl, and adamantyl.

In the present disclosure, aryl refers to an optional functional group or substituent derived from an aromatic carbocyclic ring. The aryl may be monocyclic aryl (e.g., phenyl)

or polycyclic aryl, in other words, the aryl can be monocyclic aryl, fused aryl, two or more monocyclic aryl conjugatedly connected through carbon-carbon bonds, monocyclic aryl and fused aryl which are conjugatedly connected through a carbon-carbon bond, or two or more fused aryl conjugatedly connected through carbon-carbon bonds. That is, unless otherwise noted, two or more aromatic groups conjugatedly connected through carbon-carbon bonds can also be regarded as the aryl of the present disclosure. The fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se, Si and the like. For example, in the present disclosure, biphenyl, terphenyl, etc. are aryl. Examples of the aryl can include, but are not limited to, phenyl, naphthyl, fluorenyl, anthryl, phenanthryl, biphenyl, terphenyl, quaterphenyl, triphenylene

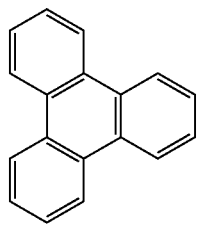 [SMILES: c1ccc2c(c1)c1ccccc1c1ccccc21]

pyrenyl, benzofluoranthenyl, chrysenyl, and the like.

In the present disclosure, terphenyl includes

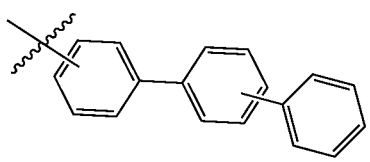

and

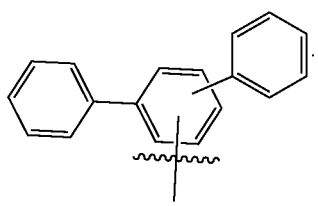

In the present disclosure, "substituted or unsubstituted aryl" can contain 6 to 30 carbon atoms. In some embodiments, the number of carbon atoms in the substituted or unsubstituted aryl is 6 to 25. In other embodiments, the number of carbon atoms in the substituted or unsubstituted aryl is 6 to 20. In other embodiments, the number of carbon atoms in the substituted or unsubstituted aryl is 6 to 18. And in still other embodiments, the number of carbon atoms in the substituted or unsubstituted aryl is 6 to 12.

In the present disclosure, the arylene involved is a divalent group formed by further loss of one hydrogen atom from aryl.

In the present disclosure, the substituted aryl can be that one or two or more hydrogen atoms in the aryl are substituted by groups such as a halogen group, cyano, aryl, heteroaryl, trialkylsilyl, alkyl, cycloalkyl, alkoxy, and the like. It should be understood that the number of carbon atoms in the substituted aryl refers to the total number of carbon atoms of the aryl and substituents on the aryl, for example, the substituted aryl with 18 carbon atoms means that the total number of carbon atoms of the aryl and its substituents is 18.

In the present disclosure, specific examples of aryl as a substituent include, but are not limited to, phenyl, naphthyl, anthryl, phenanthryl, dimethylfluorenyl, biphenyl, and the like.

In the present disclosure, heteroaryl refers to a monovalent aromatic ring or its derivative containing 1, 2, 3, 4, 5, or 6 heteroatoms in the ring, and the heteroatom may be at least one of B, O, N, P, Si, Se, and S. The heteroaryl may be monocyclic heteroaryl or polycyclic heteroaryl, in other words, the heteroaryl may be a single aromatic ring system or a plurality of aromatic ring systems conjugatedly connected through carbon-carbon bonds, and any aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited to these. The thienyl, furyl, phenanthrolinyl and the like are heteroaryl of the single aromatic ring system, and N-phenylcarbazolyl and N-pyridylcarbazolyl are heteroaryl of the polycyclic systems conjugatedly connected through carbon-carbon bonds.

In the present disclosure, the heteroarylene involved refers to a divalent group formed by further loss of one hydrogen atom from heteroaryl.

In the present disclosure, the substituted heteroaryl can be that one or two or more hydrogen atoms in the heteroaryl are substituted by groups such as a deuterium atom, a halogen group, cyano, aryl, heteroaryl, trialkylsilyl, alkyl, cycloalkyl, alkoxy and the like. It should be understood that the number of carbon atoms of the substituted heteroaryl refers to the total number of carbon atoms of heteroaryl and substituents on the heteroaryl.

In the present disclosure, specific examples of heteroaryl as a substituent include, but are not limited to, pyridyl, carbazolyl, dibenzofuranyl and dibenzothienyl.

In the present disclosure, the halogen group includes fluorine, iodine, bromine, chlorine, and the like.

In the present disclosure, specific examples of the trialkylsilyl with 3 to 12 carbon atoms include, but are not limited to, trimethylsilyl, triethylsilyl, and the like.

In the present disclosure, specific examples of the haloalkyl with 1 to 10 carbon atoms include, but are not limited to, trifluoromethyl.

In the present disclosure, an unpositioned connecting bond is a single bond "⁃⁃⁃" extending from a ring system, which means that one end of the connecting bond can be connected with any position in the ring system through which the bond penetrates, and the other end of the connecting bond is connected with the remaining part of a compound molecule.

For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10):

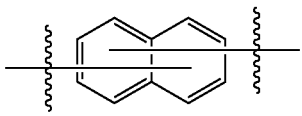
(f)

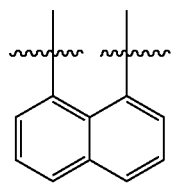
(f-1)

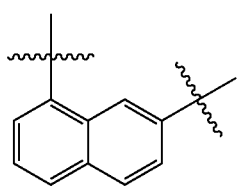
(f-2)

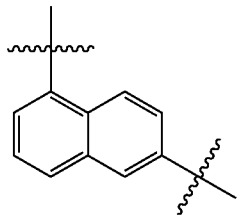
(f-3)

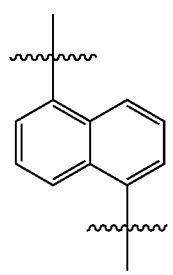
(f-4)

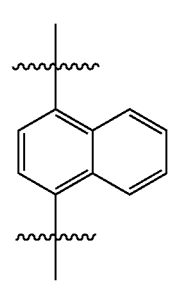
(f-5)

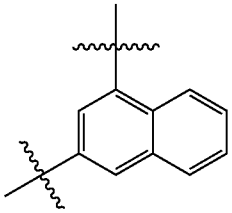
(f-6)

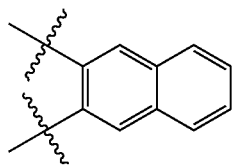
(f-7)

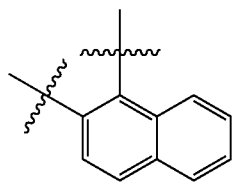
(f-8)

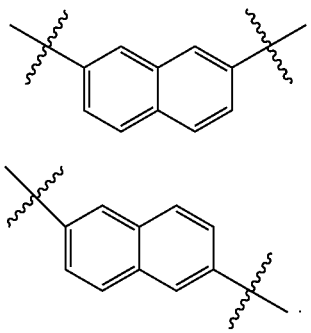
(f-9)

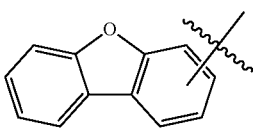
(f-10)

For example, as shown in the following formula (X'), dibenzofuranyl represented by the formula (X') is connected with other positions of a molecule through one unpositioned connecting bond extending from the centre of a benzene ring on one side, and its meaning includes any one possible connecting mode represented by formulae (X'-1) to (X'-4):

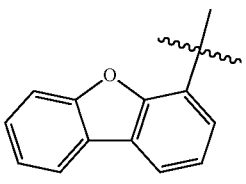
(X')

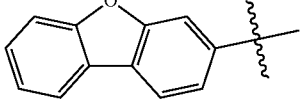
(X'-1)

(X'-2)

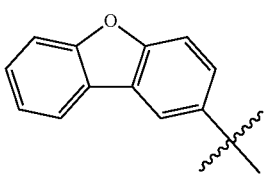

(X'-3)

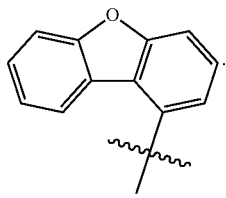

(X'-4)

In the following, the meaning for unpositioned connection or unpositioned substitution is the same as here, which will not be repeated later.

In some embodiments of the present disclosure, each $R_1$, each $R_2$, and each $R_3$ are each independently selected from hydrogen, deuterium, cyano, fluorine, trifluoromethyl, trideuteromethyl, trimethylsilyl, methyl, ethyl, isopropyl, tert-butyl, trifluoromethyl, phenyl, biphenyl, naphthyl, or pyridyl.

In some embodiments, L, $L_1$, and $L_2$ are each independently selected from a single bond and substituted or unsubstituted arylene with 6, 10, 12, 13, 14, 15 or 18 carbon atoms.

In some embodiments of the present disclosure, L is selected from a single bond and substituted or unsubstituted arylene with 6 to 12 carbon atoms.

Optionally, substituents in the L are selected from a halogen group, cyano, alkyl with 1 to 5 carbon atoms or phenyl.

Optionally, the substituents in the L are selected from fluorine, cyano, alkyl with 1 to 5 carbon atoms or phenyl.

Optionally, L is selected from a single bond, substituted or unsubstituted phenylene, substituted or unsubstituted naphthylene and substituted or unsubstituted biphenylene.

More specifically, substituents in the L are each independently fluorine, cyano, methyl, ethyl, n-propyl, isopropyl, tert-butyl or phenyl.

In other embodiments of the present disclosure, L is selected from a single bond.

In some embodiments of the present disclosure, L is selected from a single bond or the group consisting of:

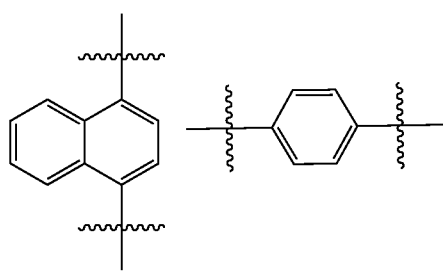

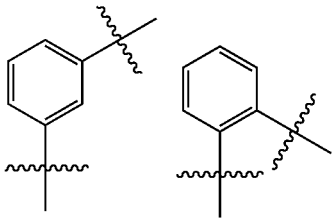

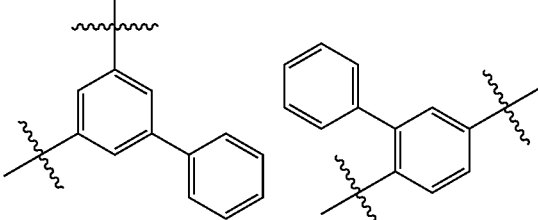

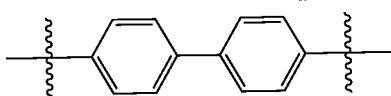

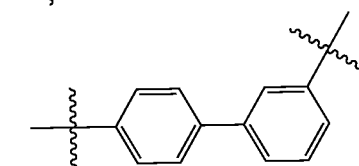

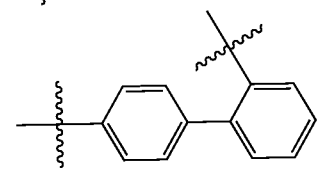

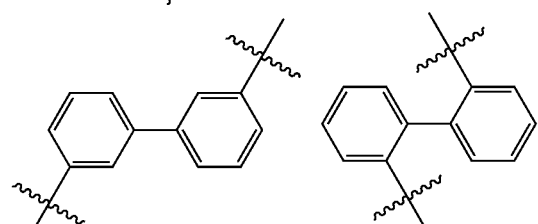

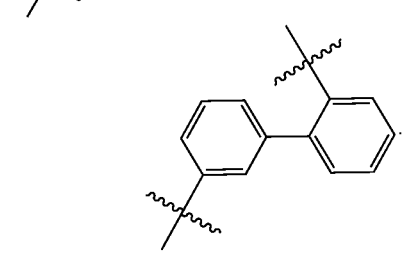

In some embodiments of the present disclosure, $L_1$ and $L_2$ are each independently selected from a single bond and substituted or unsubstituted arylene with 6 to 12 carbon atoms.

Optionally, substituents in the $L_1$ and the $L_2$ are each independently selected from fluorine, cyano, alkyl with 1 to 5 carbon atoms, or phenyl.

In other embodiments of the present disclosure, $L_1$ and $L_2$ are each independently selected from a single bond, substituted or unsubstituted phenylene, substituted or unsubstituted naphthylene, or substituted or unsubstituted biphenylene.

Optionally, substituents in the $L_1$ and the $L_2$ are each independently selected from fluorine, cyano, methyl, ethyl, n-propyl, isopropyl, tert-butyl or phenyl.

In some embodiments of the present disclosure, $L_1$ and $L_2$ are each independently selected from a single bond and a substituted or unsubstituted group T, where the unsubstituted group T is selected from the group consisting of:

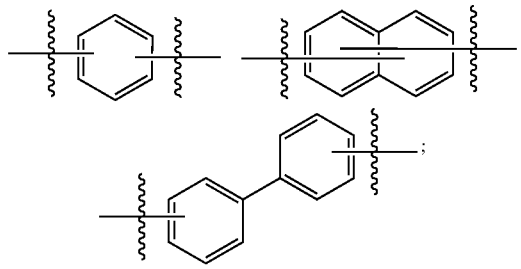

wherein ⌇ represents a chemical bond; the substituted group T contains one or more substituents selected from fluorine, cyano, methyl, ethyl, n-propyl, isopropyl, tert-butyl and phenyl; and when the substituted group T contains a plurality of substituents, the substituents are the same or different.

Optionally, $L_1$ and $L_2$ are each independently selected from a single bond or the group consisting of:

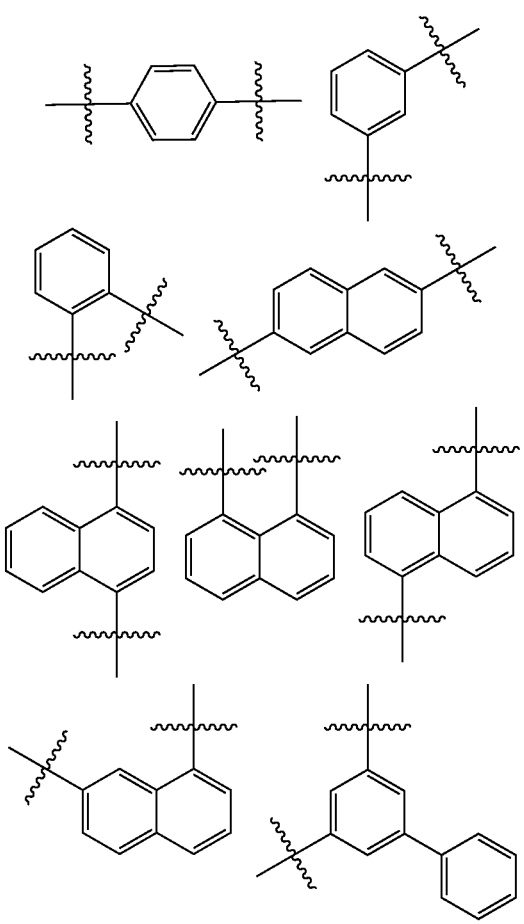

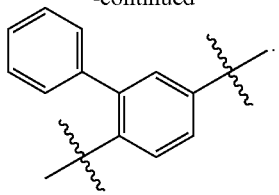

Optionally, $L_1$ and $L_2$ are each independently selected from a single bond or the group consisting of:

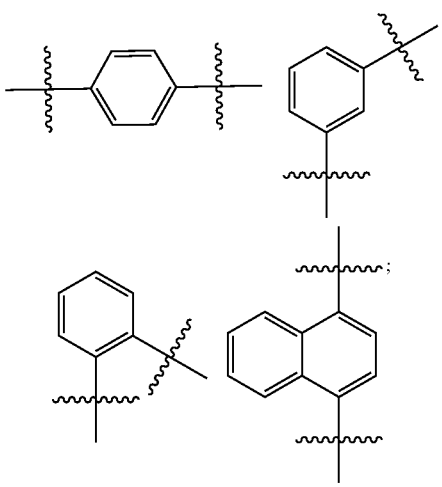

L is selected from a single bond or

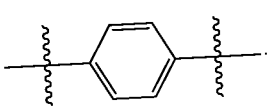

In some embodiments of the present disclosure, when $Ar_1$ and $Ar_2$ are selected from substituted or unsubstituted aryl with 6 to 30 carbon atoms, the number of carbon atoms of the substituted or unsubstituted aryl can be 6, 12, 13, 14, 15, 18, 20, 24, 25, 28, 29 or 30, and of course, the number of carbon atoms can also be other numbers, which will not be listed here. In the present disclosure, biphenyl can be understood as phenyl-substituted aryl or unsubstituted aryl.

In some embodiments of the present disclosure, $Ar_1$ and $Ar_2$ are each independently selected from substituted or unsubstituted aryl with 6 to 25 carbon atoms.

Optionally, substituents in the $Ar_1$ and the $Ar_2$ are each independently selected from a halogen group, cyano, alkyl with 1 to 5 carbon atoms, haloalkyl with 1 to 5 carbon atoms, cycloalkyl with 5 to 10 carbon atoms, aryl with 6 to 12 carbon atoms or triphenylsilyl; optionally, in $Ar_1$ and $Ar_2$, any two adjacent substituents form a saturated or unsaturated ring with 5 to 13 carbon atoms.

For example, in $Ar_1$ and $Ar_2$, any two adjacent substituents may form cyclohexane

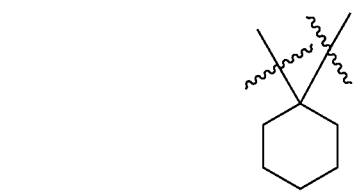 [SMILES: *C1(*)CCCCC1]

cyclopentane

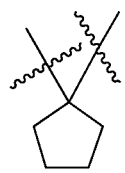 [SMILES: *C1(*)CCCC1]

a benzene ring, a naphthalene ring, or a fluorene ring

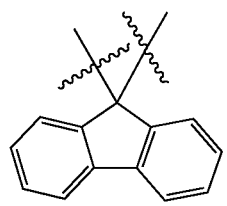 [SMILES: *C1(*)c2ccccc2-c2ccccc21]

In other embodiments of the present disclosure, $Ar_1$ and $Ar_2$ are each independently selected from substituted or unsubstituted phenyl, substituted or unsubstituted naphthyl, substituted or unsubstituted biphenyl, substituted or unsubstituted phenanthryl, substituted or unsubstituted fluorenyl, substituted or unsubstituted terphenyl, substituted or unsubstituted triphenylene, and substituted or unsubstituted spirobifluorenyl.

Optionally, substituents in the $Ar_1$ and the $Ar_2$ are each independently selected from fluorine, cyano, methyl, ethyl, n-propyl, isopropyl, tert-butyl, trifluoromethyl, triphenylsilyl, cyclohexyl, adamantyl, phenyl, or biphenyl.

Optionally, in $Ar_1$ and $Ar_2$, any two adjacent substituents form a fluorene ring.

In other embodiments of the present disclosure, $Ar_1$ and $Ar_2$ are each independently selected from a substituted or unsubstituted group V, where the unsubstituted group V is selected from the group consisting of:

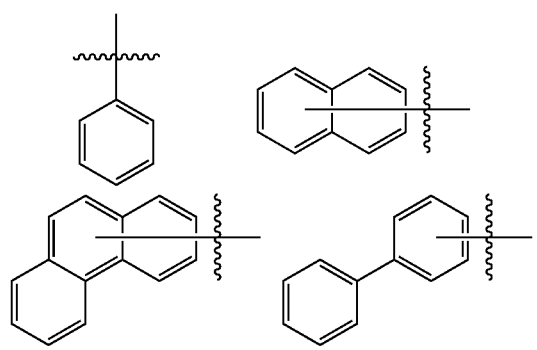

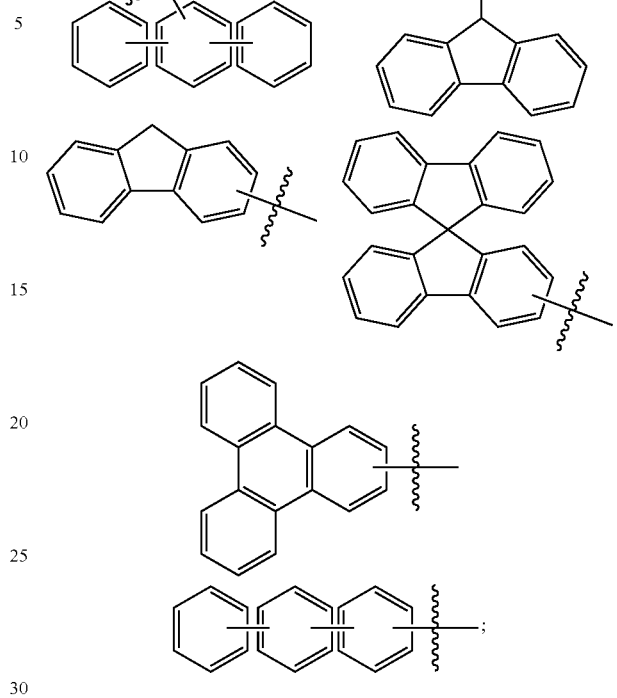

where $\dashv\!\!\!\vdash$ represents a chemical bond; the substituted group V contains one or more substituents selected from fluorine, cyano, methyl, ethyl, n-propyl, isopropyl, tert-butyl, cyclohexyl, adamantyl, trifluoromethyl, triphenylsilyl, or phenyl; and when the substituted group V contains a plurality of substituents, the substituents are the same or different.

Optionally, $Ar_1$ and $Ar_2$ are each independently selected from the group consisting of:

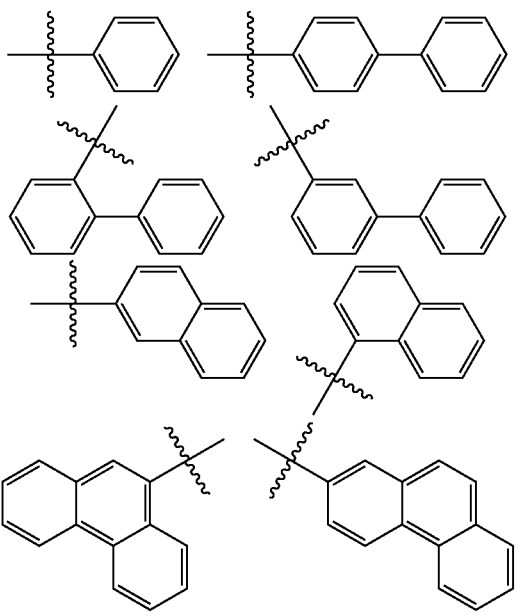

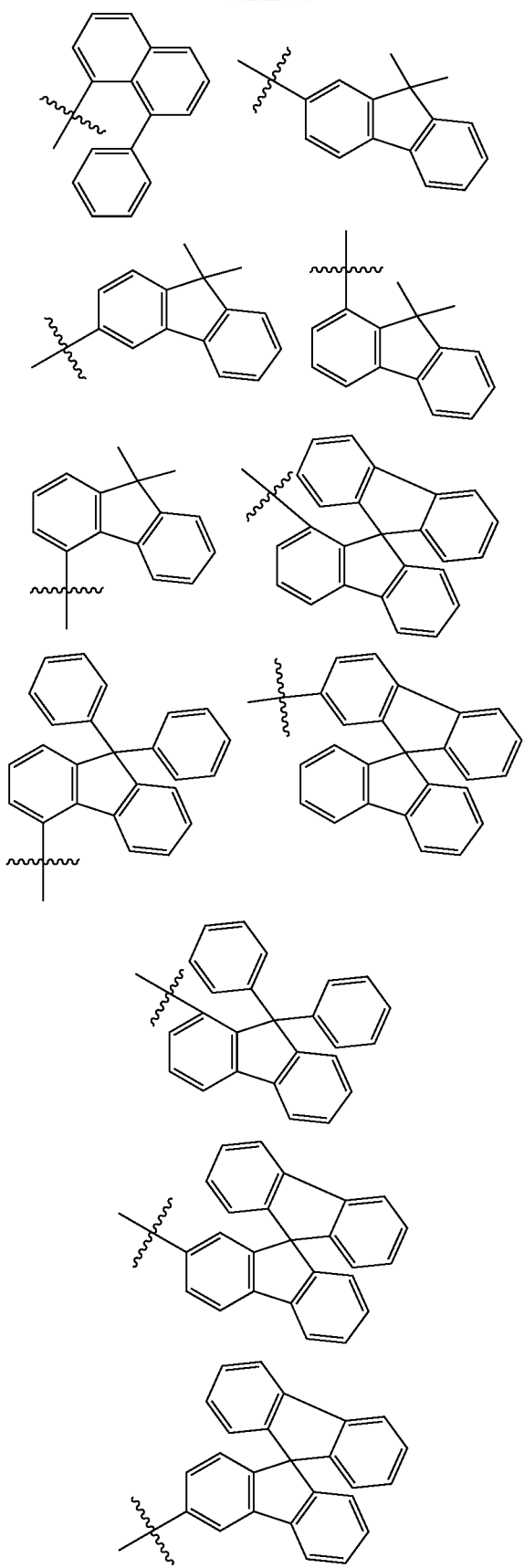
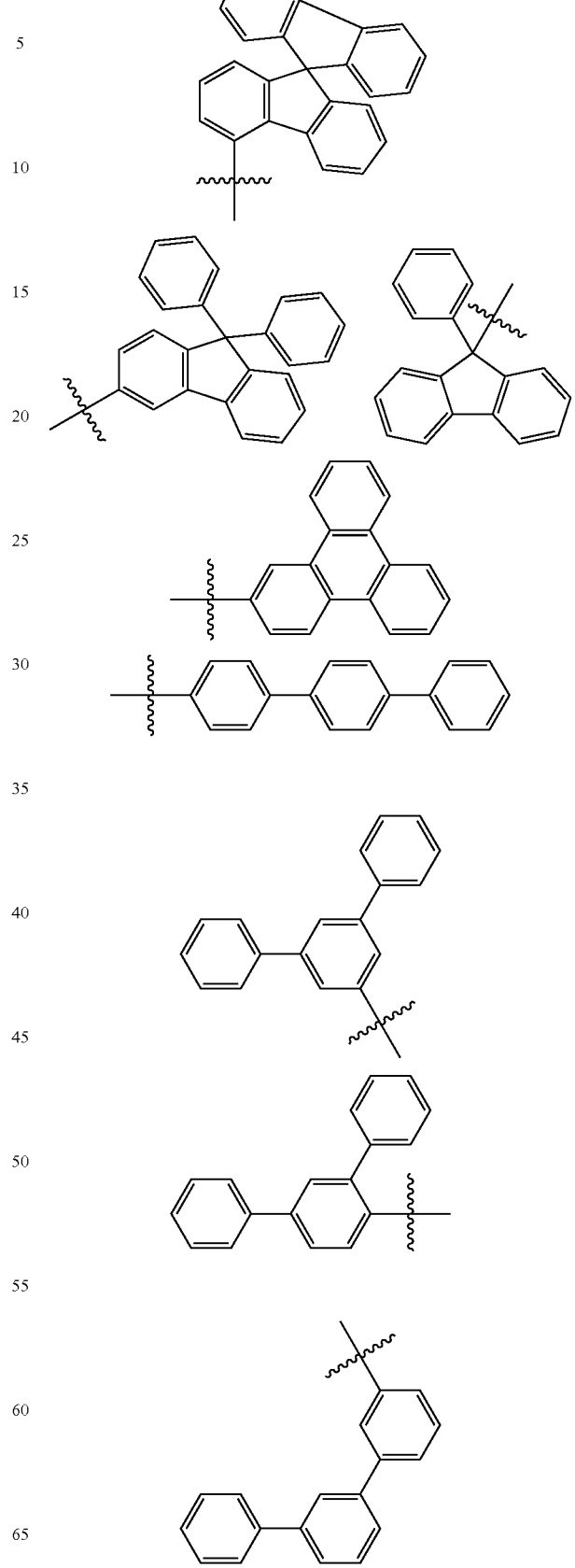

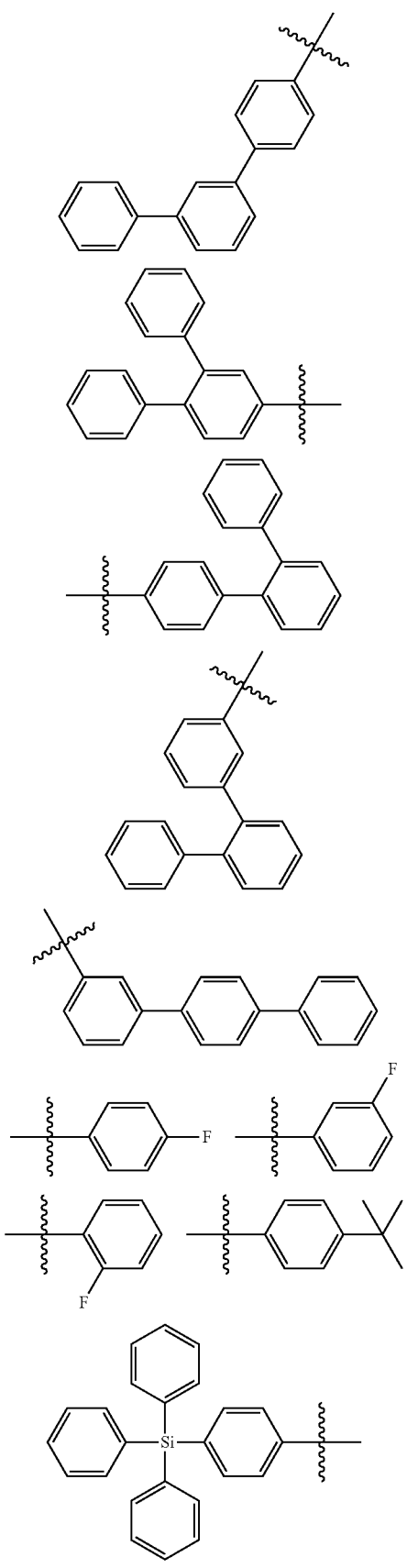
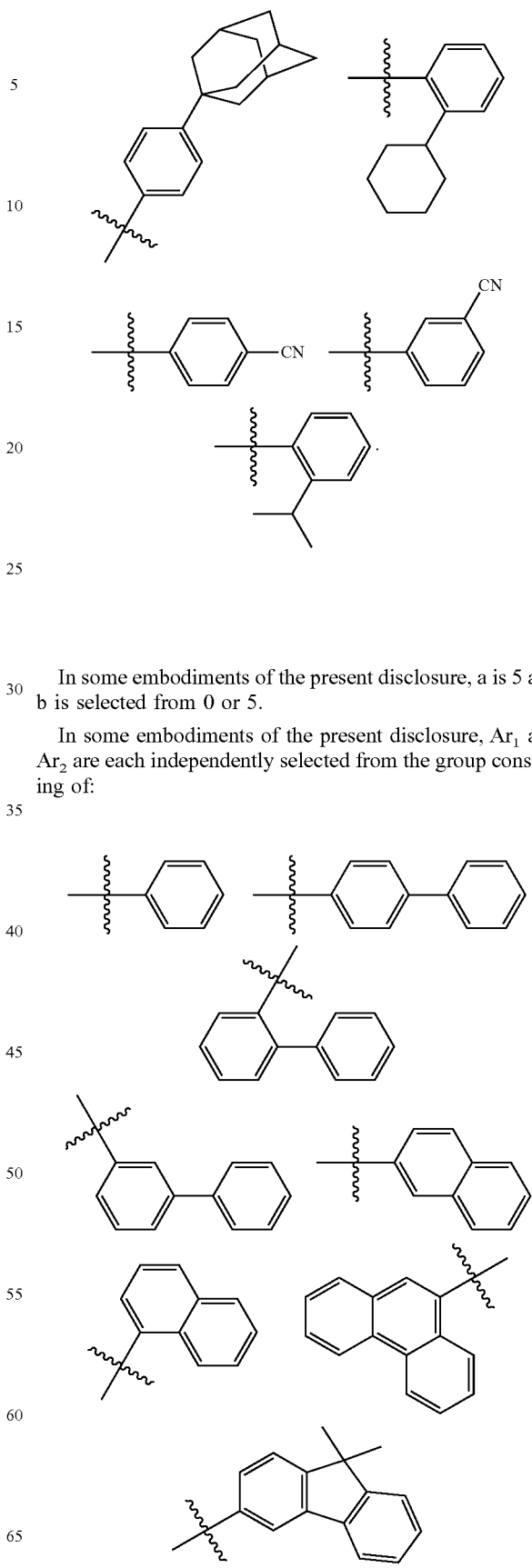
In some embodiments of the present disclosure, a is 5 and b is selected from 0 or 5.
In some embodiments of the present disclosure, $Ar_1$ and $Ar_2$ are each independently selected from the group consisting of:

-continued

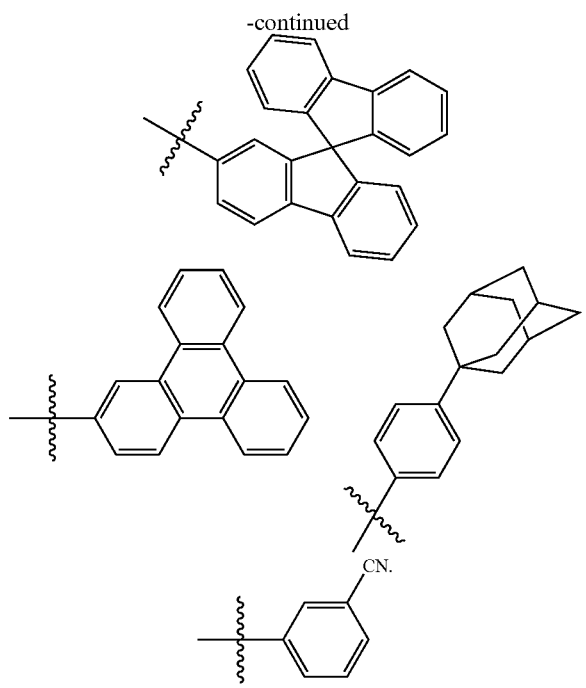

In some embodiments of the present disclosure,

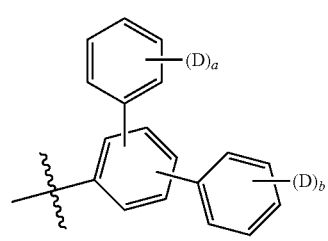

in the formula 1 is selected from the following structures:

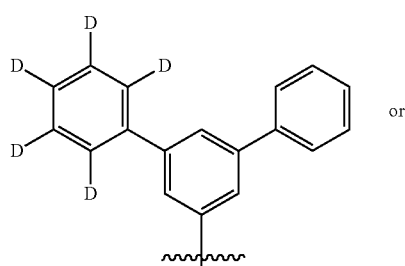

or

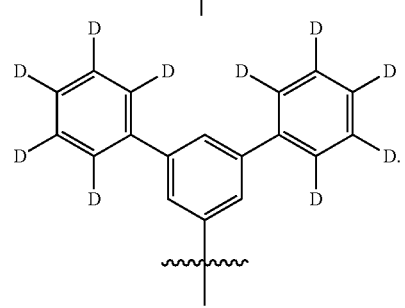

For deuteration of phenyl in the periphery of diphenyl-substituted phenyl, in order to reduce the size of the diphenyl-substituted phenyl and make its spatial overlap with the triazinyl more compact, at least one phenyl group is generally perdeuterated.

When both $Ar_1$ and $Ar_2$ are selected from aryl and three benzene rings in

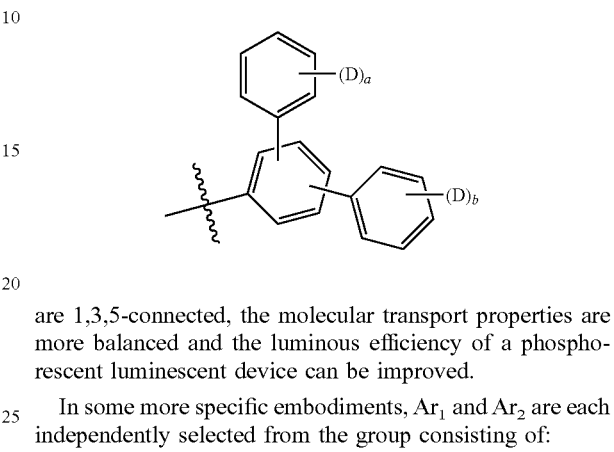

are 1,3,5-connected, the molecular transport properties are more balanced and the luminous efficiency of a phosphorescent luminescent device can be improved.

In some more specific embodiments, $Ar_1$ and $Ar_2$ are each independently selected from the group consisting of:

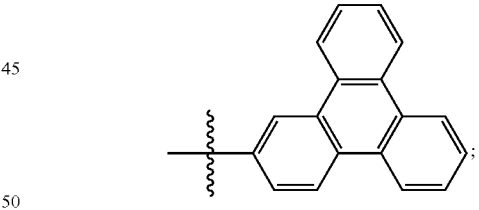

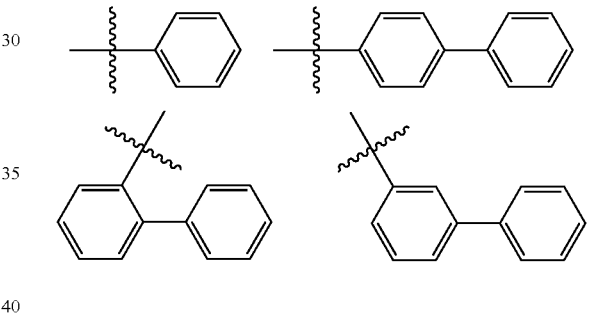

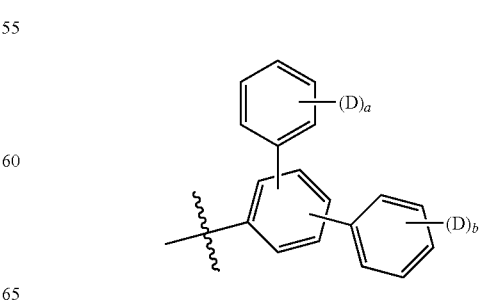

in the formula 1 is selected from the following structures:
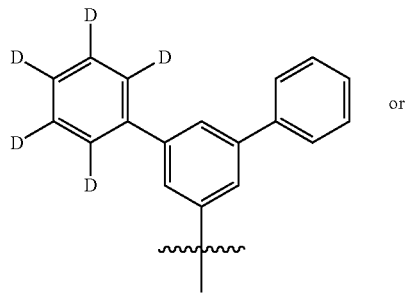
or
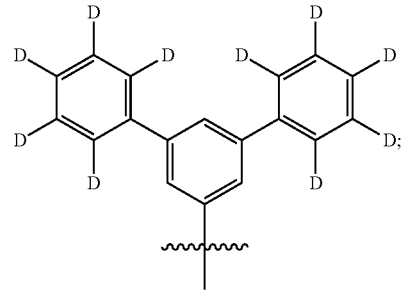
L is a single bond;
$L_1$ and $L_2$ are each independently selected from a single bond or the group consisting of:
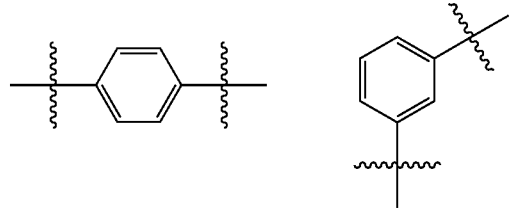
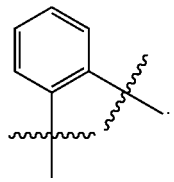
Optionally, the nitrogen-containing compound is selected from the group consisting of:
1
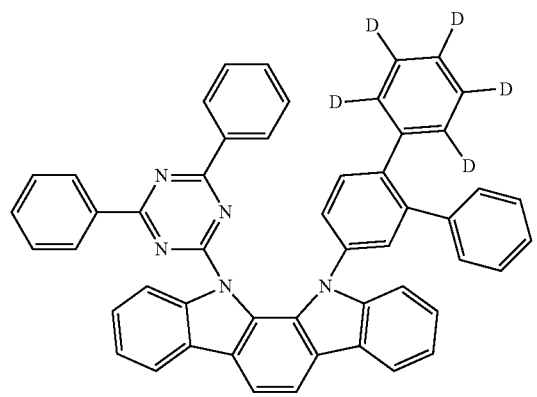
2
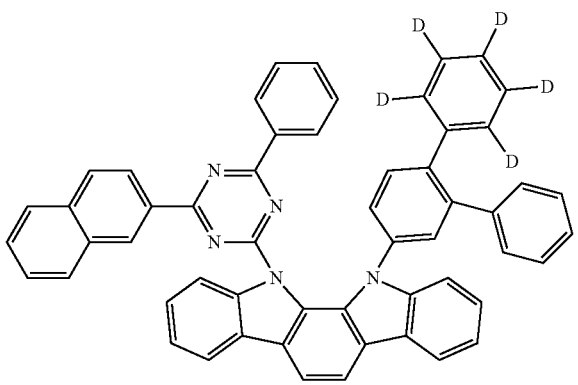
3
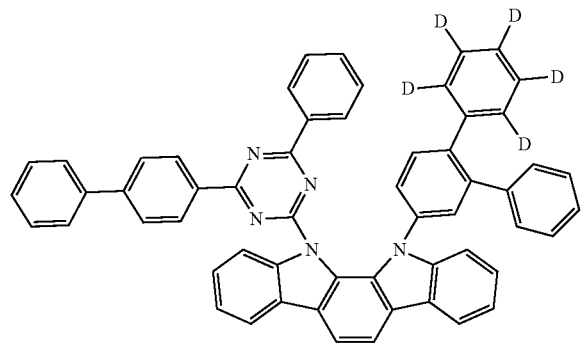
4
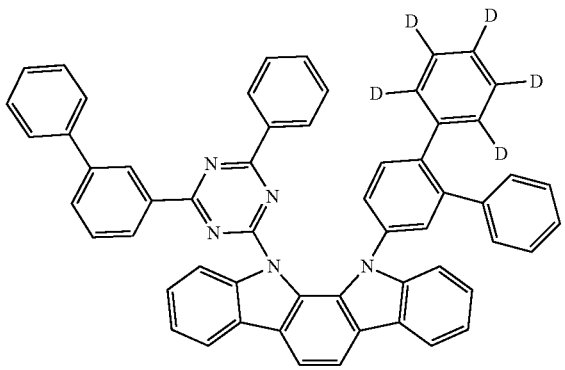

5
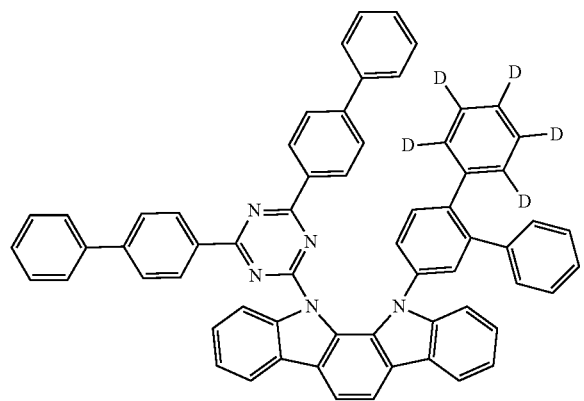
6
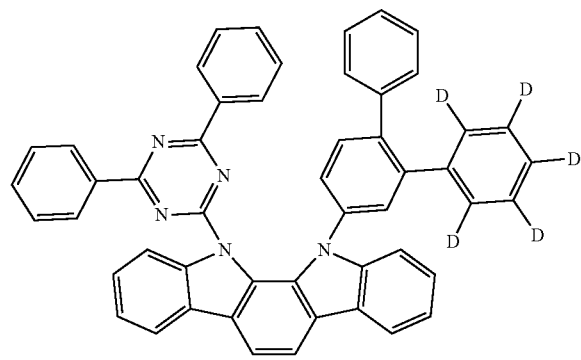
7
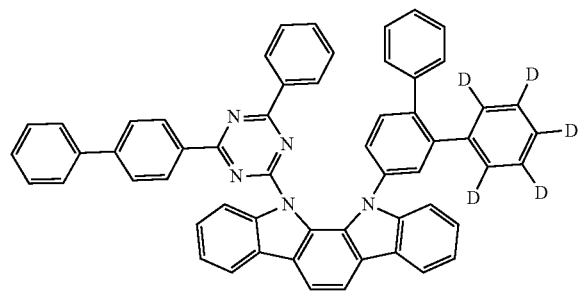
8
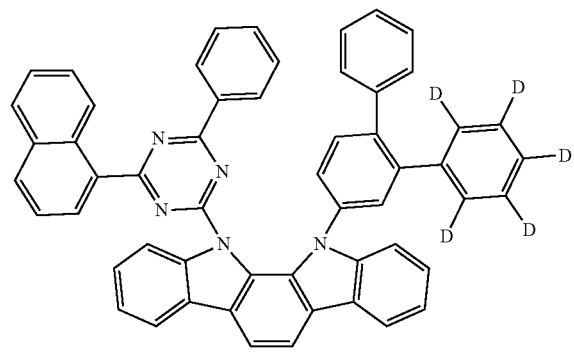
11
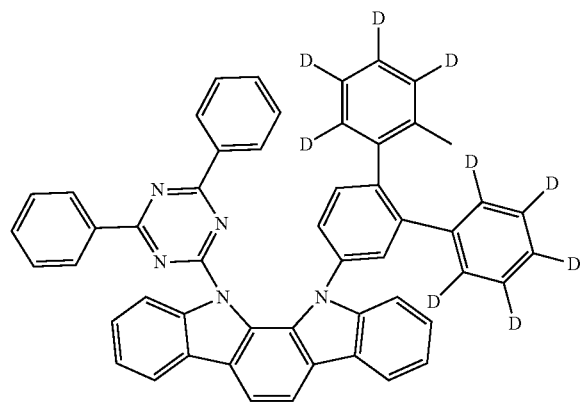
12
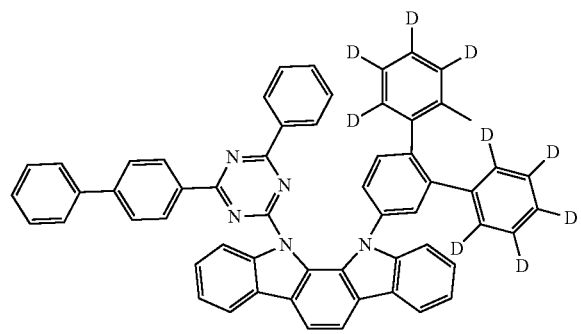

-continued
13
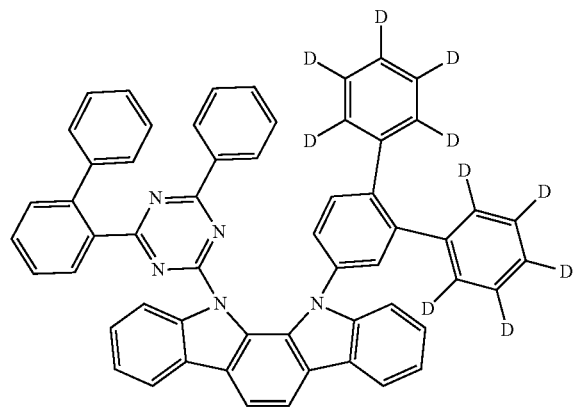
16
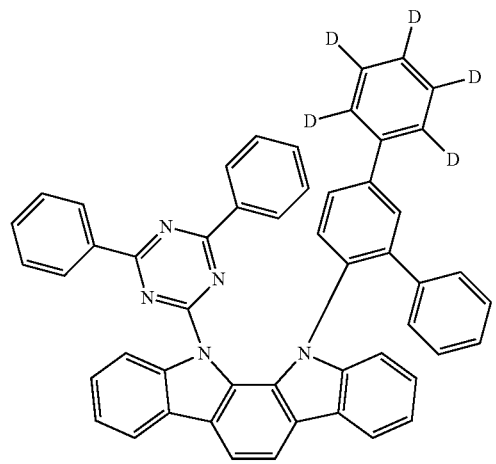
17
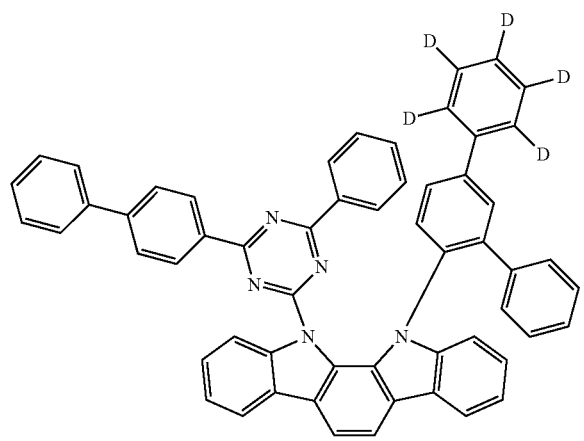
18
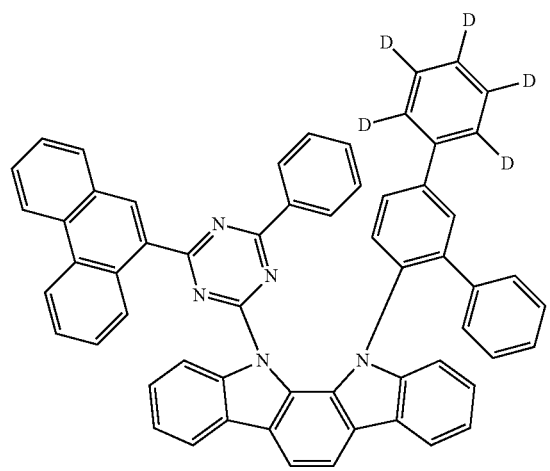
19
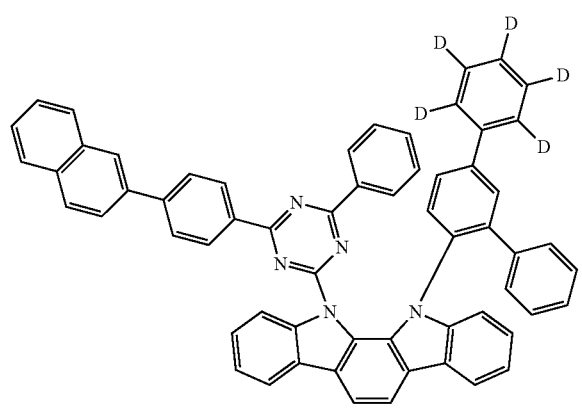
21
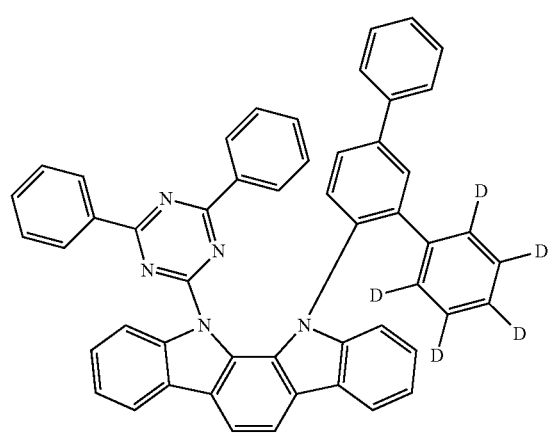

-continued
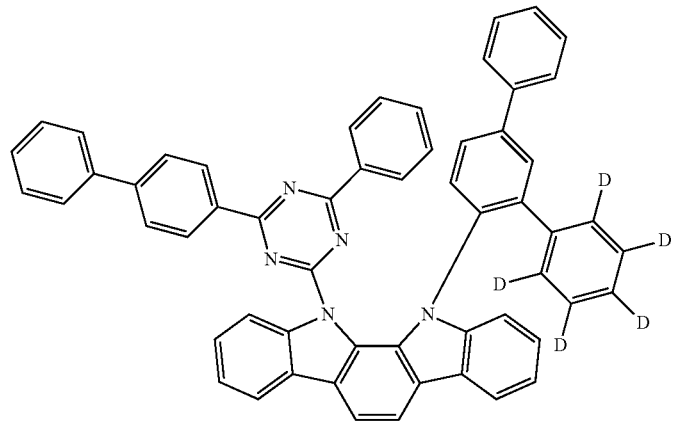
22
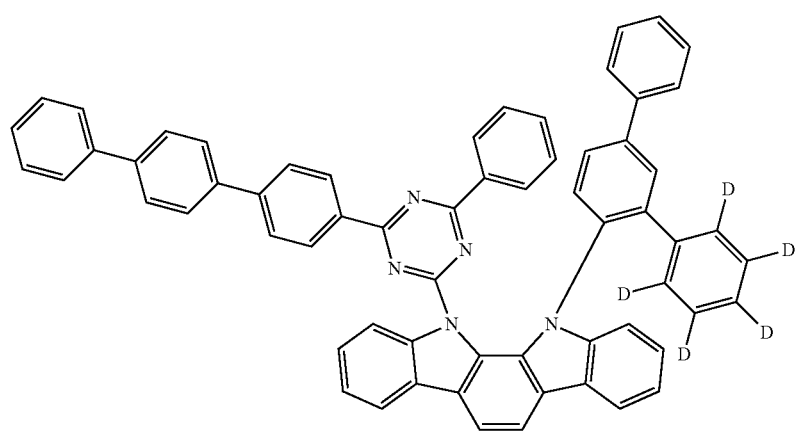
24
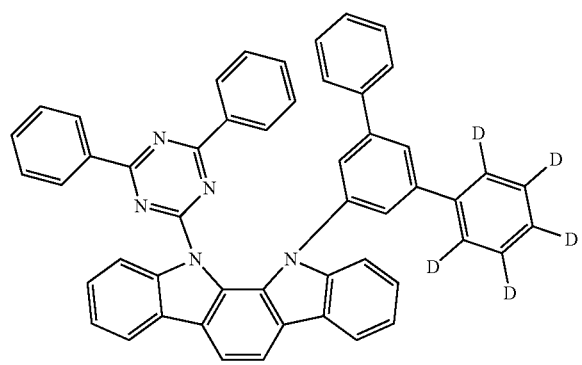
31
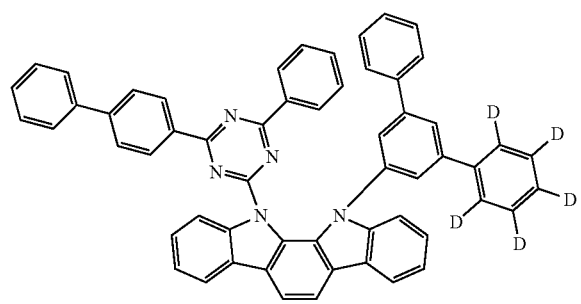
32

25
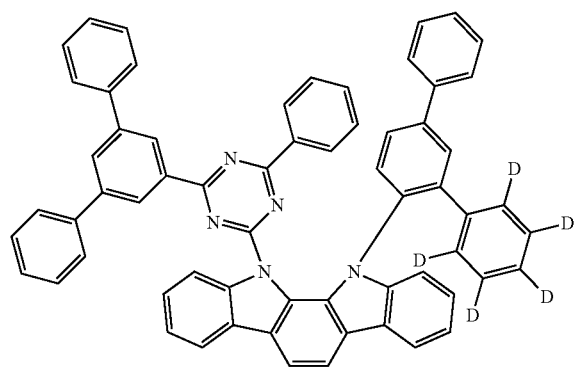
26
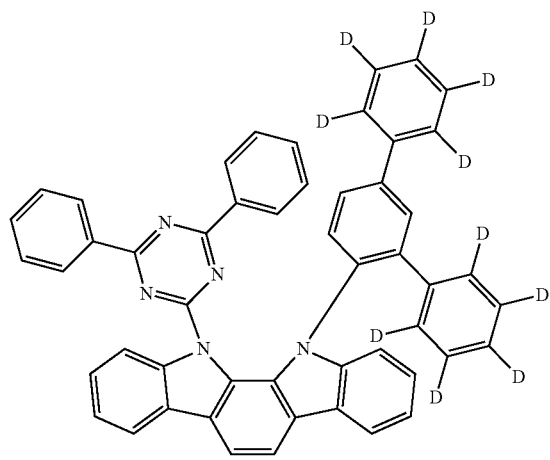
27
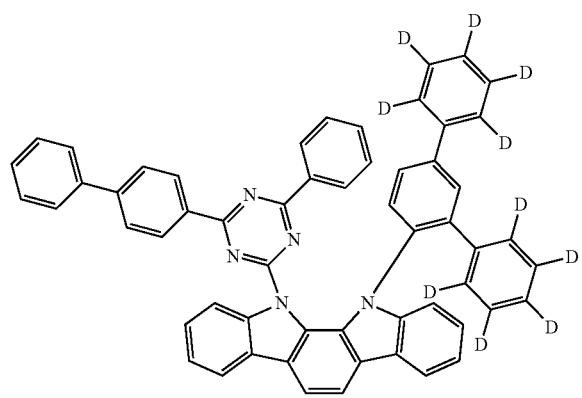
28
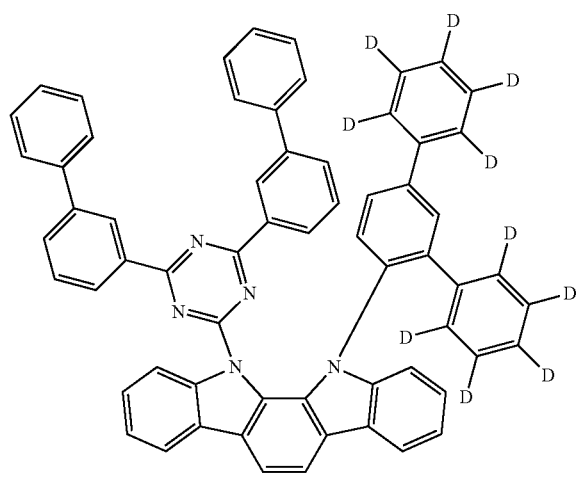
33
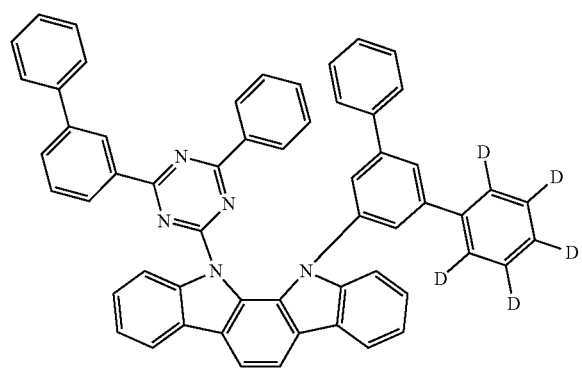
36
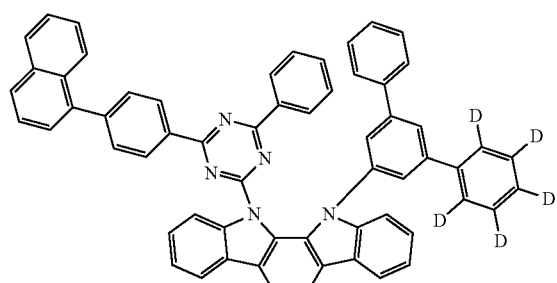

-continued
38
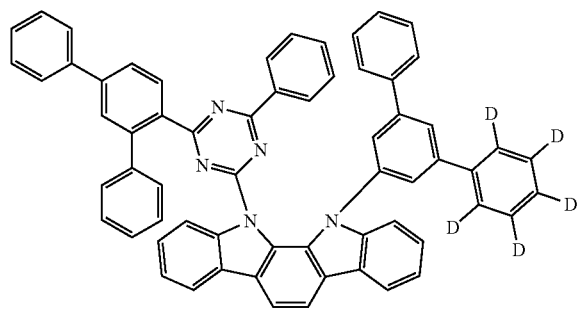
39
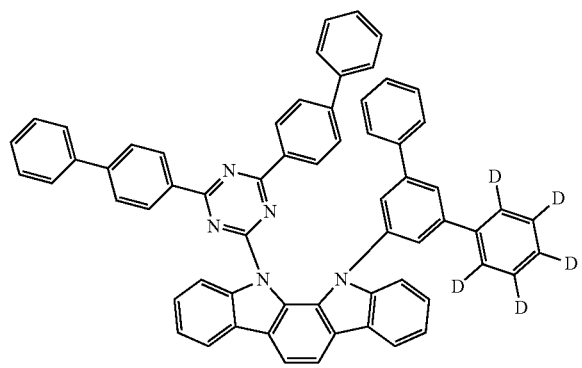
41
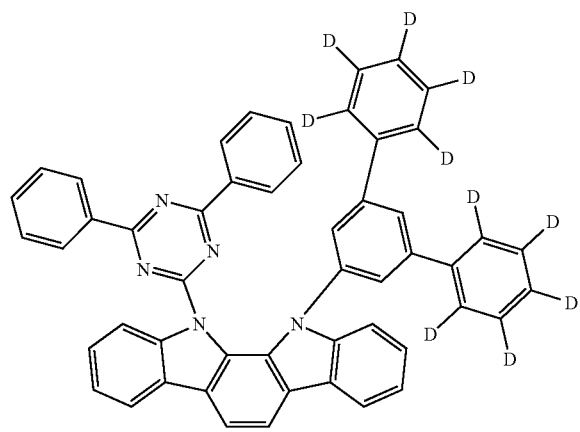
42
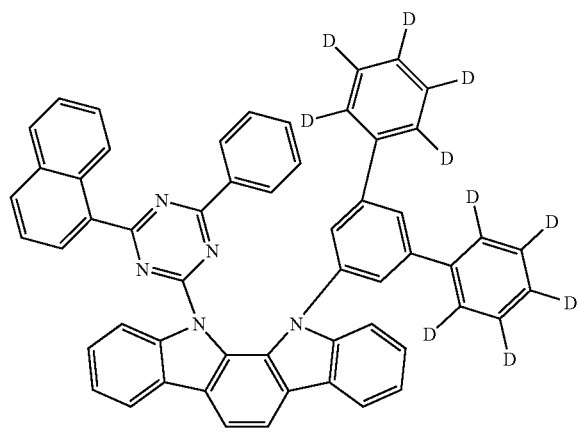
43
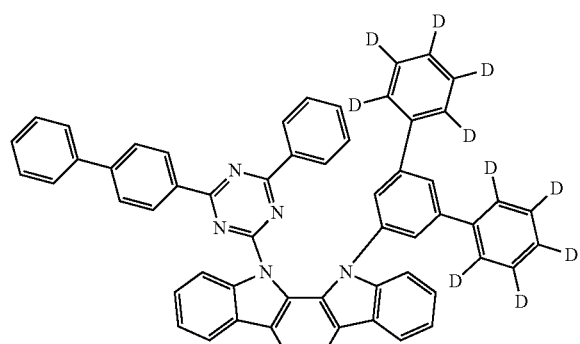
44
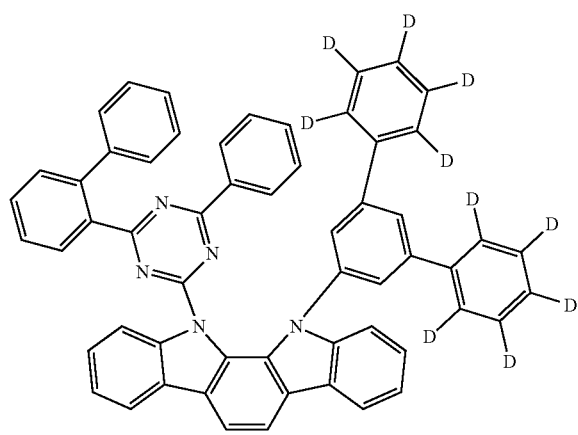

-continued
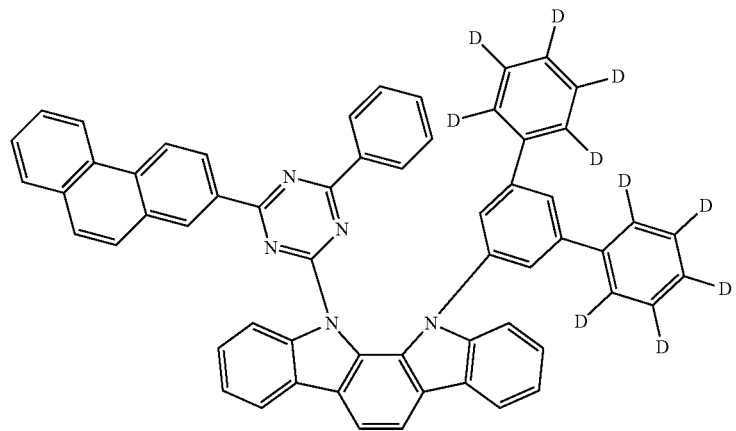
47
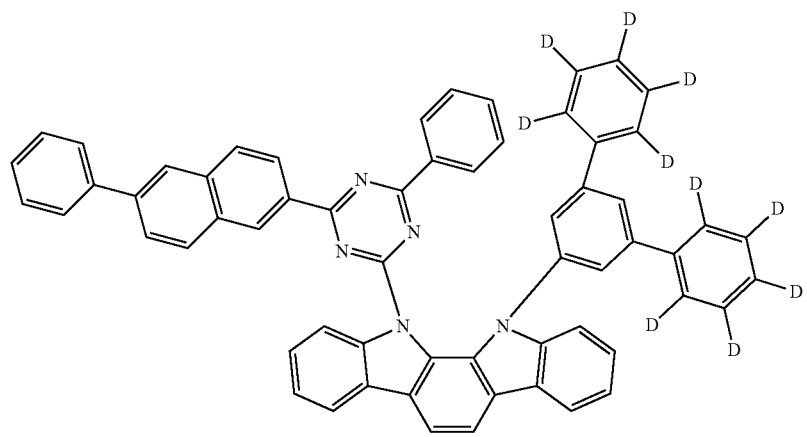
48
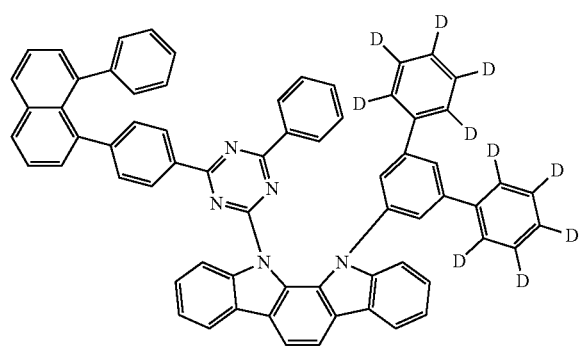
49
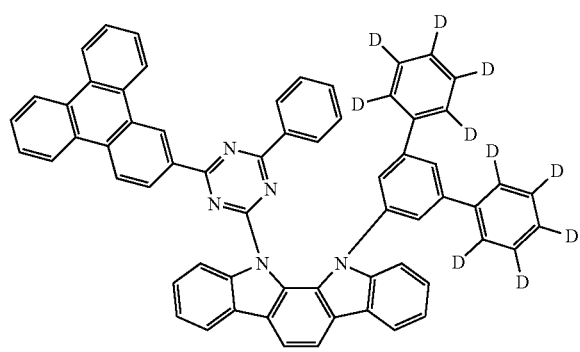
50

-continued
51
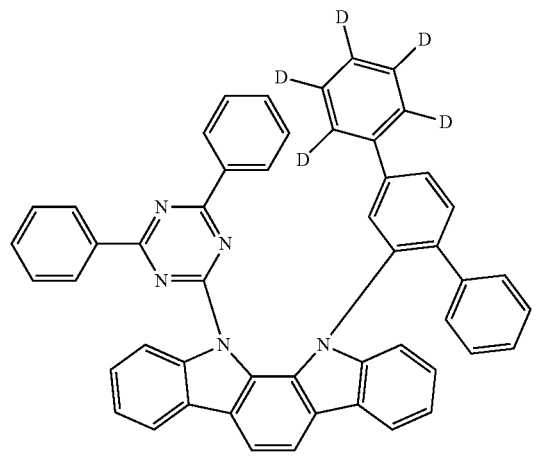
52
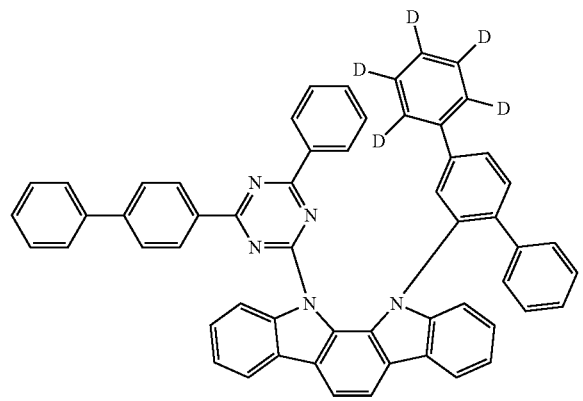
53
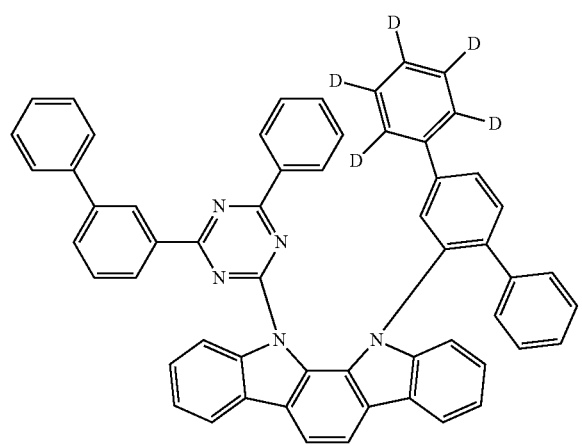
56
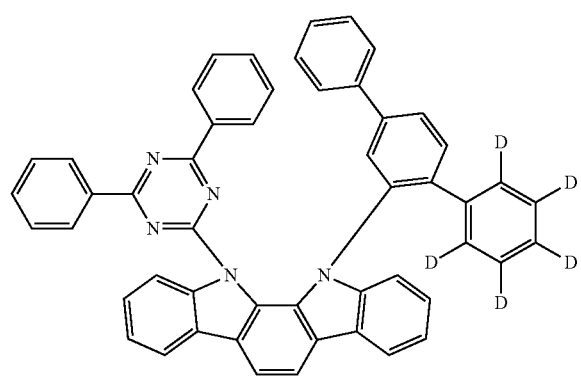
57
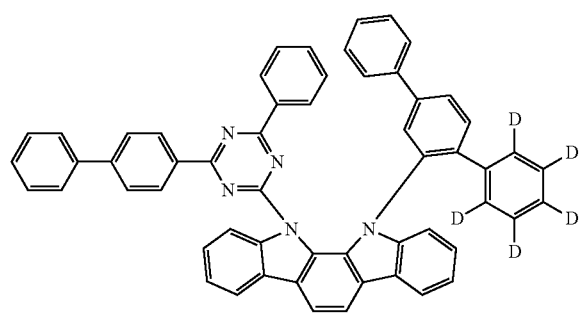
58
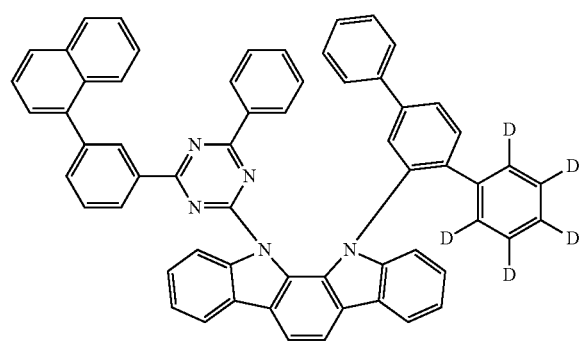

-continued
59
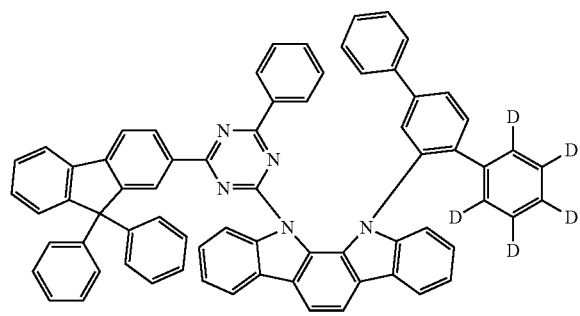
61
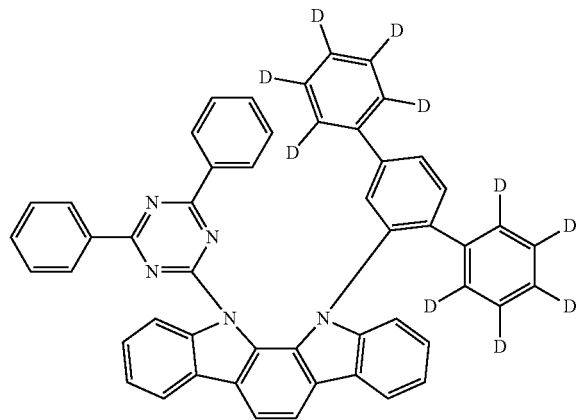
62
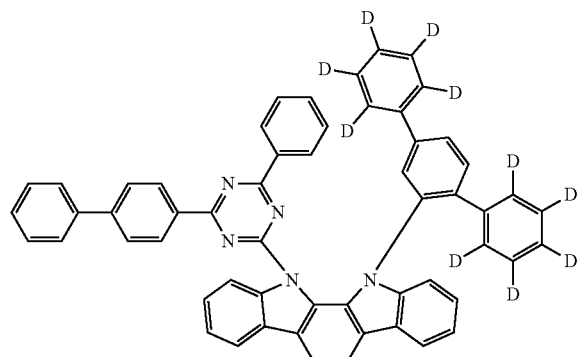
63
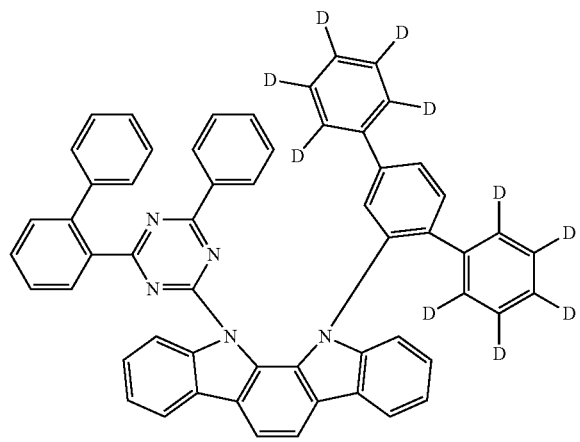
64
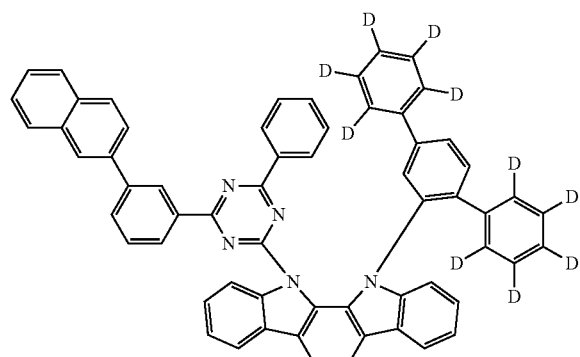
65
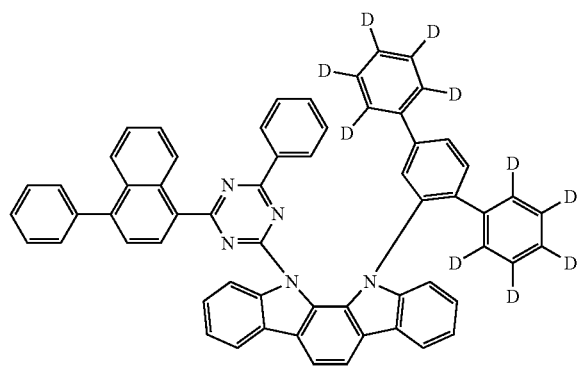

-continued
66
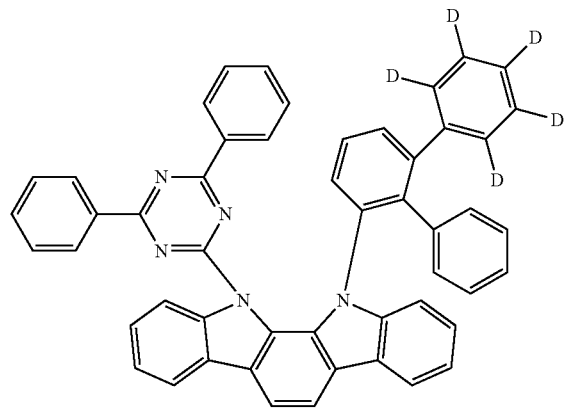
67
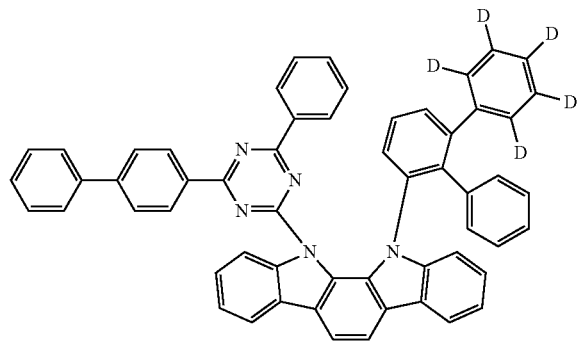
68
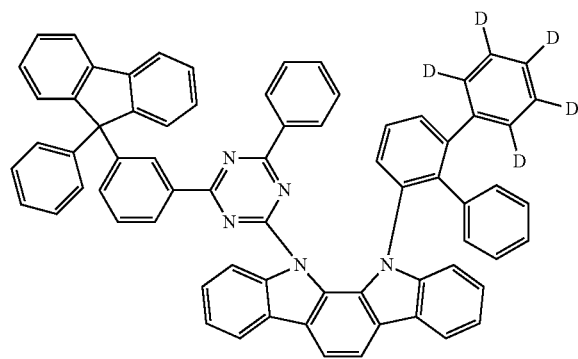
69
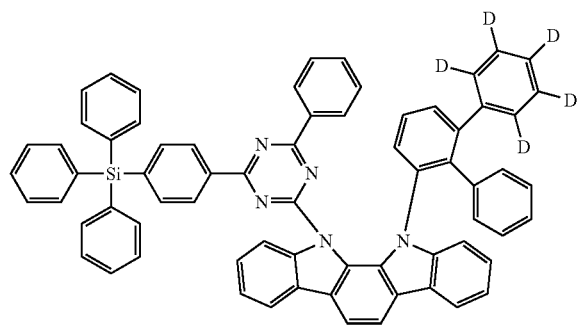
70
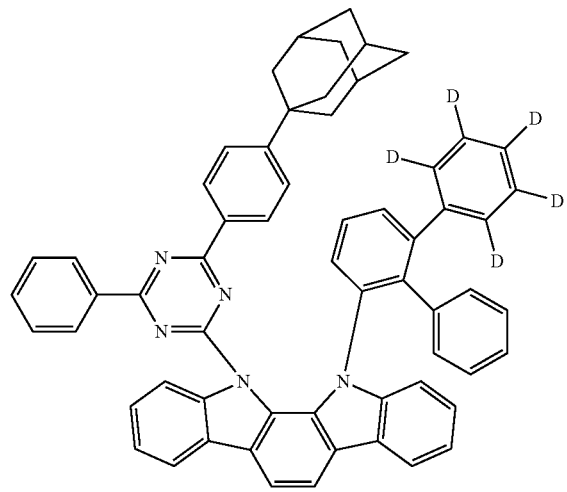
71
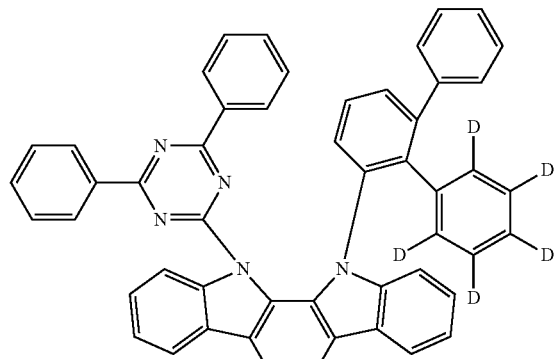

72
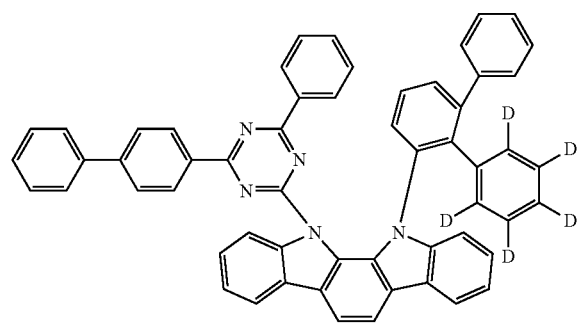
74
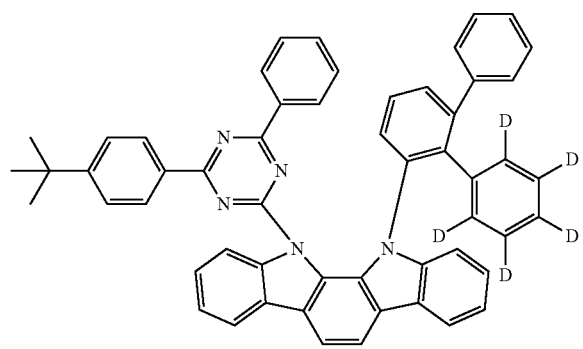
75
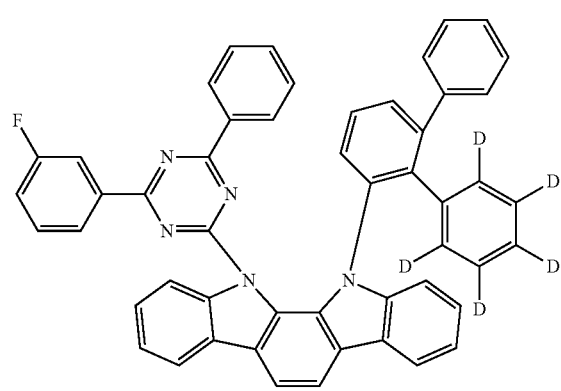
76
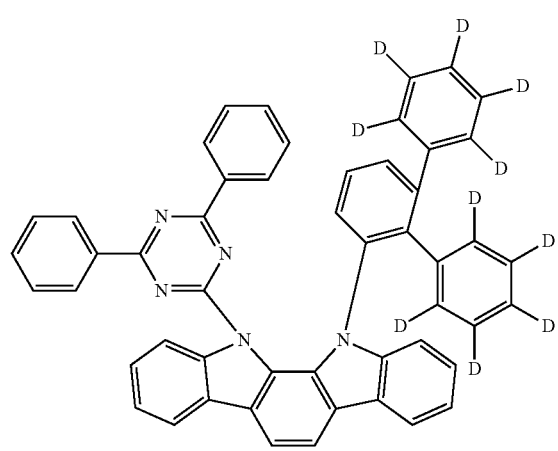
77
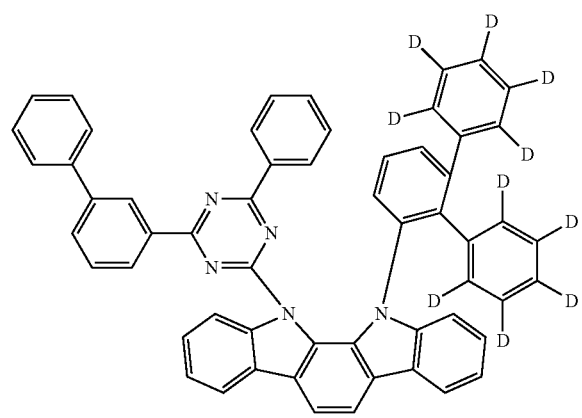
78
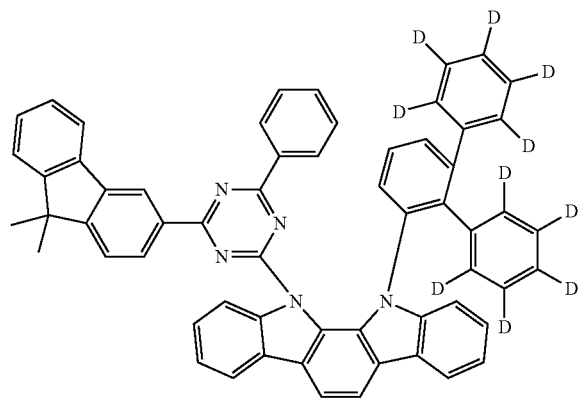

-continued
80
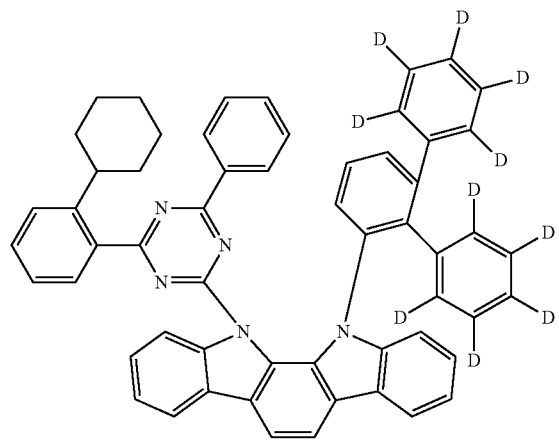
81
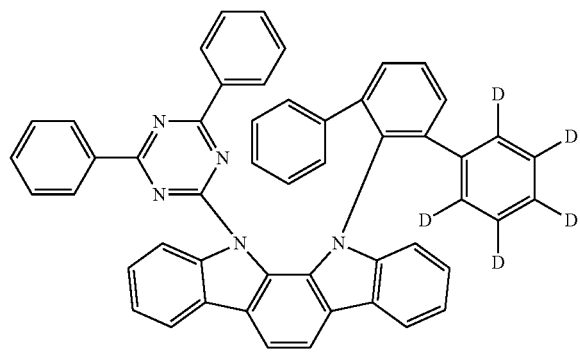
82
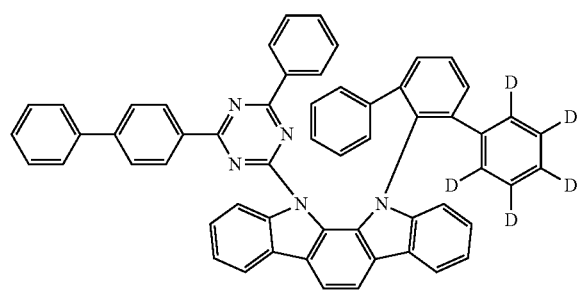
83
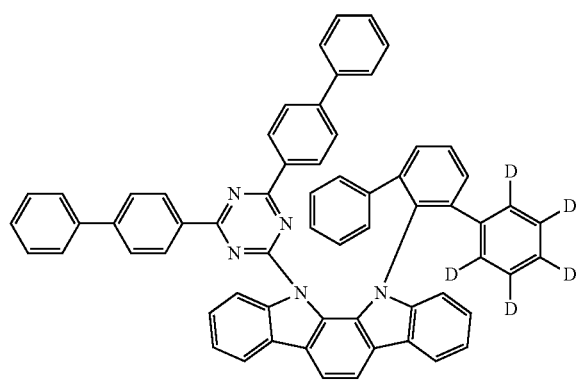
85
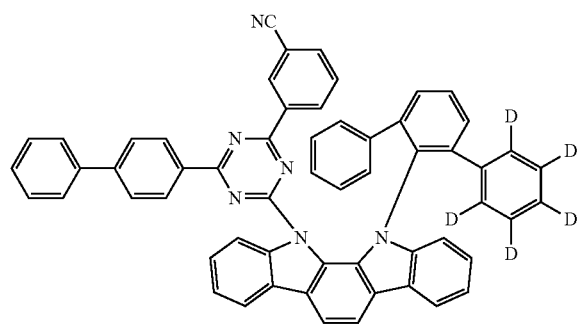
86
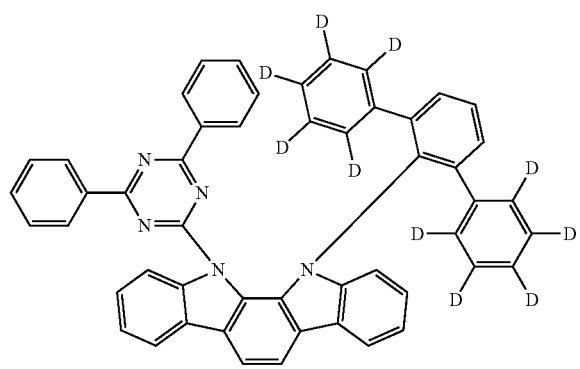
87
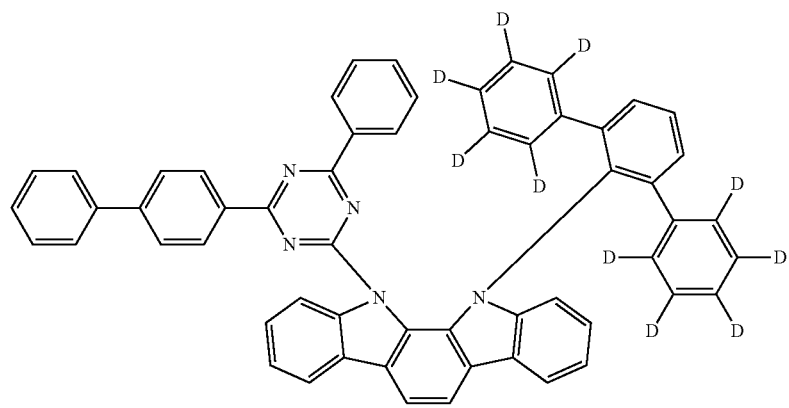

88
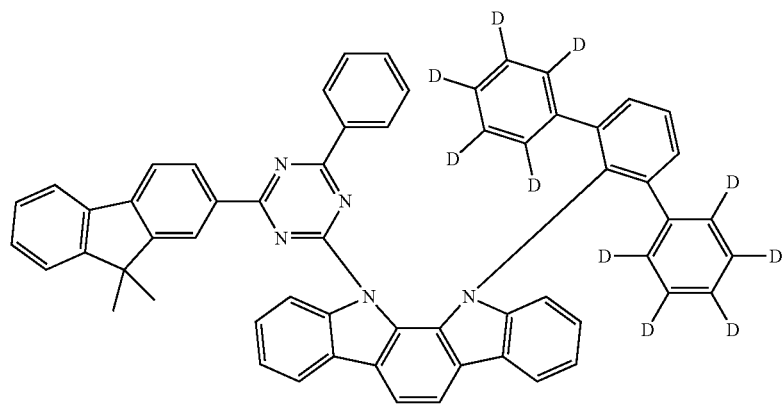
90
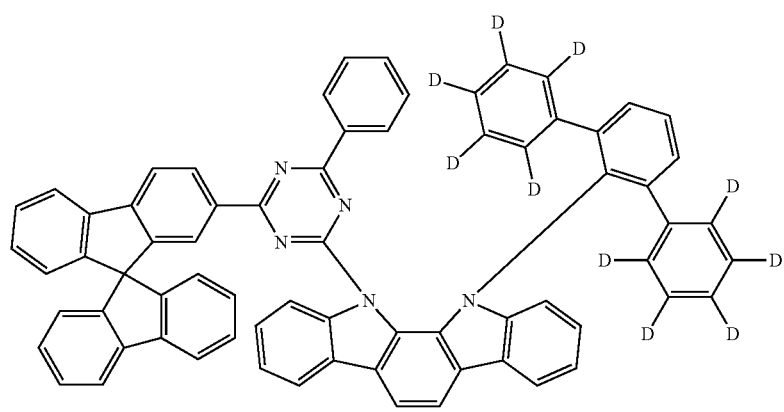
91
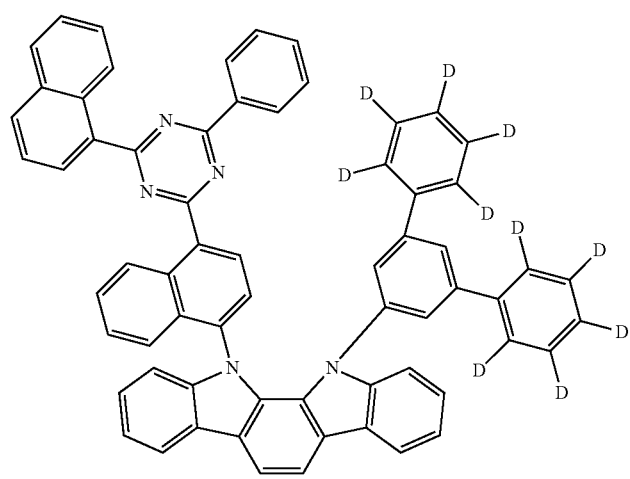

-continued

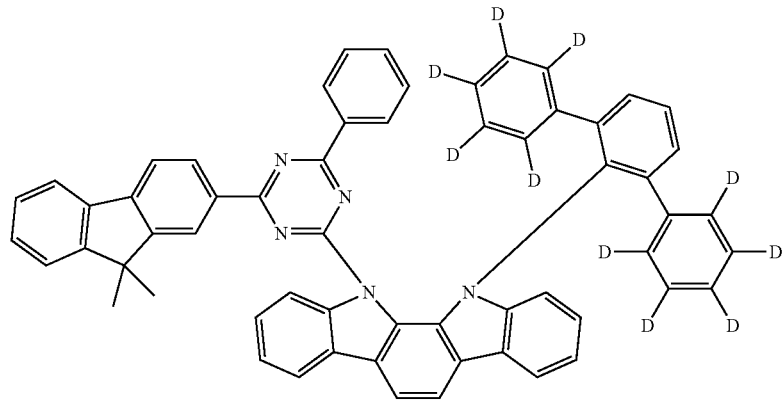

92

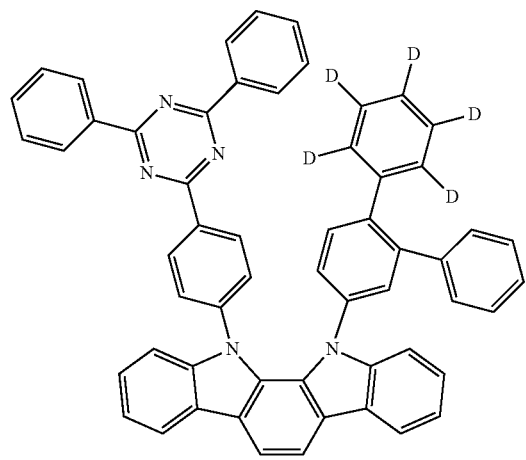

93

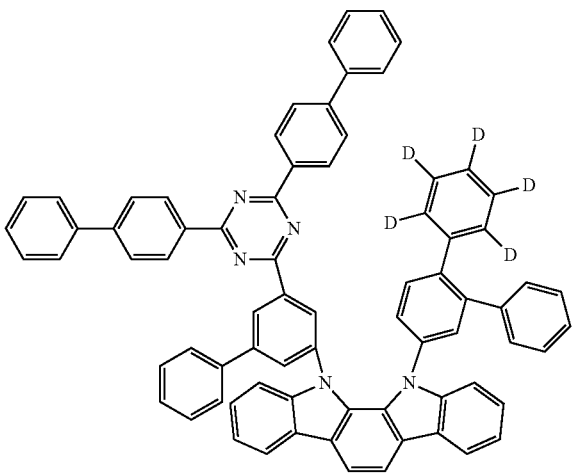

94

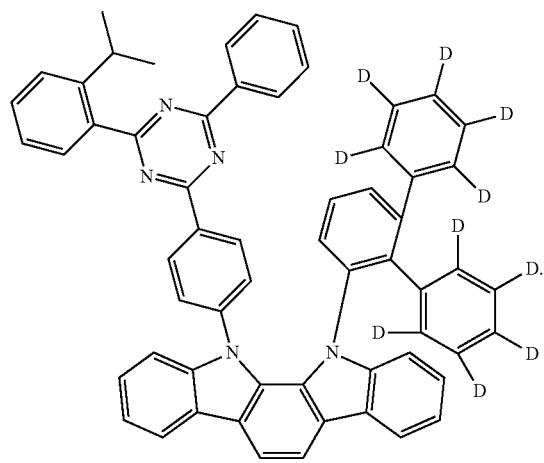

95

The present disclosure also provides an organic electroluminescent device, including an anode and a cathode which are oppositely disposed, and at least one functional layer between the anode and the cathode, where the functional layer includes the nitrogen-containing compound of the present disclosure.

Further, the functional layer includes an organic luminescent layer including the nitrogen-containing compound.

In one specific embodiment of the present disclosure, the organic electroluminescent device is a green phosphorescent organic electroluminescent device.

In one specific embodiment of the present disclosure, as shown in FIG. 1, the organic electroluminescent device of the present disclosure includes an anode 100, a cathode 200 and at least one functional layer 300 between the anode layer and the cathode layer. The functional layer 300 includes a hole injection layer 310, a hole transport layer 321, a hole auxiliary layer 322, an organic luminescent layer 330, an electron transport layer 350, and an electron injection layer 360 which are stacked. The organic luminescent layer 330 includes the nitrogen-containing compound according to the first aspect of the present disclosure.

Optionally, the anode 100 includes the following anode materials which are preferably materials having a large work function that facilitate hole injection into the functional layer. Specific examples of the anode materials include metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to these. A transparent electrode containing indium tin oxide (ITO) as the anode is preferably included.

Optionally, the hole transport layer 321 includes one or more hole transport materials, and the hole transport materials can be selected from a carbazole polymer, carbazole connected triarylamine compounds or other types of compounds, which are not specially limited in the present disclosure. For example, the hole transport layer 321 is composed of HT-01.

Optionally, the hole auxiliary layer 322 includes one or more hole transport materials, and the hole transport materials may be selected from a carbazole polymer, carbazole connected triarylamine compounds or other types of compounds, which are not specially limited in the present disclosure. For example, the hole auxiliary layer 322 is composed of HT-02.

Optionally, the organic luminescent layer 330 may be composed of a single luminescent material, and may also include a host material and a guest material. Optionally, the organic luminescent layer 330 is composed of the host material and the guest material, holes injected into the organic luminescent layer 330 and electrons injected into the organic luminescent layer 330 can be recombined in the organic luminescent layer 330 to form excitons, the excitons transfer energy to the host material, the host material transfers energy to the guest material, and then the guest material can emit light.

The guest material of the organic luminescent layer 330 may be a compound having a condensed aryl ring or its derivative, a compound having a heteroaryl ring or its derivative, an aromatic amine derivative, or other materials, which is not specially limited in the present disclosure.

In one more specific embodiment of the present disclosure, the organic electroluminescent device is a green organic electroluminescent device, and the organic luminescent layer 330 includes the nitrogen-containing compound described in the present disclosure, GH-P and a guest material $Ir(ppy)_3$.

The electron transport layer 350 can be of a single-layer structure or a multi-layer structure, and can include one or more electron transport materials, and the electron transport materials can be selected from a benzimidazole derivative, an oxadiazole derivative, a quinoxaline derivative or other electron transport materials, which are not specially limited in the present disclosure. For example, the electron transport layer 350 is composed of ET-01 and LiQ.

Optionally, a hole blocking layer 340 may or may not be arranged between the organic luminescent layer 330 and the electron transport layer 350. The hole blocking layer may include one or more hole blocking materials, which are not specially limited in the present disclosure.

Optionally, the cathode 200 includes the following cathode materials which are materials with a small work function that facilitate electron injection into the functional layer. Specific examples of the cathode materials include metals such as magnesium, calcium, sodium, potassium, titanium, indium, yttrium, lithium, gadolinium, aluminum, silver, tin and lead, or their alloy; or a plurality of layers of materials such as LiF/Al, Liq/Al, $LiO_2$/Al, LiF/Ca, LiF/Al, and $BaF_2$/Ca, but are not limited to these. A metal electrode including silver and magnesium as the cathode is preferably included.

Optionally, the hole injection layer 310 may also be arranged between the anode 100 and the hole transport layer 321 to enhance the ability to inject holes into the hole transport layer 321. The hole injection layer 310 can be made of a benzidine derivative, a starburst arylamine compound, a phthalocyanine derivative or other materials, which is not specially limited in the present disclosure. In one embodiment of the present disclosure, the hole injection layer 310 is composed of CuPC.

Optionally, the electron injection layer 360 may also be arranged between the cathode 200 and the electron transport layer 350 to enhance the ability to inject electrons into the electron transport layer 350. The electron injection layer 360 may include an inorganic material such as an alkali metal sulfide, and an alkali metal halide, or may include a complex of an alkali metal and an organic substance. In one embodiment of the present disclosure, the electron injection layer 360 includes ytterbium (Yb).

The present disclosure also provides an electronic device, including the organic electroluminescent device described in the present disclosure.

Figure 2:
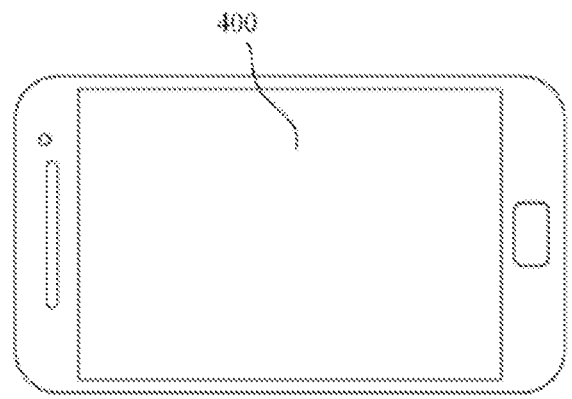
FIG. 2 is a structural schematic diagram of an electronic device according to one embodiment of the present disclosure.

For example, as shown in FIG. 2, the electronic device provided by the present disclosure is an electronic device 400, including the organic electroluminescent device described above. The electronic device can be a display device, a lighting device, an optical communication device or other types of electronic devices, and may include, for example, but is not limited to, a computer screen, a mobile phone screen, a television, electronic paper, an emergency lighting lamp, an optical module and the like. Since the electronic device 400 is provided with the above-described organic electroluminescent device, the electronic device 400 has the same beneficial effects, which will not be repeated here.

The present disclosure will be described in detail with reference to examples, but the following description is intended to explain the present disclosure and is not intended to limit the scope of the present disclosure in any way. The examples only list the synthesis process of some compounds, and other compounds can also be obtained according to similar reaction steps.

Synthesis Examples

In the synthesis examples described below, unless otherwise stated, all temperature are in degrees Celsius. Some reagents were purchased from commercial suppliers such as Aldrich Chemical Company, Arco Chemical Company and Alfa Chemical Company, and some intermediates that were not directly purchased were prepared from commercially available raw materials by a simple reaction and were used without further purification unless otherwise stated. The rest of the conventional reagents were purchased from Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd., Qingdao Ocean Chemical Plant and the like. Reactions in the synthesis examples were generally carried out under a positive pressure of nitrogen or argon or an anhydrous solvent was sleeved with a drying tube (unless otherwise stated); and in the reactions, reaction flasks were stoppered with suitable rubber stoppers and substrates were injected into the reaction flasks by a syringe. Each glassware used was dried.

During purification, a chromatographic column was a silica gel column and silica gel (100-200 mesh) was purchased from the Qingdao Ocean Chemical Plant.

In the synthesis examples, low resolution mass spectrometry (MS) data were determined by using Agilent 6120 Quadrupole HPLC-M (column model: Zorbax SB-C18, 2.1× 30 mm, 3.5 μm, 6 min, and a flow rate of 0.6 mL/min). Mobile phase: 5% to 95% (a ratio of (acetonitrile containing 0.1% formic acid) in (water containing 0.1% formic acid), using electrospray ionization (ESI) at 210 nm/254 nm with UV detection.

Nuclear magnetic resonance hydrogen spectrum: Bruker 400 MHz nuclear magnetic resonance spectrometer with $CD_2Cl_2$ as a solvent (in ppm) and TMS (0 ppm) as a reference standard at room temperature.

Synthesis of Intermediate a1-1:

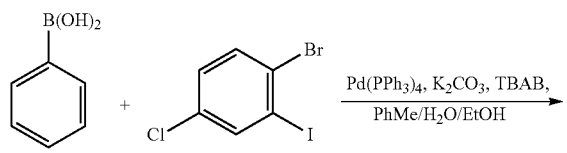

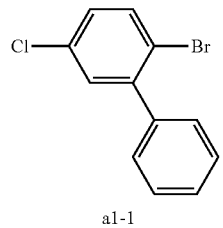

a1-1

2-Bromo-5-chloro-1-iodobenzene (31.22 g; 98.42 mmol), phenylboronic acid (10 g; 82.01 mmol), tetrakis(triphenylphosphine)palladium (0.95 g; 0.82 mmol), potassium carbonate (24.94 g; 180.43 mmol), tetrabutylammonium bromide (2.64 g; 8.20 mmol), toluene (240 mL), ethanol (60 mL) and deionized water (60 mL) were added to a round bottom flask, and heated to 78° C. with stirring under nitrogen atmosphere, and a reaction was carried out for 16 h. The reaction mixture was cooled to room temperature, and washed with water. $Ar_1$ organic phase was separated, and dried over anhydrous magnesium sulfate, filtrated, and the filtrate was concentrated in vacuum to obtain a crude product. A crude product was purified by silica gel column chromatography using dichloromethane/n-heptane as an eluent to obtain an intermediate a1-1 (14.49 g; yield: 66%) as a pale yellow solid.

Intermediate compounds shown in the table below were synthesized by using a method similar to the synthesis of the intermediate a1-1 except that a reactant A in Table 1 below was used instead of phenylboronic acid and a reactant B in Table 1 below was used instead of 2-bromo-5-chloro-1-iodobenzene:

TABLE 1

| Intermediate No. | Reactant A | Reactant B | Product structure | Yield (%) |
|---|---|---|---|---|
| a2-1 | | | | 55 |
| a3-1 | | | | 59 |
| a5-1 | | | | 67 |

TABLE 1-continued

| Intermediate No. | Reactant A | Reactant B | Product structure | Yield (%) |
|---|---|---|---|---|
| a6-1 | phenyl-d5 boronic acid | 1-bromo-3-chloro-5-iodobenzene | 3-bromo-5-chloro-phenyl-d5-benzene | 69 |
| a7-1 | phenylboronic acid | 4-bromo-2-chloro-1-iodobenzene | 4-bromo-2'-chloro-biphenyl | 62 |
| a8-1 | phenyl-d5 boronic acid | 4-bromo-2-chloro-1-iodobenzene | 4-bromo-2-chloro-phenyl-d5-biphenyl | 60 |
| a9-1 | phenylboronic acid | 1-bromo-3-chloro-2-iodobenzene | 2-bromo-6-chloro-biphenyl | 50 |
| a10-1 | phenyl-d5 boronic acid | 1-bromo-3-chloro-2-iodobenzene | 2-bromo-6-chloro-phenyl-d5-biphenyl | 52 |
| a11-1 | phenylboronic acid | 1-bromo-2-chloro-3-iodobenzene | 3-bromo-2-chloro-biphenyl | 61 |

TABLE 1-continued

| Intermediate No. | Reactant A | Reactant B | Product structure | Yield (%) |
|---|---|---|---|---|
| a12-1 | 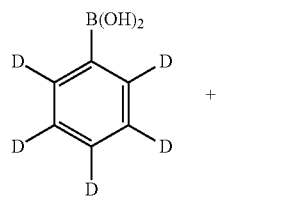 | | | 59 |

Synthesis of Intermediate a1-2:

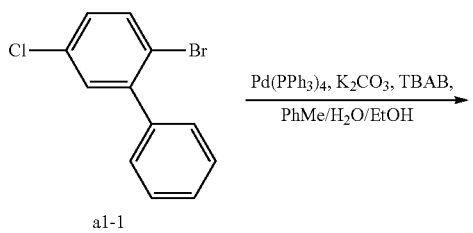

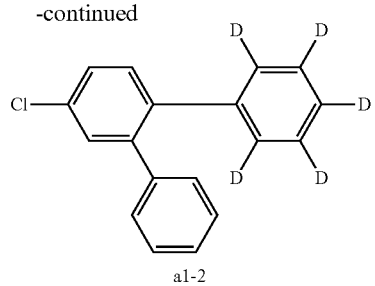

The intermediate a1-1 (10.51 g; 39.37 mmol), deuterated phenylboronic acid (5.0 g; 39.37 mmol), tetrakis(triphenylphosphine)palladium (0.45 g; 0.39 mmol), potassium carbonate (11.97 g; 86.6 mmol), tetrabutylammonium bromide (1.30 g; 3.93 mmol), toluene (80 mL), ethanol (40 mL) and deionized water (20 mL) were added to a round bottom flask, and heated to 78° C. with stirring under nitrogen atmosphere, and a reaction was carried out for 16 h. The reaction mixture was cooled to room temperature, and washed with water. Ar₁ organic phase was separated, and dried over anhydrous magnesium sulfate, filtrated, and the filtrate was concentrated in vacuum to obtain a crude product. A crude product was purified by silica gel column chromatography using dichloromethane/n-heptane as an eluent to obtain a1-2 (7.43 g; yield: 70%).

Intermediate compounds shown in Table 2 below were synthesized by using a method similar to the synthesis of the intermediate a1-2 except that a reactant C in Table 2 below was used instead of deuterated phenylboronic acid and a reactant D in Table 2 below was used instead of a1-1:

TABLE 2

| Intermediate No. | Reactant C | Reactant D | Product structure | Yield (%) |
|---|---|---|---|---|
| a2-2 | | | | 68 |

TABLE 2-continued

| Intermediate No. | Reactant C | Reactant D | Product structure | Yield (%) |
|---|---|---|---|---|
| a3-2 | perdeuterated phenylboronic acid | 2'-bromo-5-chloro-biphenyl (with 4 D on distal ring) | perdeuterated-phenyl–phenyl(4D)–chlorophenyl terphenyl | 66 |
| a4-2 | perdeuterated phenylboronic acid | 2-chloro-5-bromobiphenyl | perdeuterated-phenyl–chlorophenyl–phenyl terphenyl | 73 |
| a7-2 | perdeuterated phenylboronic acid | 3-bromo-5-chloro-biphenyl | perdeuterated-phenyl–(5-chloro-1,3-phenylene)–phenyl terphenyl | 74 |
| a8-2 | perdeuterated phenylboronic acid | 3-bromo-5-chloro-biphenyl (with 4 D on distal ring) | perdeuterated-phenyl–(5-chloro-1,3-phenylene)–perdeuterated-phenyl terphenyl | 72 |

TABLE 2-continued

| Intermediate No. | Reactant C | Reactant D | Product structure | Yield (%) |
|---|---|---|---|---|
| a9-2 | deuterated phenylboronic acid (C6D5-B(OH)2) | 4-bromo-2'-chlorobiphenyl | deuterated terphenyl with Cl substituent | 68 |
| a10-2 | phenylboronic acid | 4-bromo-2-chloro-(2',3',4',5',6'-d5)-biphenyl | terphenyl with Cl and d5-phenyl | 66 |
| a11-2 | (HO)2B-C6D4-D (perdeuterated phenylboronic acid) | 4-bromo-2-chloro-(d5)-biphenyl | perdeuterated terphenyl with Cl | 67 |
| a12-2 | (HO)2B-C6D5 | 2-bromo-1-chloro-3-phenylbenzene | chloro-phenyl-d4-terphenyl product | 62 |

TABLE 2-continued

| Intermediate No. | Reactant C | Reactant D | Product structure | Yield (%) |
|---|---|---|---|---|
| a13-2 | PhB(OH)₂ | 2-chloro-2'-bromo-biphenyl-d5 | 2-chloro-[1,1':2',1''-terphenyl]-d5 | 61 |
| a14-2 | phenyl-d5 boronic acid | 2-chloro-2'-bromo-biphenyl-d4 | chloro-terphenyl-d9 | 60 |
| a15-2 | phenyl-d5 boronic acid | 3-bromo-2-chloro-biphenyl | 2'-chloro-terphenyl-d5 | 63 |
| a16-2 | phenyl-d5 boronic acid | 3'-bromo-2'-chloro-biphenyl-d4 | 2'-chloro-terphenyl-d9 | 65 |

Synthesis of Intermediate a1-3:

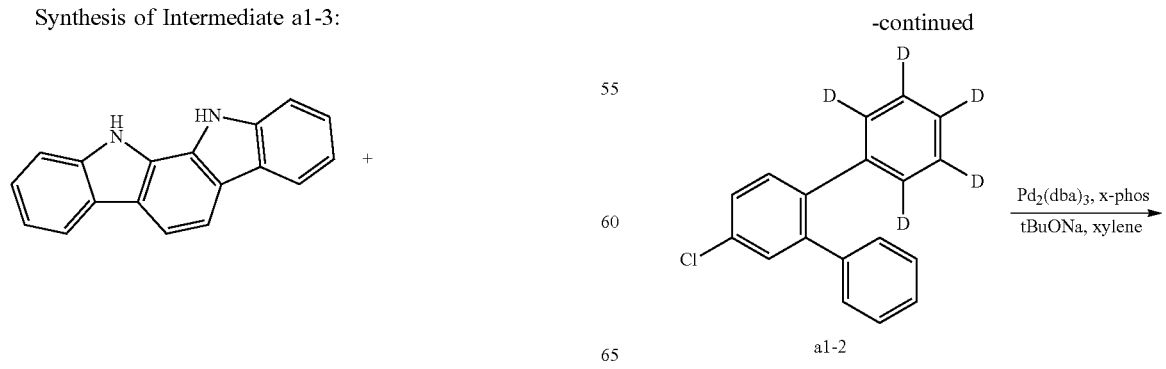

a1-2

-continued

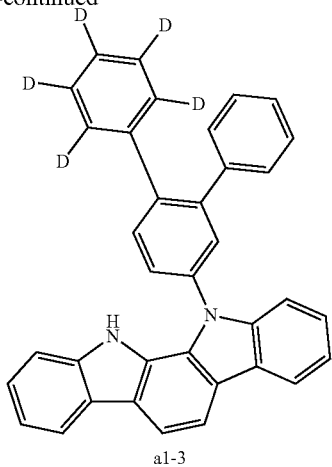

a1-3

Indolo(2,3-A)carbazole (5.0 g; 19.51 mmol), a1-2 (5.26 g; 19.5 mmol), tris(dibenzylideneacetone)dipalladium (0.18 g; 0.20 mmol), X-Phos (CAS: 564483-18-7) (0.16 g; 0.39 mmol), sodium tert-butoxide (2.81 g; 29.26 mmol) and xylene (100 mL) were added to a round bottom flask, and a reaction was carried out under stirring at 135° C. for 16 h under nitrogen atmosphere. After cooled to room temperature, the reaction solution was washed with water, then liquid separation was performed, an separated organic phase was dried over anhydrous magnesium sulfate, filtrated, and the filtrate was concentrated in vacuum to obtain a crude product. A crude product was purified by silica gel column chromatography using dichloromethane/n-heptane as an eluent to obtain a1-3 (7.16 g; yield: 75%).

Intermediate compounds shown in Table 3 below were synthesized by using a method similar to the synthesis of the intermediate a1-3 except that a reactant E in Table 3 below was used instead of a1-2:

TABLE 3

| Intermediate No. | Reactant E | Product structure | Yield (%) |
|---|---|---|---|
| a2-3 | a2-2 | | 76 |
| a3-3 | a3-2 | | 75 |

TABLE 3-continued
| Intermediate No. | Reactant E | Product structure | Yield (%) |
|---|---|---|---|
| a4-3 | 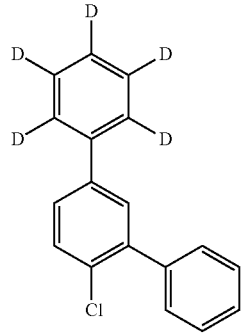 [SMILES: [2H]c1c([2H])c([2H])c(-c2ccc(Cl)c(-c3ccccc3)c2)c([2H])c1[2H]]<br>a4-2 | 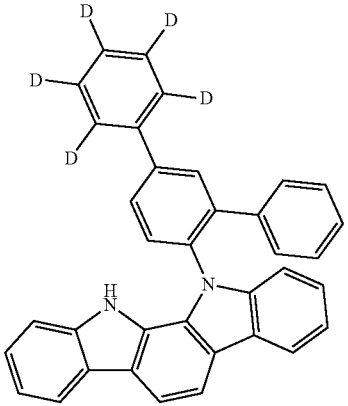 [SMILES: [2H]c1c([2H])c([2H])c(-c2ccc(-n3c4ccccc4c4ccc5c6ccccc6[nH]c5c43)c(-c3ccccc3)c2)c([2H])c1[2H]] | 73 |
| a7-3 | 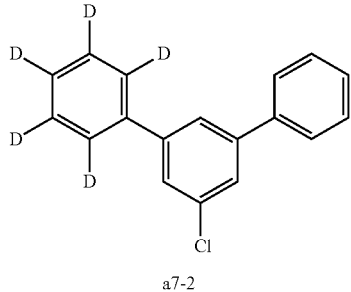 [SMILES: [2H]c1c([2H])c([2H])c(-c2cc(Cl)cc(-c3ccccc3)c2)c([2H])c1[2H]]<br>a7-2 | 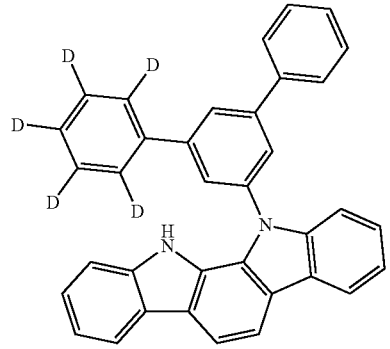 [SMILES: [2H]c1c([2H])c([2H])c(-c2cc(-c3ccccc3)cc(-n3c4ccccc4c4ccc5c6ccccc6[nH]c5c43)c2)c([2H])c1[2H]] | 80 |
| a8-3 | 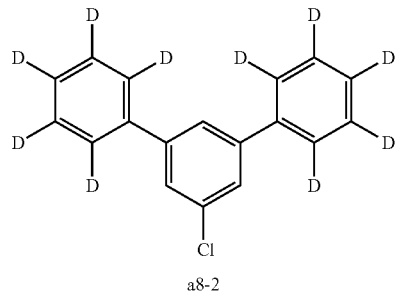 [SMILES: [2H]c1c([2H])c([2H])c(-c2cc(Cl)cc(-c3c([2H])c([2H])c([2H])c([2H])c3[2H])c2)c([2H])c1[2H]]<br>a8-2 | 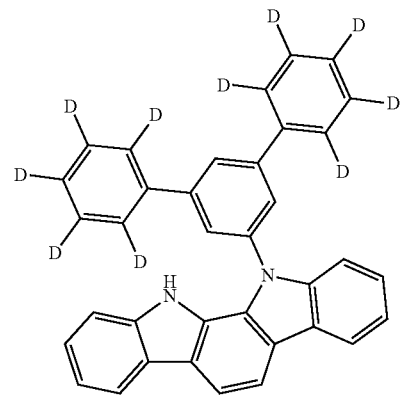 [SMILES: [2H]c1c([2H])c([2H])c(-c2cc(-c3c([2H])c([2H])c([2H])c([2H])c3[2H])cc(-n3c4ccccc4c4ccc5c6ccccc6[nH]c5c43)c2)c([2H])c1[2H]] | 82 |

TABLE 3-continued

| Intermediate No. | Reactant E | Product structure | Yield (%) |
|---|---|---|---|
| a9-3 | a9-2 | | 70 |
| a10-3 | a10-2 | | 73 |
| a11-3 | a11-2 | | 71 |

TABLE 3-continued

| Intermediate No. | Reactant E | Product structure | Yield (%) |
|---|---|---|---|
| a12-3 | a12-2 | | 72 |
| a13-3 | a13-2 | | 70 |
| a14-3 | a14-2 | | 69 |

TABLE 3-continued
| Intermediate No. | Reactant E | Product structure | Yield (%) |
|---|---|---|---|
| a15-3 | a15-2 | | 65 |
| a16-3 | a16-2 | | 62 |
Synthesis of Compound 1:
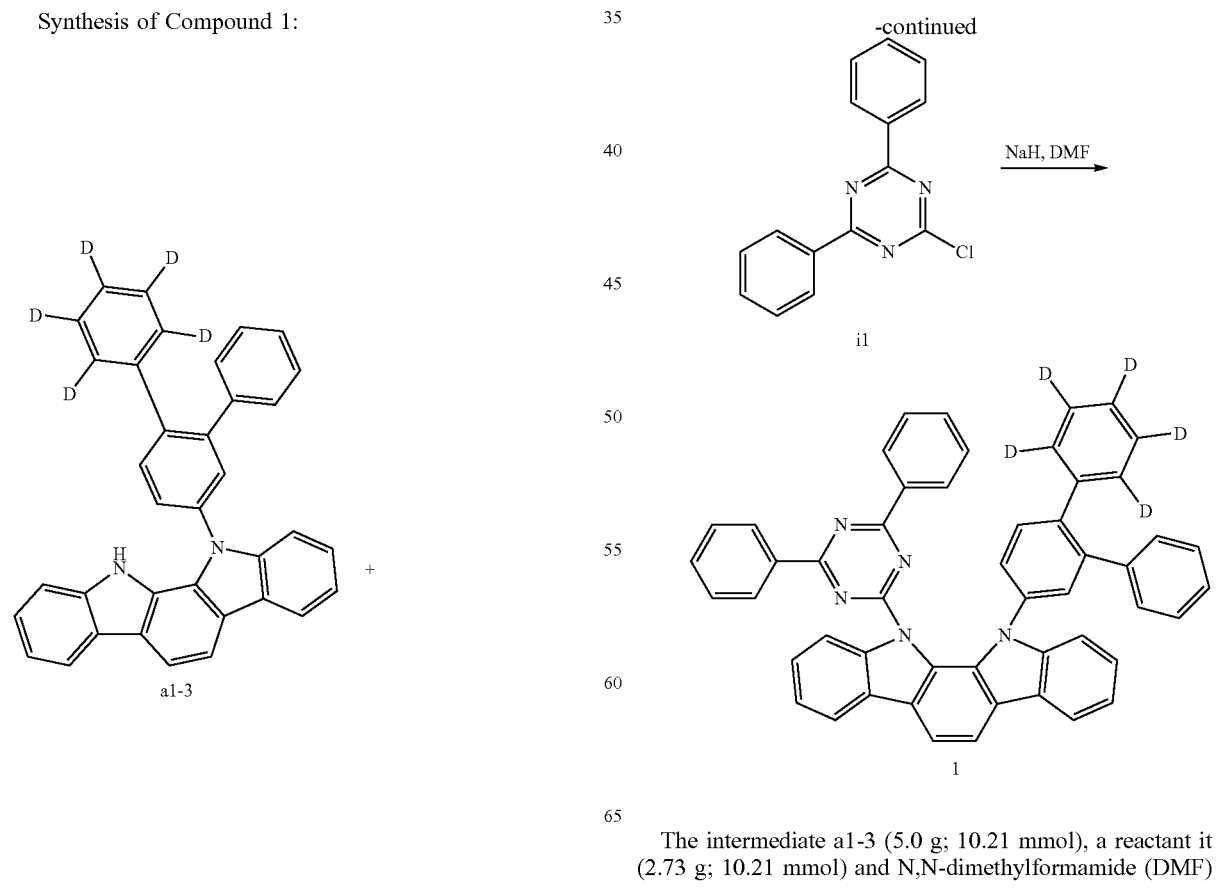
The intermediate a1-3 (5.0 g; 10.21 mmol), a reactant i1 (2.73 g; 10.21 mmol) and N,N-dimethylformamide (DMF)

(50 mL) were added to a round bottom flask, the system temperature was lowered to −5° C. under nitrogen atmosphere, sodium hydride (0.37 g, 15.32 mmol) was then added, and a reaction was continued to be carried out at room temperature for 12 h. The reaction solution was washed with water, liquid separation was performed, an organic phase was dried over anhydrous magnesium sulfate, filtrated, and the filtrate was concentrated in vacuum to obtain a crude product. A crude product was purified by silica gel column chromatography using dichloromethane/n-heptane as an eluent, and was then purified by recrystallization using a toluene/n-heptane solvent system to give a compound 1 (4.4 g; yield: 60%).

Compounds shown in Table 4 below were synthesized by using a method similar to the synthesis of the compound 1 except that a reactant F in Table 4 below was used instead of the intermediate a1-3 and a reactant G in Table 4 below was used instead of the reactant i1:

TABLE 4

| Compound No. | Reactant F | Reactant G | Product structure | Yield (%) |
|---|---|---|---|---|
| 8 | a2-3 | | | 55 |
| 13 | a3-3 | | | 49 |

TABLE 4-continued

| Compound No. | Reactant F | Reactant G | Product structure | Yield (%) |
|---|---|---|---|---|
| 18 | a4-3 | | | 41 |
| 32 | a7-3 | | | 67 |

TABLE 4-continued

| Compound No. | Reactant F | Reactant G | Product structure | Yield (%) |
|---|---|---|---|---|
| 39 | a7-3 | | | 57 |
| 41 | a8-3 | | | 63 |

TABLE 4-continued

| Compound No. | Reactant F | Reactant G | Product structure | Yield (%) |
|---|---|---|---|---|
| 43 | a8-3 | | | 58 |
| 50 | a8-3 | | | 46 |

TABLE 4-continued

| Compound No. | Reactant F | Reactant G | Product structure | Yield (%) |
|---|---|---|---|---|
| 53 | a9-3 | | | 48 |
| 58 | a10-3 | | | 38 |

TABLE 4-continued

| Compound No. | Reactant F | Reactant G | Product structure | Yield (%) |
|---|---|---|---|---|
| 65 | a11-3 | | | 42 |
| 70 | a12-3 | | | 60 |

TABLE 4-continued

| Compound No. | Reactant F | Reactant G | Product structure | Yield (%) |
|---|---|---|---|---|
| 75 | a13-3 | | | 61 |
| 78 | a14-3 | | | 50 |

TABLE 4-continued

| Compound No. | Reactant F | Reactant G | Product structure | Yield (%) |
|---|---|---|---|---|
| 85 | a15-3 | | | 60 |
| 90 | a16-3 | | | 44 |

TABLE 4-continued
| Compound No. | Reactant F | Reactant G | Product structure | Yield (%) |
|---|---|---|---|---|
| 93 | 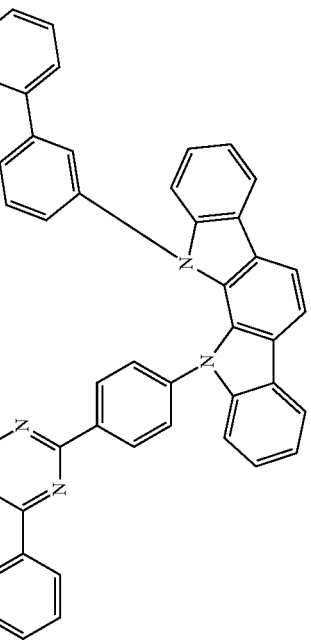 | 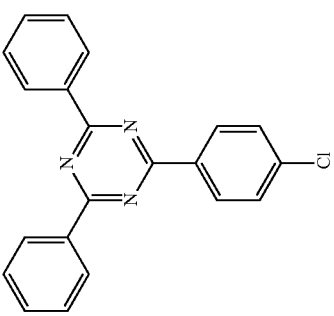 | 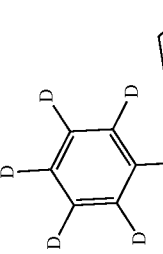 | 42 |

Mass spectrum data for the compounds are shown in Table 5:

TABLE 5

| Compound | m/z |
|---|---|
| Compound 1 | m/z = 721.3 (M + H)⁺ |
| Compound 13 | m/z = 815.4 (M + H)⁺ |
| Compound 32 | m/z = 797.3 (M + H)⁺ |
| Compound 39 | m/z = 873.3 (M + H)⁺ |
| Compound 43 | m/z = 802.4 (M + H)⁺ |
| Compound 53 | m/z = 797.3 (M + H)⁺ |
| Compound 65 | m/z = 852.4 (M + H)⁺ |
| Compound 75 | m/z = 739.2 (M + H)⁺ |
| Compound 85 | m/z = 822.3 (M + H)⁺ |
| Compound 93 | m/z = 797.3 (M + H)⁺ |
| Compound 8 | m/z = 771.3 (M + H)⁺ |
| Compound 18 | m/z = 821.3 (M + H)⁺ |
| Compound 41 | m/z = 726.3 (M + H)⁺ |
| Compound 50 | m/z = 876.4 (M + H)⁺ |
| Compound 58 | m/z = 847.3 (M + H)⁺ |
| Compound 70 | m/z = 855.4 (M + H)⁺ |
| Compound 78 | m/z = 842.3 (M + H)⁺ |
| Compound 90 | m/z = 964.4 (M + H)⁺ |

¹HNMR Data for a Compound 43:

¹HNMR (400 MHZ, $CD_2Cl_2$): δ 8.59-8.66 (d, 1H), δ 8.33-8.39 (d, 1H), δ 8.22-8.33 (m, 5H), δ 8.17-8.22 (d, 1H), δ 8.10-8.17 (d, 1H), δ 7.58-7.68 (m, 3H), δ 7.43-7.58 (m, 7H), δ 7.31-7.43 (m, 5H), δ 7.17-7.31 (m, 3H).

Manufacture and Performance Evaluation of Organic Electroluminescent Device

Example 1

Green Organic Electroluminescent Device $Ar_1$ anode was formed of indium tin oxide (ITO) with a thickness of 1500 Å on a substrate where a reflective layer was formed, and the substrate was cut into a size of 40 mm×40 mm×0.7 mm, and prepared into an experimental substrate with cathode, anode, and insulating layer patterns by using a photoetching process, and the surface of the ITO substrate was cleaned with an organic solvent to remove impurities on the surface; and surface treatment was performed by utilizing ultraviolet ozone and $O_2:N_2$ plasma to increase the work function of the anode.

CuPC was vacuum evaporated on the substrate anode by a physical vapor deposition (PVD) method to form a hole injection layer with a thickness of 100 Å, and HT-01 having a thickness of 1230 Å was evaporated on the hole injection layer to form a hole transport layer.

HT-02 with a thickness of 300 Å was evaporated on the hole transport layer to form a hole auxiliary layer.

A compound 1, GH-P and Ir(ppy)₃ were co-evaporated on the hole auxiliary layer at an evaporation ratio of 45%:45%:10% to form an organic luminescent layer (a green organic luminescent layer) with a thickness of 320 Å.

ET-01 and LiQ were evaporated at an evaporation ratio of 1:1 to form an electron transport layer with a thickness of 330 Å, Yb was evaporated on the electron transport layer to form an electron injection layer with a thickness of 10 Å, and magnesium and silver were co-evaporated on the electron injection layer at an evaporation ratio of 1:9 to form a cathode with a thickness of 130 Å.

In addition, CP-01 with a thickness of 600 Å was evaporated on the cathode to form an organic capping layer (CPL), thus enabling the manufacture of an organic luminescent device.

Examples 2 to 18

An organic electroluminescent device was manufactured by the same method as that in Example 1 by replacing the compound 1 in Example 1 with compounds shown in Table 7, respectively, when forming an organic luminescent layer.

Comparative Example 1

An organic electroluminescent device was manufactured by the same method as that in Example 1 except that a compound I was used instead of the compound 1 in Example 1 when forming an organic luminescent layer.

Comparative Example 2

An organic electroluminescent device was manufactured by the same method as that in Example 1 except that a compound II was used instead of the compound 1 in Example 1 when forming an organic luminescent layer.

Comparative Example 3

An organic electroluminescent device was manufactured by the same method as that in Example 1 except that a compound III was used instead of the compound 1 in Example 1 when forming an organic luminescent layer.

Comparative Example 4

An organic electroluminescent device was manufactured by the same method as that in Example 1 except that a compound IV was used instead of the compound 1 in Example 1 when forming an organic luminescent layer.

Comparative Example 5

An organic electroluminescent device was manufactured by the same method as that in Example 1 except that a compound V was used instead of the compound 1 in Example 1 when forming an organic luminescent layer.

Comparative Example 6

An organic electroluminescent device was manufactured by the same method as that in Example 1 except that a compound VI was used instead of the compound 1 in Example 1 when forming an organic luminescent layer.

The structures of main materials used in Examples 1 to 18 and Comparative examples 1 to 6 are shown in Table 6 below:

TABLE 6
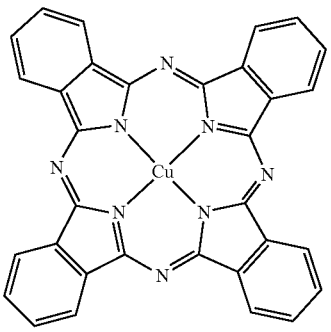
CuPC
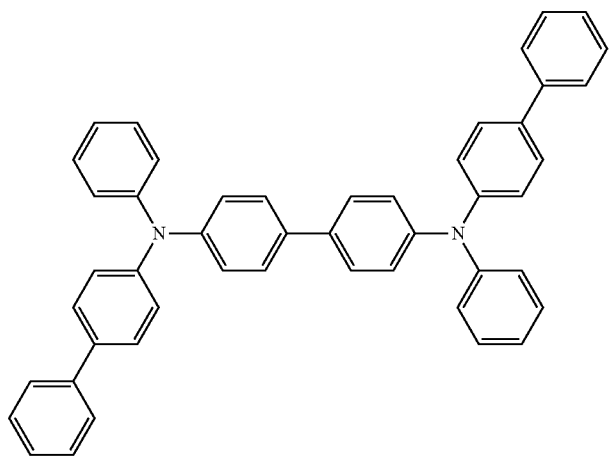 [SMILES: c1ccc(-c2ccc(N(c3ccccc3)c3ccc(-c4ccc(N(c5ccccc5)c5ccc(-c6ccccc6)cc5)cc4)cc3)cc2)cc1]
HT-01
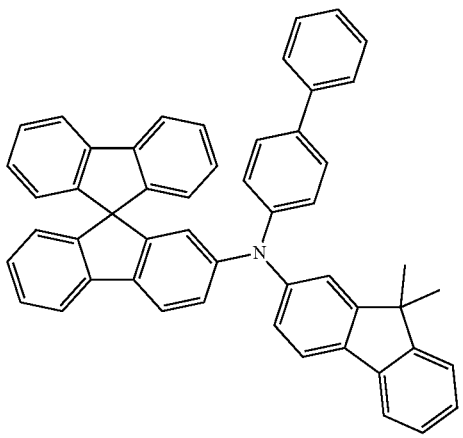 [SMILES: CC1(C)c2ccccc2-c2ccc(N(c3ccc(-c4ccccc4)cc3)c3ccc4c(c3)C3(c5ccccc5-c5ccccc53)c3ccccc3-4)cc21]
HT-02
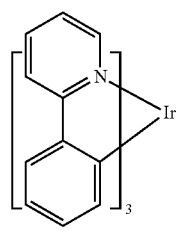
Ir(ppy)$_3$ TABLE 6-continued
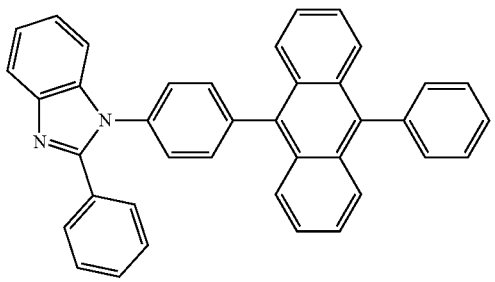 [SMILES: c1ccc(-c2c3ccccc3c(-c3ccc(-n4c(-c5ccccc5)nc5ccccc54)cc3)c3ccccc23)cc1]
ET-01
LiQ
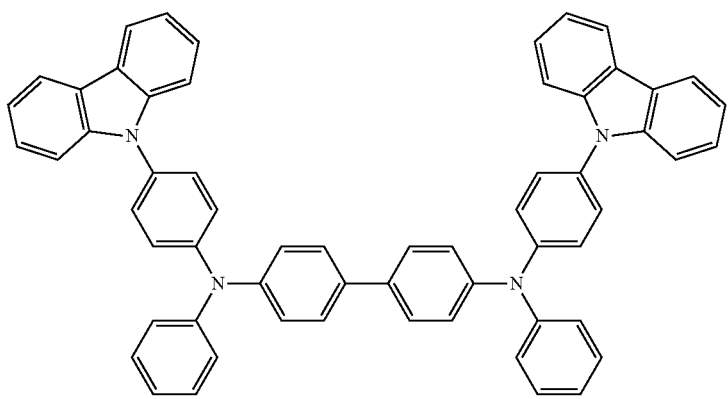 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-01
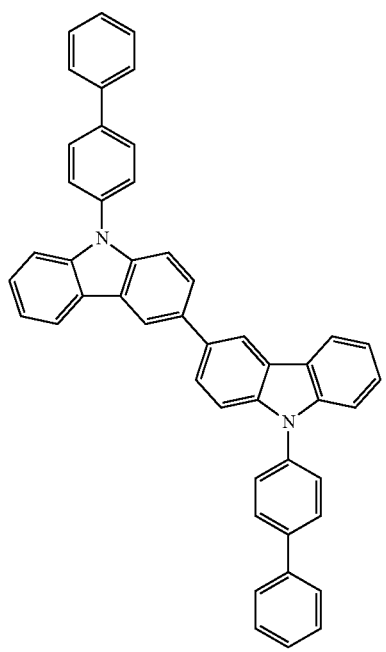 [SMILES: c1ccc(-c2ccc(-n3c4ccccc4c4cc(-c5ccc6c(c5)c5ccccc5n6-c5ccc(-c6ccccc6)cc5)ccc43)cc2)cc1]

TABLE 6-continued
GH-P
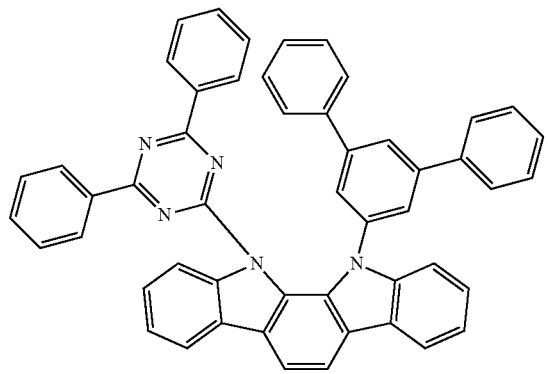 [SMILES: c1ccc(-c2cc(-c3ccccc3)cc(-n3c4ccccc4c4ccc5c6ccccc6n(-c6nc(-c7ccccc7)nc(-c7ccccc7)n6)c5c43)c2)cc1]
Compound I
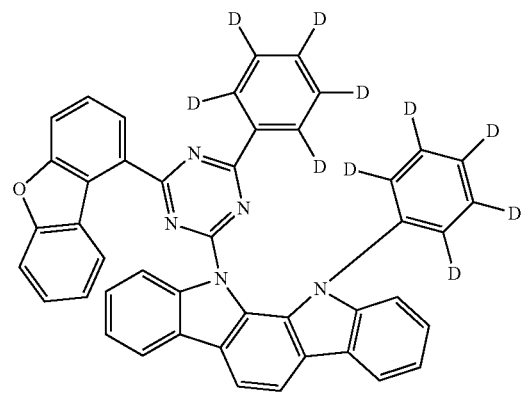 [SMILES: [2H]c1c([2H])c([2H])c(-c2nc(-c3cccc4oc5ccccc5c34)nc(-n3c4ccccc4c4ccc5c6ccccc6n(-c6c([2H])c([2H])c([2H])c([2H])c6[2H])c5c43)n2)c([2H])c1[2H]]
Compound II
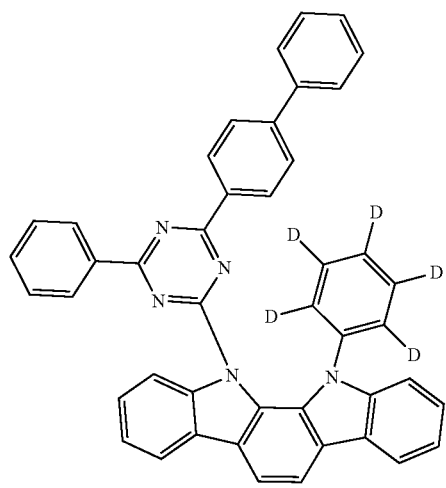 [SMILES: [2H]c1c([2H])c([2H])c(-n2c3ccccc3c3ccc4c5ccccc5n(-c5nc(-c6ccccc6)nc(-c6ccc(-c7ccccc7)cc6)n5)c4c32)c([2H])c1[2H]]
Compound III TABLE 6-continued
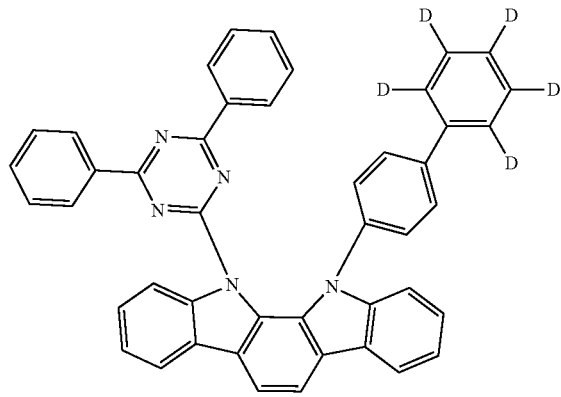 [SMILES: [2H]c1c([2H])c([2H])c(-c2ccc(-n3c4ccccc4c4ccc5c6ccccc6n(-c6nc(-c7ccccc7)nc(-c7ccccc7)n6)c5c43)cc2)c([2H])c1[2H]]
Compound IV
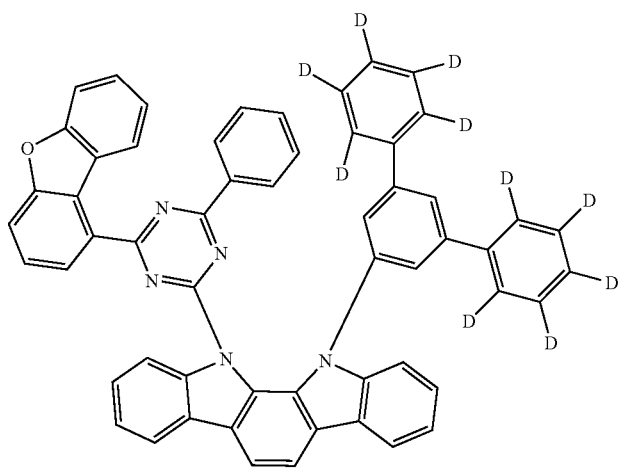 [SMILES: [2H]c1c([2H])c([2H])c(-c2cc(-c3c([2H])c([2H])c([2H])c([2H])c3[2H])cc(-n3c4ccccc4c4ccc5c6ccccc6n(-c6nc(-c7ccccc7)nc(-c7cccc8oc9ccccc9c78)n6)c5c43)c2)c([2H])c1[2H]]
Compound V
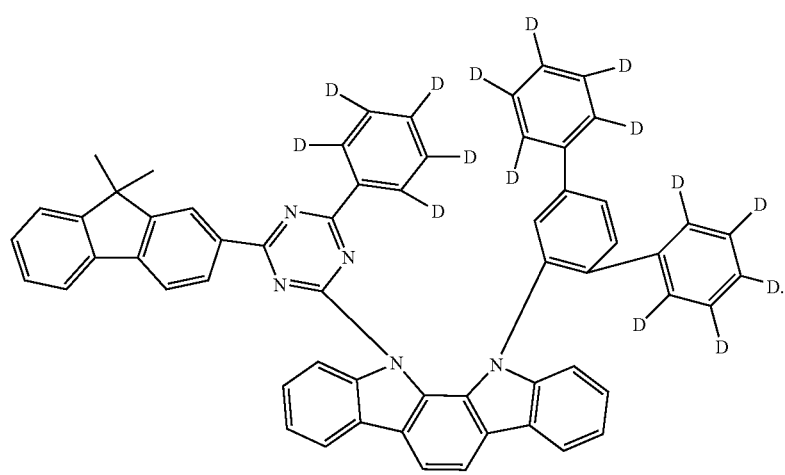
Compound VI
For the organic electroluminescent devices manufactured above, the current-voltage-brightness (IVL) performance of the devices was analyzed under the condition of 20 mA/cm 2, the T95 service life was tested under the condition of 15 mA/cm 2, and the results are shown in Table 7 below:

TABLE 7

| Example No. | Compound | Driving voltage (V) | Current efficiency (Cd/A) | Power efficiency (lm/W) | Chromaticity coordinate CIEx | Chromaticity coordinate CIEy | External quantum efficiency EQE (%) | T95 service life (h) 15 mA/cm$^2$ |
|---|---|---|---|---|---|---|---|---|
| Example 1 | 1 | 4.14 | 83.5 | 63.3 | 0.220 | 0.730 | 20.0 | 270 |
| Example 2 | 8 | 4.12 | 83.1 | 63.4 | 0.220 | 0.730 | 20.0 | 282 |
| Example 3 | 13 | 4.14 | 85.3 | 64.7 | 0.220 | 0.730 | 20.5 | 278 |
| Example 4 | 18 | 4.18 | 86.1 | 64.7 | 0.220 | 0.730 | 20.7 | 282 |
| Example 5 | 32 | 4.10 | 98.6 | 69.6 | 0.220 | 0.730 | 20.1 | 268 |
| Example 6 | 39 | 4.16 | 99.7 | 70.2 | 0.220 | 0.730 | 20.1 | 257 |
| Example 7 | 41 | 4.12 | 98.0 | 72.6 | 0.220 | 0.730 | 20.6 | 269 |
| Example 8 | 43 | 4.12 | 99.3 | 69.8 | 0.220 | 0.730 | 19.8 | 258 |
| Example 9 | 50 | 4.10 | 94.4 | 70.1 | 0.220 | 0.730 | 20.2 | 262 |
| Example 10 | 53 | 4.12 | 82.5 | 62.3 | 0.220 | 0.730 | 19.8 | 282 |
| Example 11 | 58 | 4.13 | 83.4 | 63.5 | 0.220 | 0.730 | 20.0 | 273 |
| Example 12 | 65 | 4.12 | 82.8 | 62.5 | 0.220 | 0.730 | 19.9 | 271 |
| Example 13 | 70 | 4.10 | 83.0 | 62.0 | 0.220 | 0.730 | 19.9 | 257 |
| Example 14 | 75 | 4.13 | 84.1 | 63.3 | 0.220 | 0.730 | 20.2 | 265 |
| Example 15 | 78 | 4.13 | 83.4 | 62.8 | 0.220 | 0.730 | 20.0 | 271 |
| Example 16 | 85 | 4.11 | 83.4 | 63.7 | 0.220 | 0.730 | 20.0 | 262 |
| Example 17 | 90 | 4.11 | 82.5 | 61.9 | 0.220 | 0.730 | 19.8 | 262 |
| Example 18 | 93 | 4.36 | 83.2 | 63.3 | 0.220 | 0.730 | 20.0 | 258 |
| Comparative example 1 | Compound I | 4.40 | 66.6 | 46.5 | 0.220 | 0.730 | 16.0 | 189 |
| Comparative example 2 | Compound II | 4.48 | 70.1 | 50.3 | 0.220 | 0.730 | 16.8 | 197 |
| Comparative example 3 | Compound III | 4.45 | 71.2 | 51.4 | 0.220 | 0.730 | 17.1 | 205 |
| Comparative example 4 | Compound IV | 4.46 | 73.2 | 51.4 | 0.220 | 0.730 | 17.1 | 221 |
| Comparative example 5 | Compound V | 4.43 | 74.1 | 51.7 | 0.220 | 0.730 | 17.6 | 223 |
| Comparative example 6 | Compound VI | 4.41 | 72.6 | 51.5 | 0.220 | 0.730 | 17.4 | 212 |

From the data shown in Table 7 above, it can be seen that the organic electroluminescent devices manufactured in Examples 1 to 18 have properties of significantly high luminous efficiency and longer service life compared with Comparative examples 1 to 6.

The luminous efficiency (Cd/A) of the organic electroluminescent devices manufactured in Examples 1 to 18 was improved by at least 11.3%; and the T95 service life of the devices was improved by at least 15.2% compared with Comparative examples 1 to 6.

According to the nitrogen-containing compound of the present disclosure, the use of perdeuteration on phenyl of diphenyl-substituted phenyl, in conjunction with a diaryl-substituted triazinyl, improves the compactness of the molecular structure, reduces the molecular volume, and thus improves the carrier mobility and exciton recombination efficiency, thus greatly improving the luminous efficiency and service life performance of the device; and the compounds II to VI have deuterated phenyl and a triazinyl structure as well, but compared with the combination of diphenyl-substituted phenyl and a diaryltriazinyl used in the present disclosure, the resulting steric conjugation effect is insufficient, and the resulting electron mobility improvement is poor, so that the device performance is not significantly improved. In the compound V, triazinyl has a heteroaryl substituent, which has a weaker hyperconjugation effect with diphenyl-substituted benzenyl than diaryl-substituted triazinyl. While in the compound VI, aryl on triazinyl has a plurality of deuterium substituents, so that the crystallinity of the compound is improved, and the film-forming property is poor, affecting the improvement of the service life of the device.

Thus, when the novel compound of the present disclosure is used for manufacturing a green organic electroluminescent device, the luminous efficiency of the organic electroluminescent device can be effectively improved, the voltage can be reduced, and the service life of the organic electroluminescent device can be prolonged.

What is claimed is:

1. A nitrogen-containing compound, having a structure as shown in a formula 1:

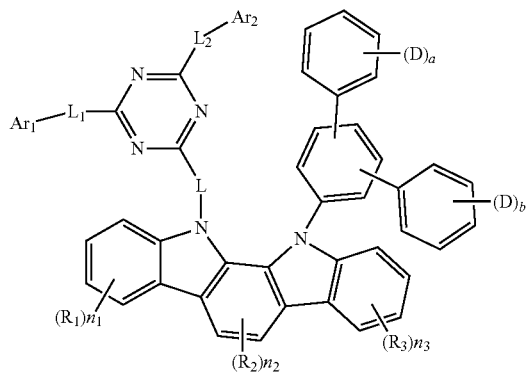

Formula 1 wherein L is selected from a single bond or

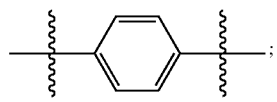 [SMILES: *c1ccc(*)cc1]

$L_1$ and $L_2$ are each independently selected from a single bond, substituted or unsubstituted phenylene, substituted or unsubstituted naphthylene, or substituted or unsubstituted biphenylene; and substituents in the $L_1$ and the $L_2$ are each independently selected from fluorine, cyano, methyl, ethyl, n-propyl, isopropyl or tert-butyl;

$Ar_1$ and $Ar_1$ are each independently selected from substituted or unsubstituted phenyl, substituted or unsubstituted naphthyl, substituted or unsubstituted biphenyl, substituted or unsubstituted phenanthryl, substituted or unsubstituted fluorenyl, substituted or unsubstituted terphenyl, substituted or unsubstituted triphenylene, or substituted or unsubstituted spirobifluorenyl; and substituents in the $Ar_1$ and the $Ar_2$ are each independently selected from fluorine, cyano, methyl, ethyl, n-propyl, isopropyl, tert-butyl, trifluoromethyl, adamantyl or phenyl;

a is 5, b is selected from 0 or 5;

each $R_1$, each $R_2$, and each $R_3$ are each independently hydrogen;

$n_1$ represents the number of $R_1$, $n_1$ is selected from 1, 2 or 3;

$n_2$ represents the number of $R_2$, $n_2$ is selected from 1 or 2; and $n_3$ represents the number of $R_3$, $n_3$ is selected from 1, 2, 3 or 4.

2. The nitrogen-containing compound according to claim 1, wherein $Ar_1$ and $Ar_2$ are each independently selected from the group consisting of:

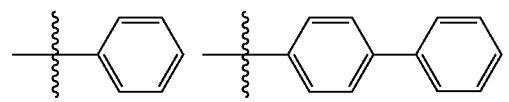

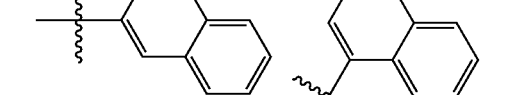

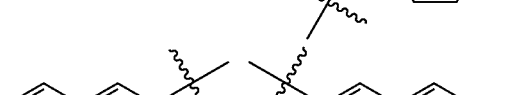

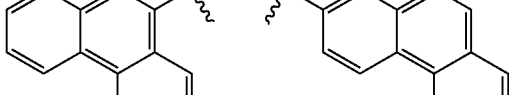

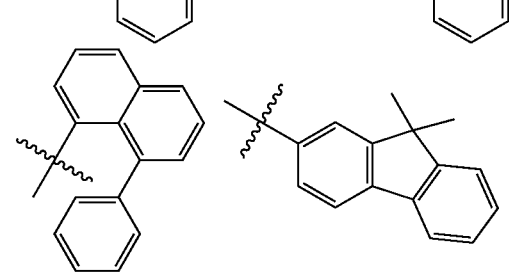

-continued

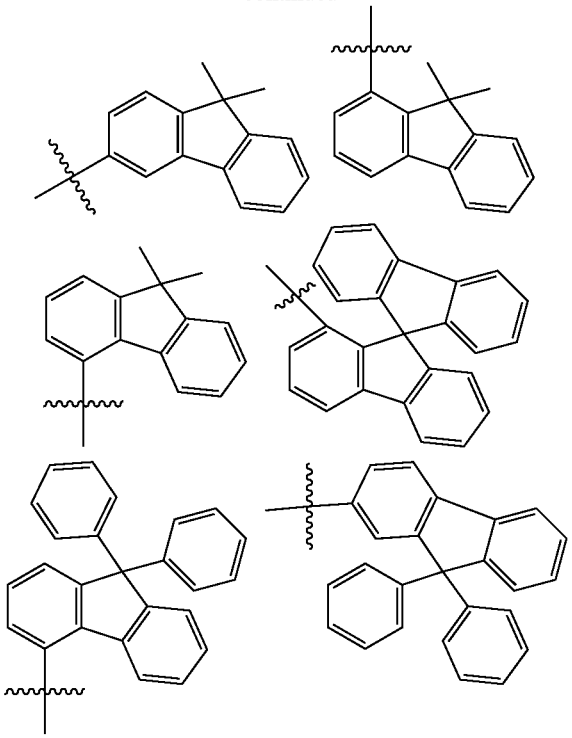

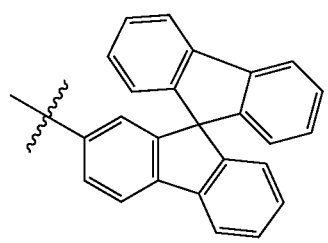

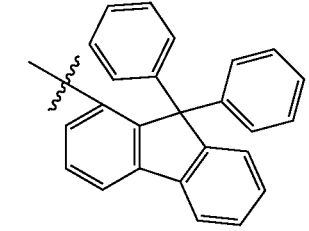

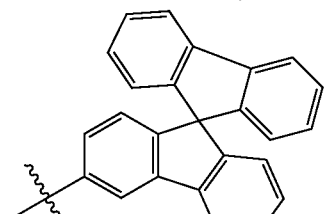

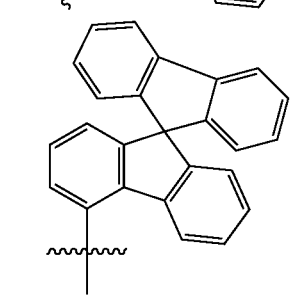

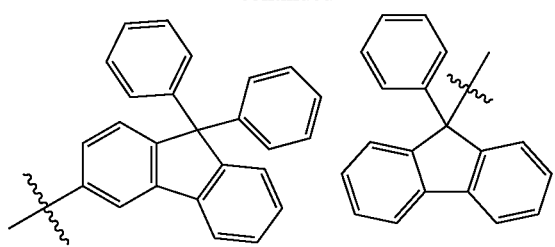
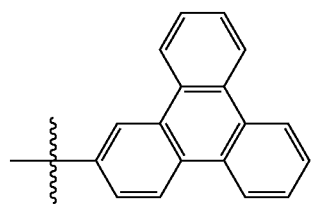
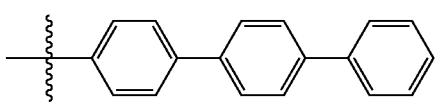
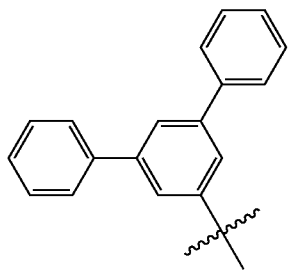
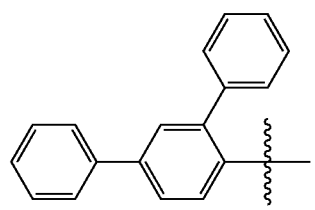
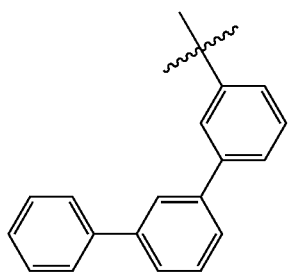
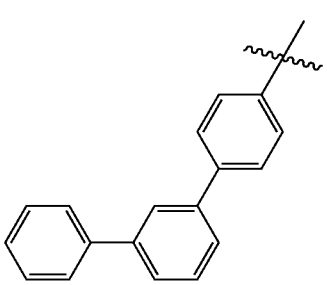
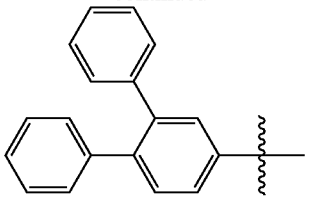
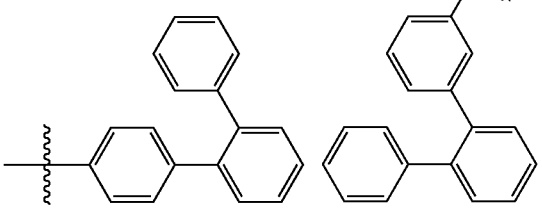
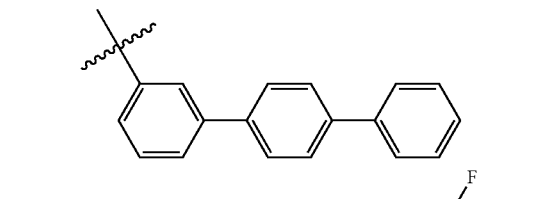
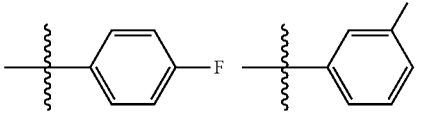
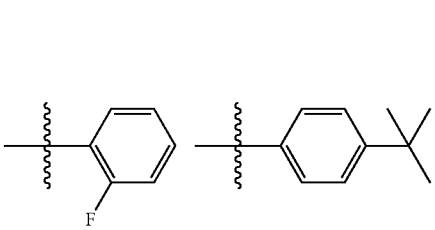
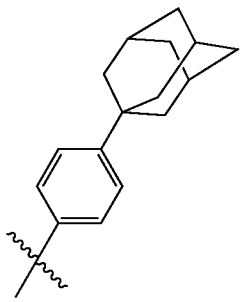
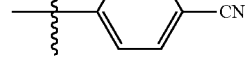
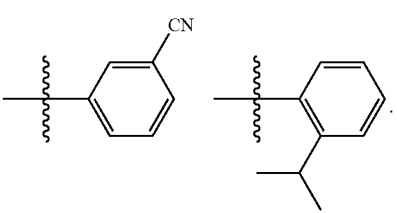
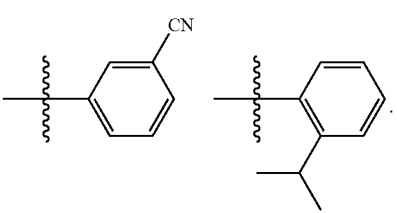

3. The nitrogen-containing compound according to claim 1, wherein

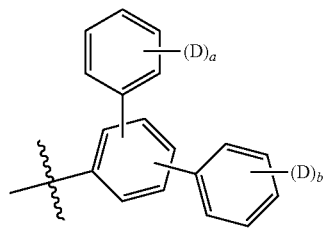

in the formula 1 is selected from the following structures:

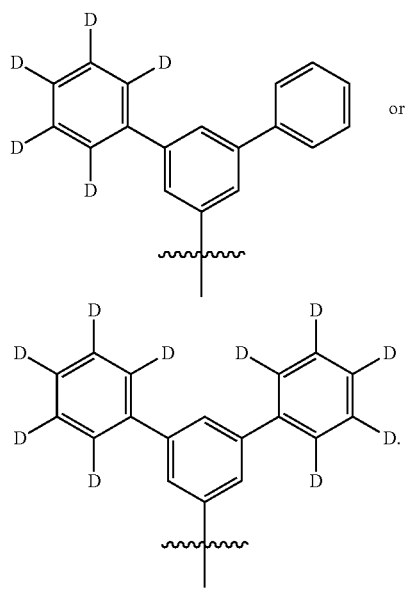

4. The nitrogen-containing compound according to claim 1, wherein Ar₁ and Ar₂ are each independently selected from the group consisting of:

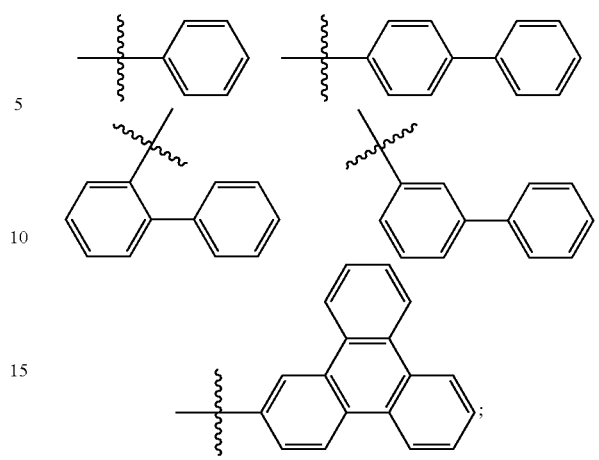

L is a single bond; and
L₁ and L₂ are each independently selected from a single bond or the group consisting of:

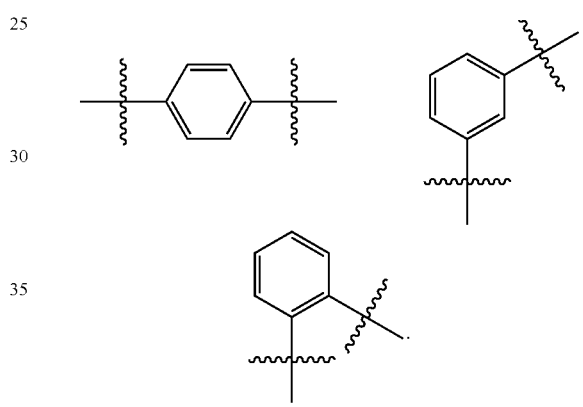

5. The nitrogen-containing compound according to claim 1, wherein the nitrogen-containing compound is selected from the group consisting of:

1

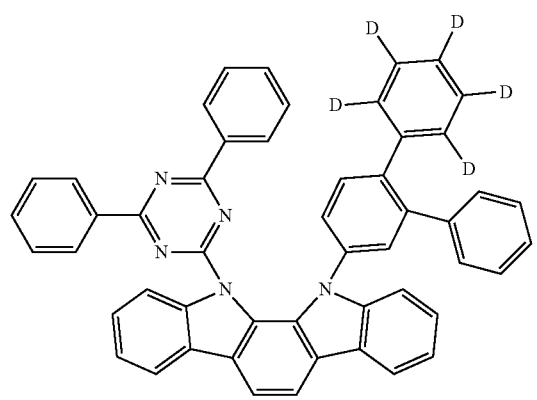

2

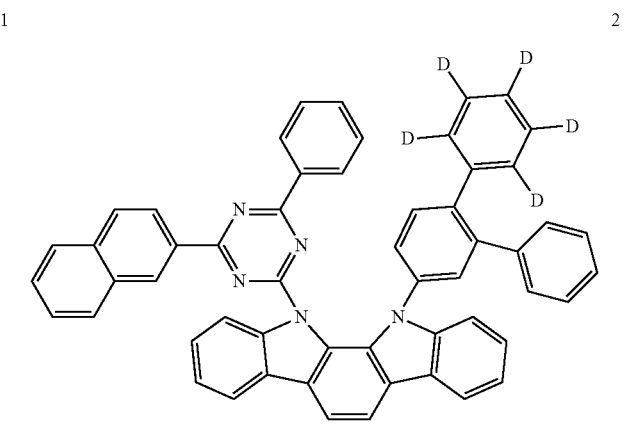

-continued
3
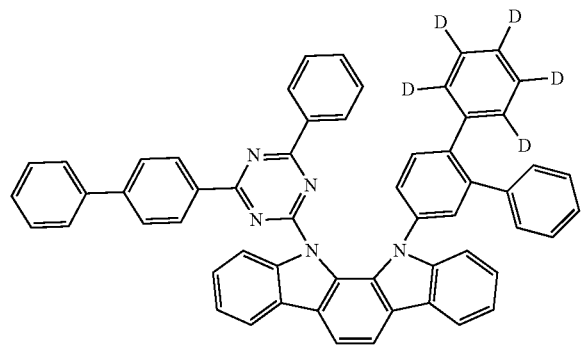
4
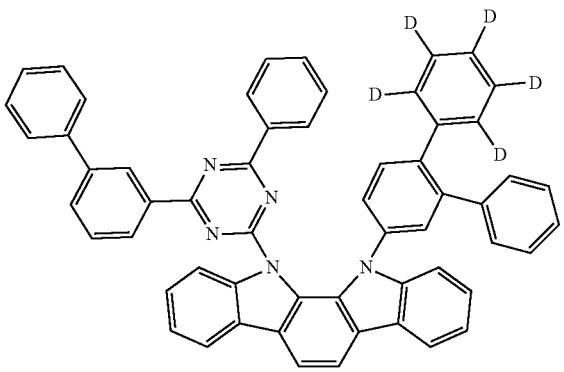
5
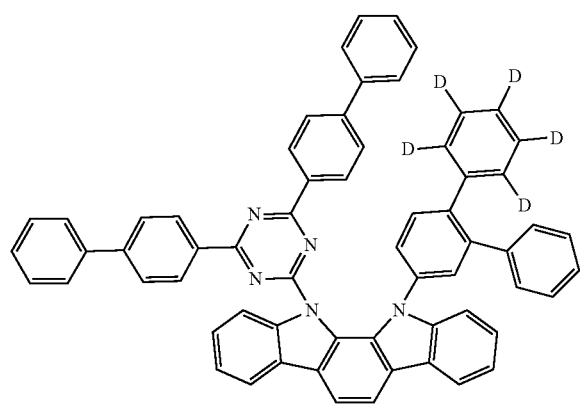
6
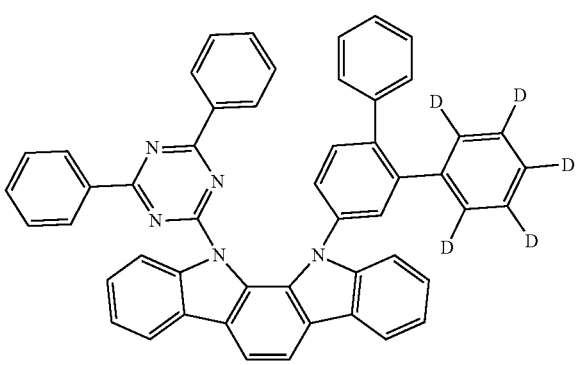
7
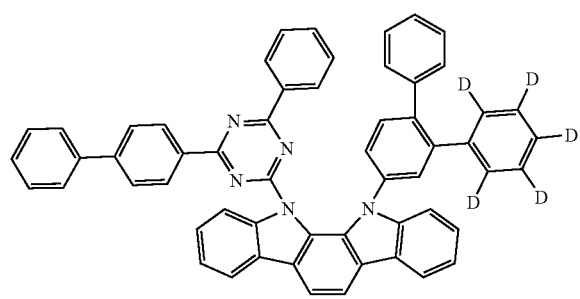
8
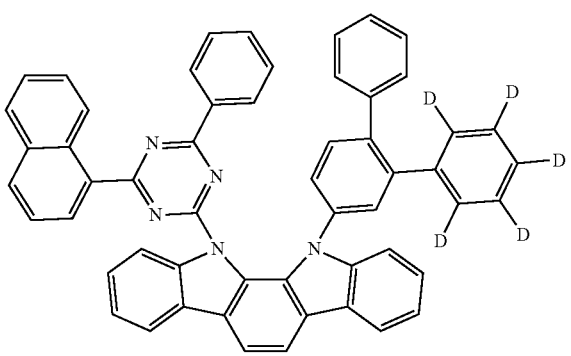
11
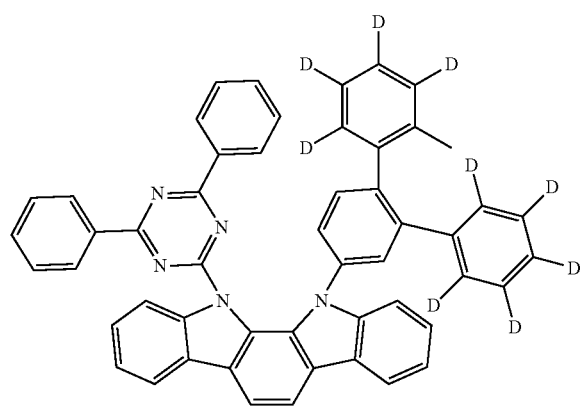
12
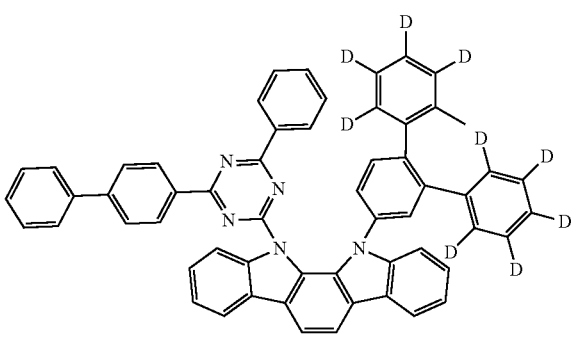

-continued
13
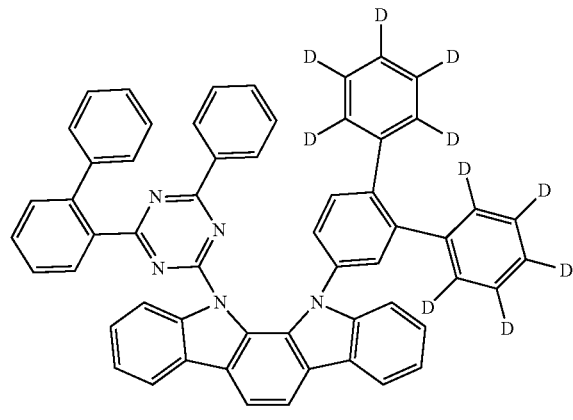
16
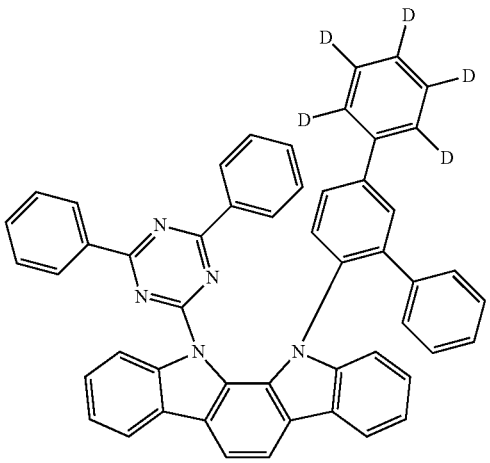
17
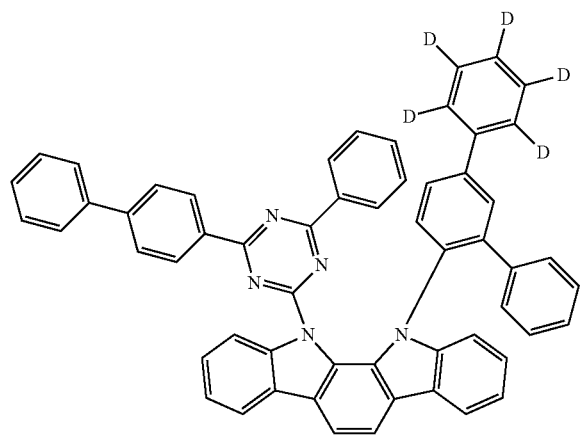
18
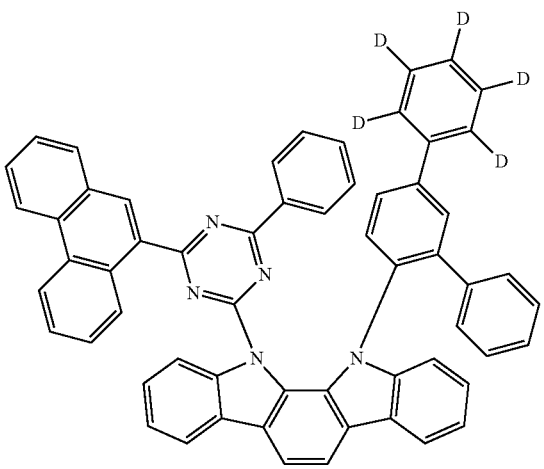
19
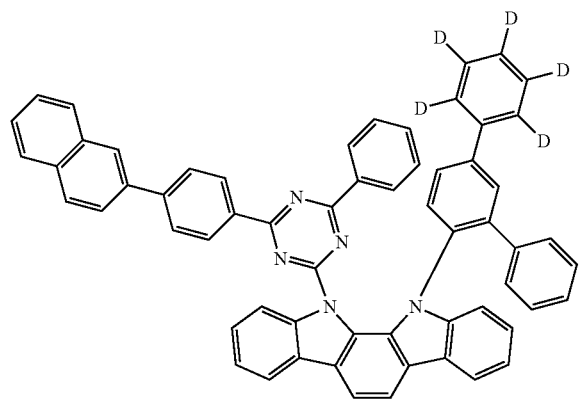
21
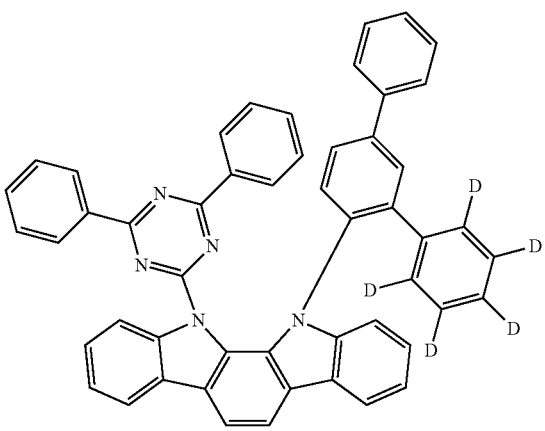

22
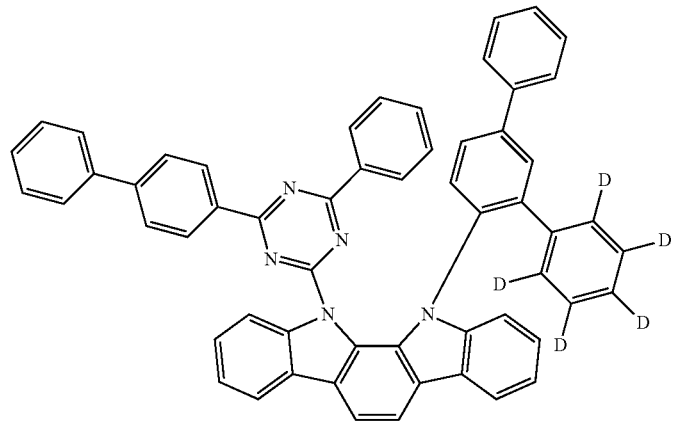
24
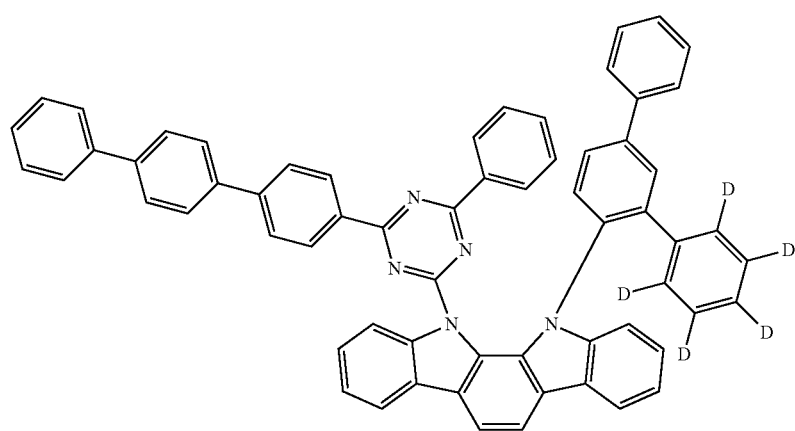
31
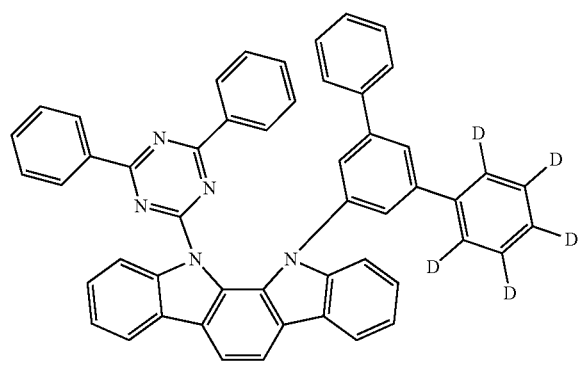
32
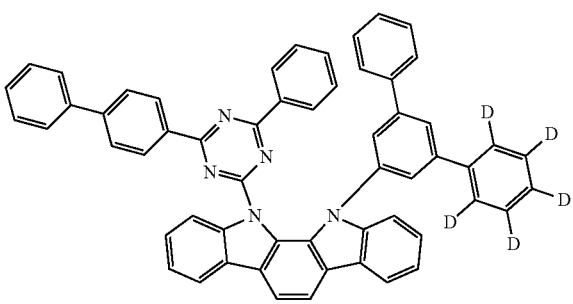

-continued
25
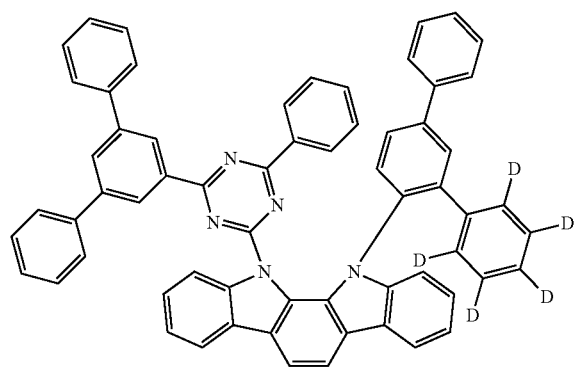
26
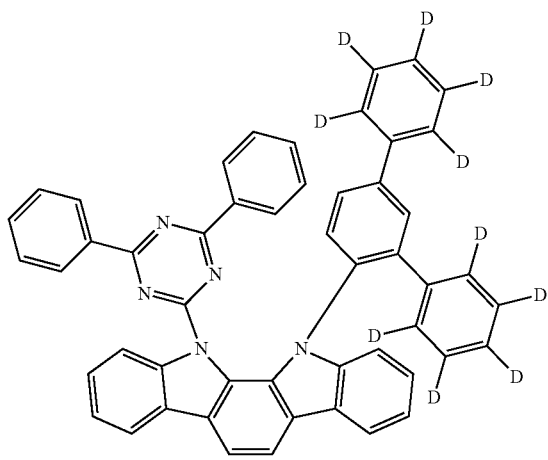
27
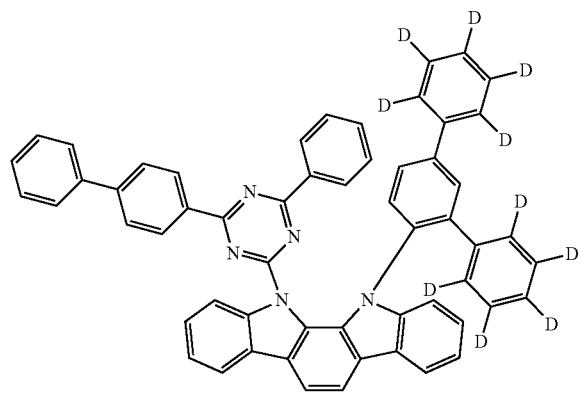
28
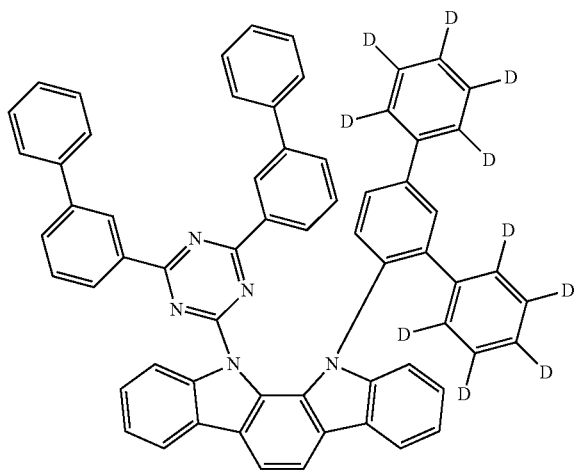
33
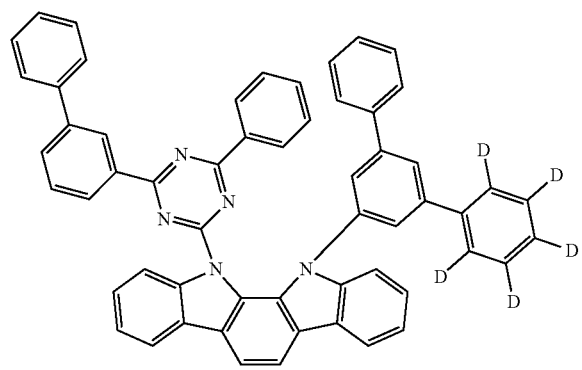
36
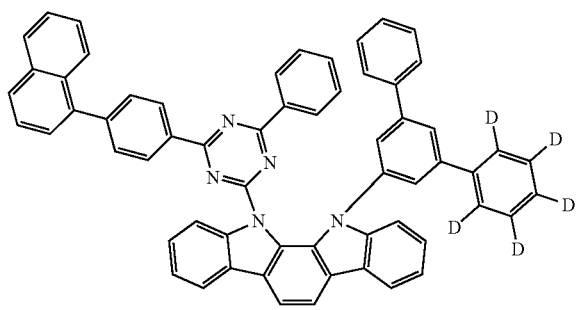

38
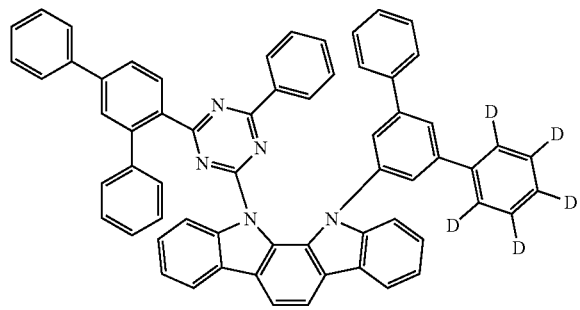
39
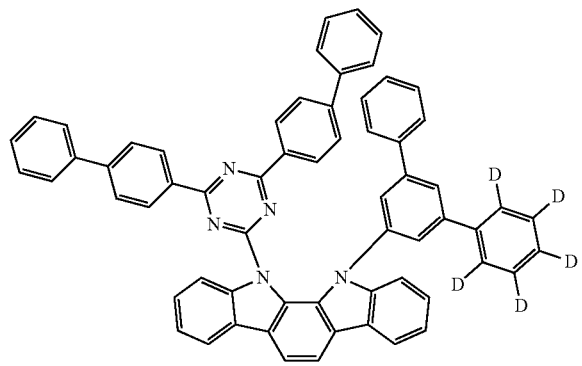
41
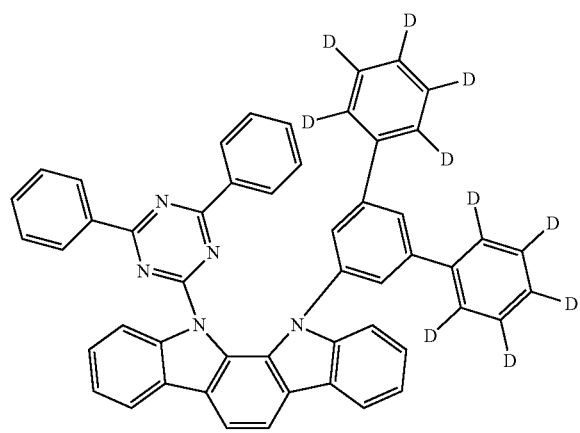
42
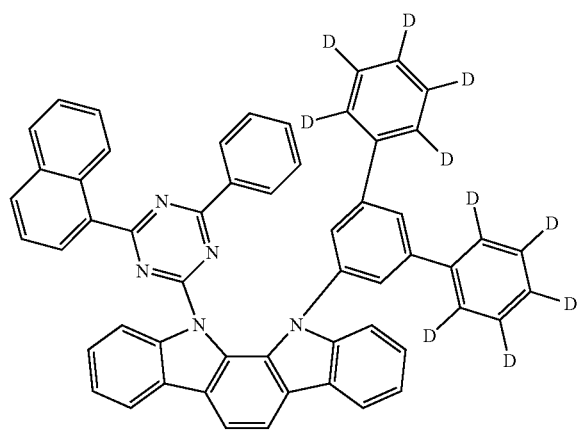
43
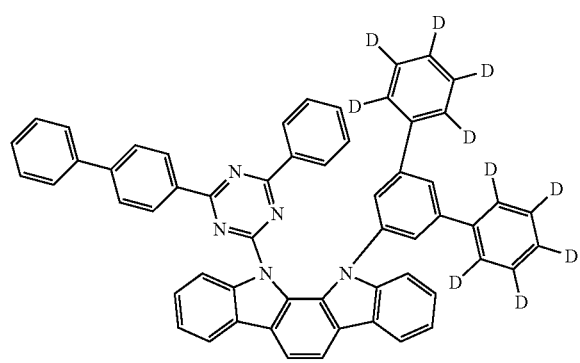
44
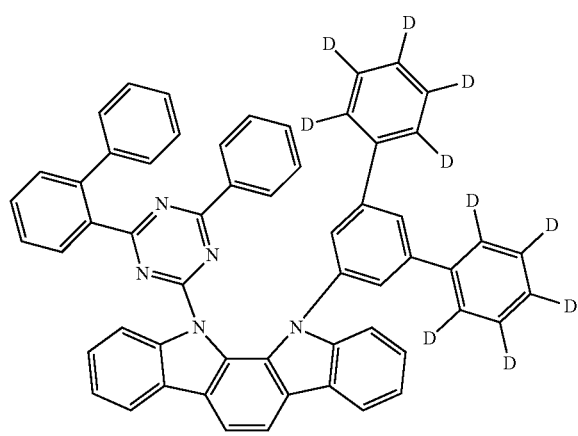

47
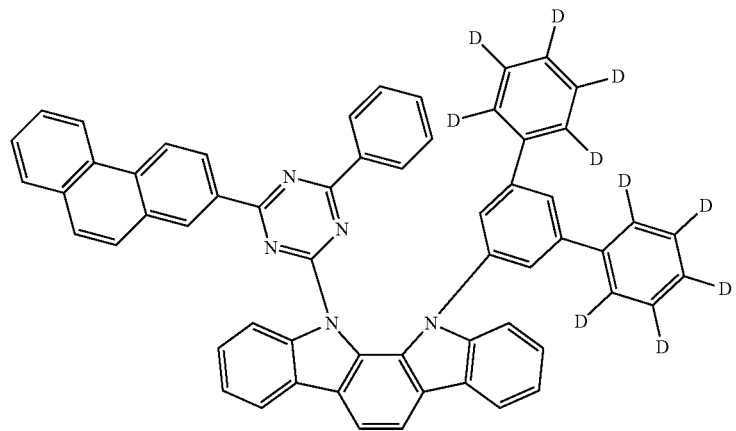
48
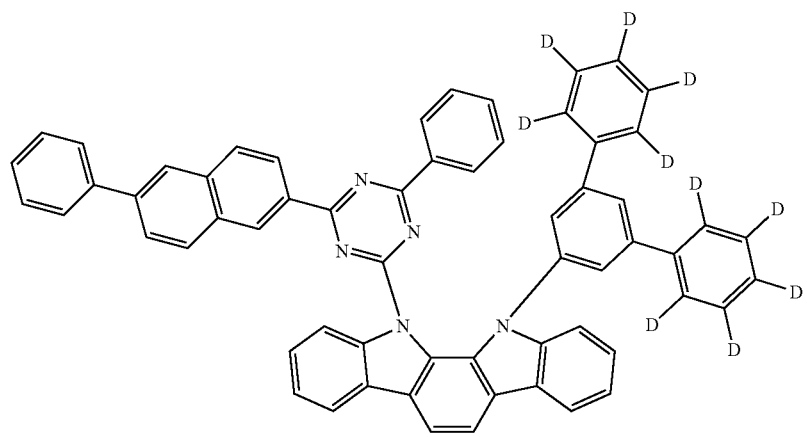
49
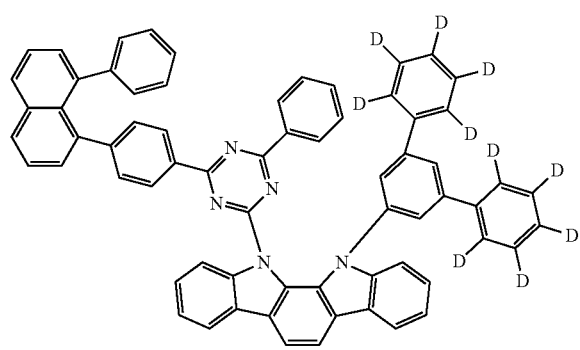
50
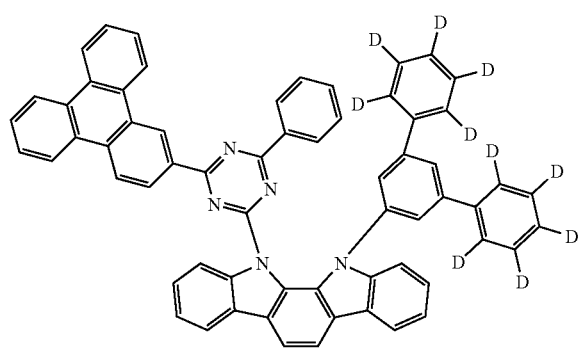

51
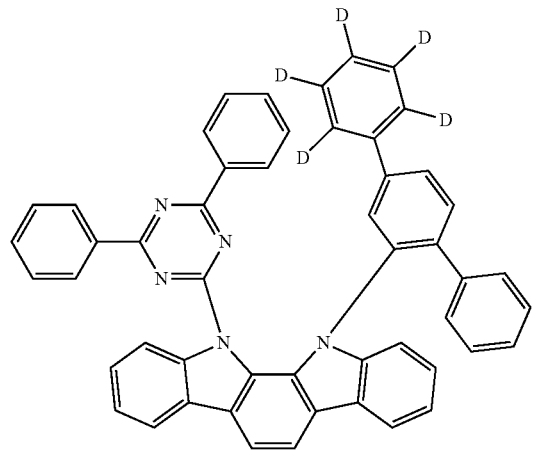
52
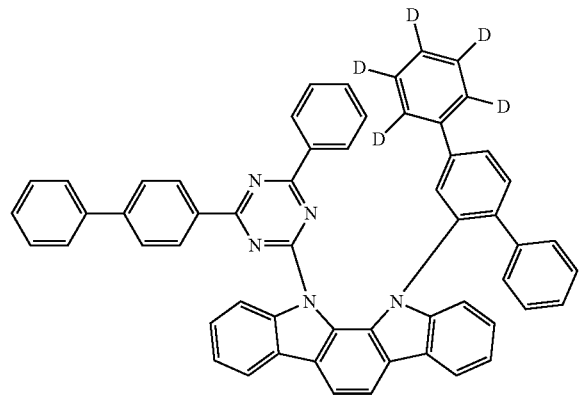
53
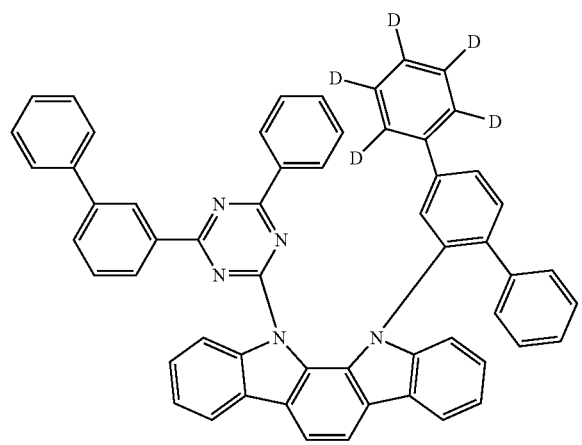
56
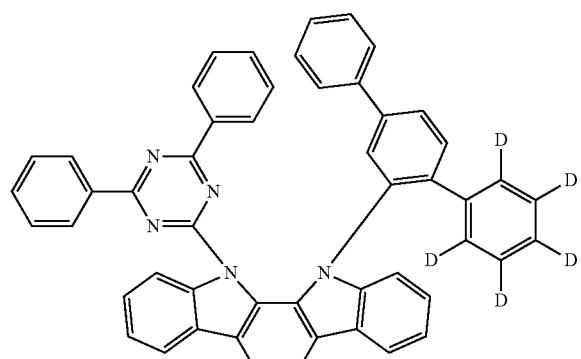
57
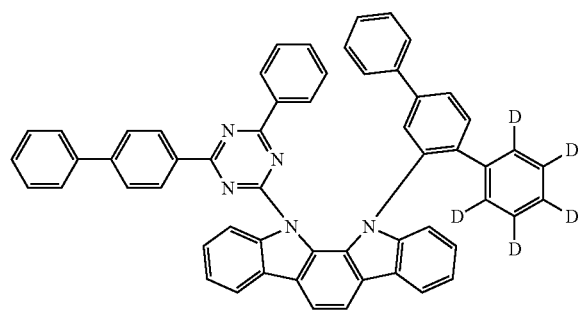
58
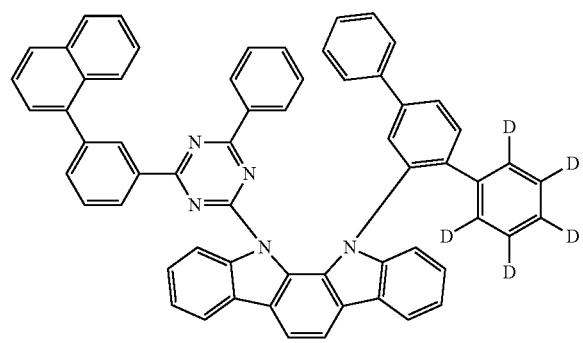

-continued
59
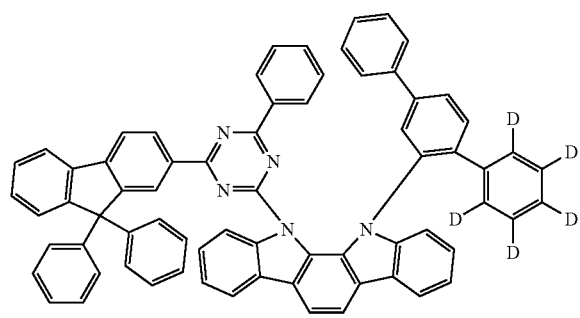
61
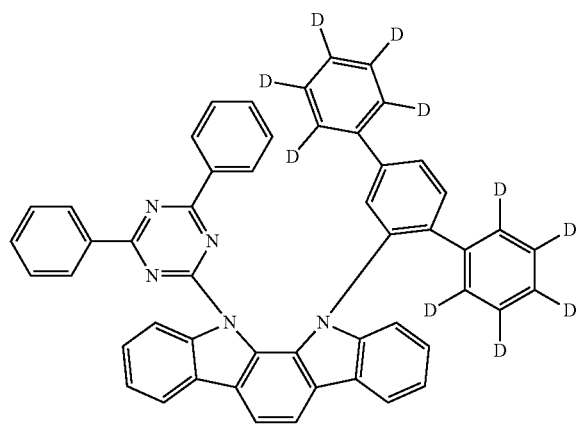
62
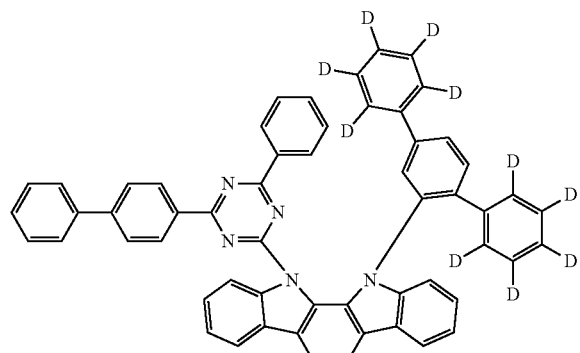
63
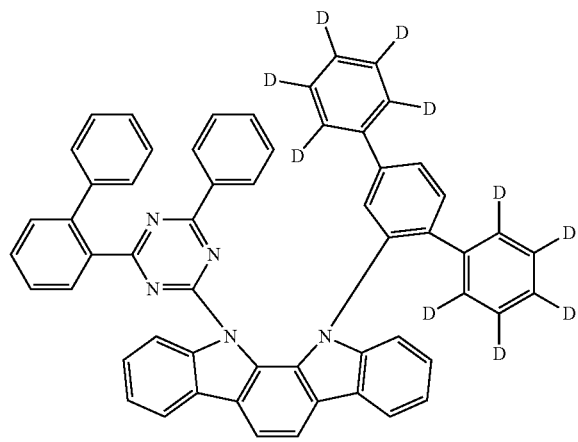
64
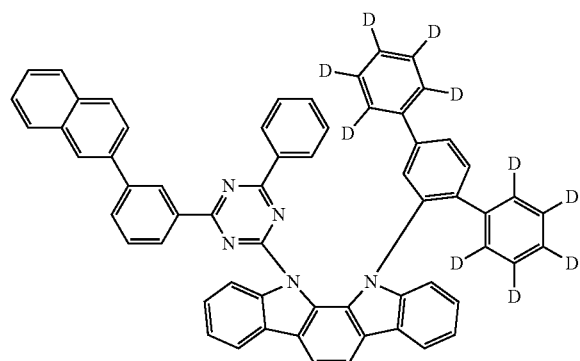
65
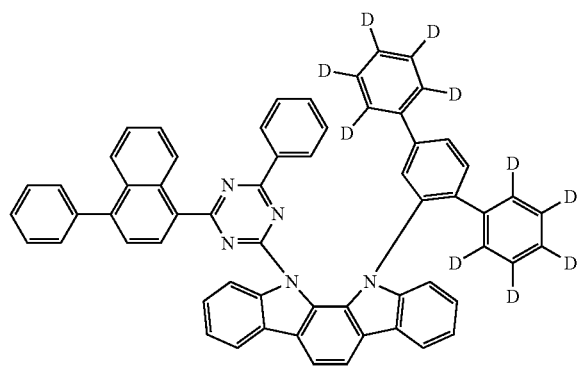

66
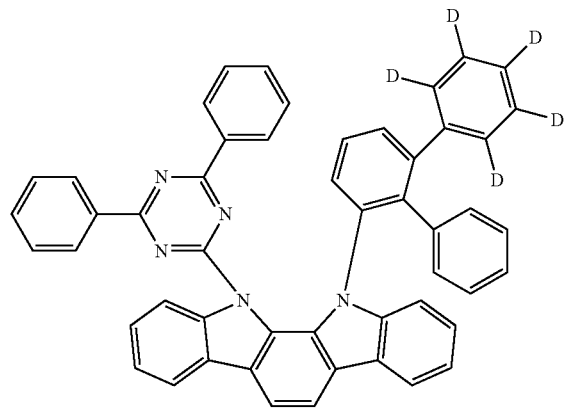
67
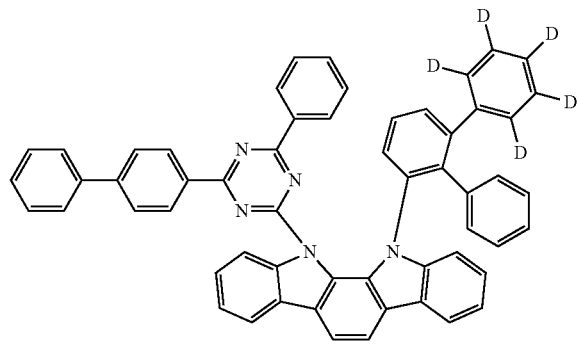
68
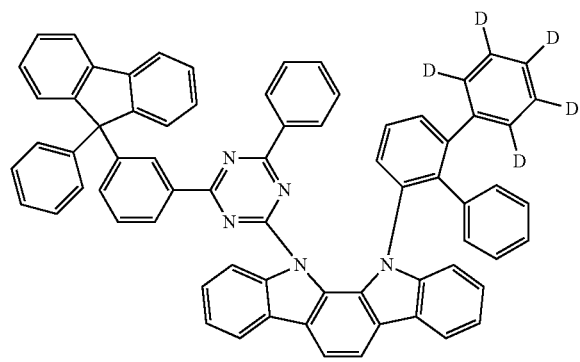
70
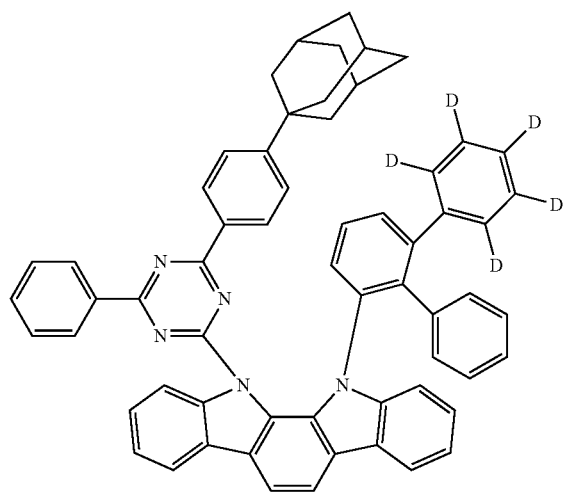
71
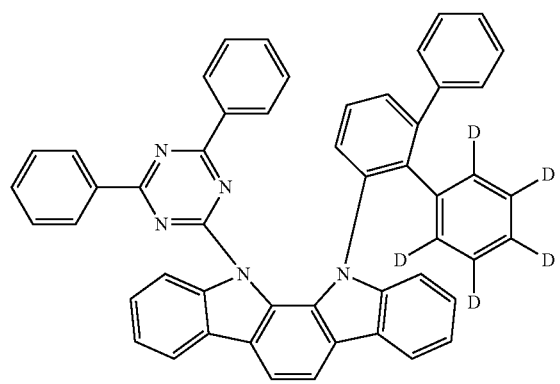
72
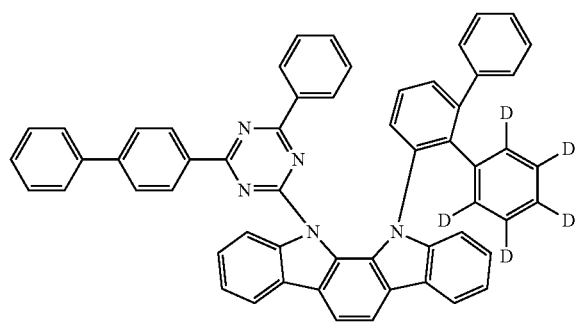

131 132
-continued
74
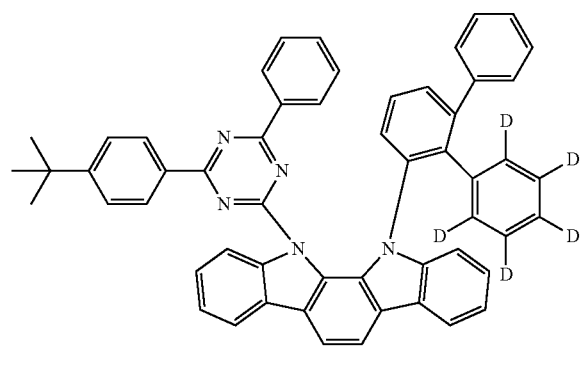
75
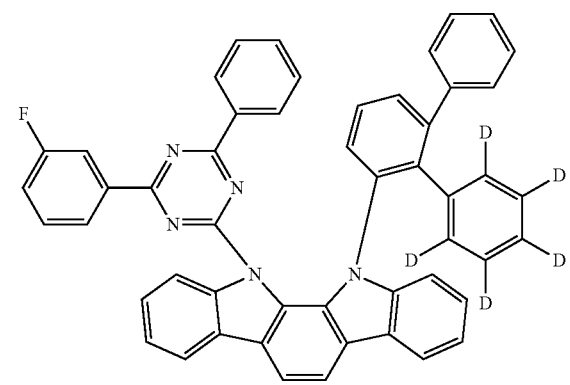
76
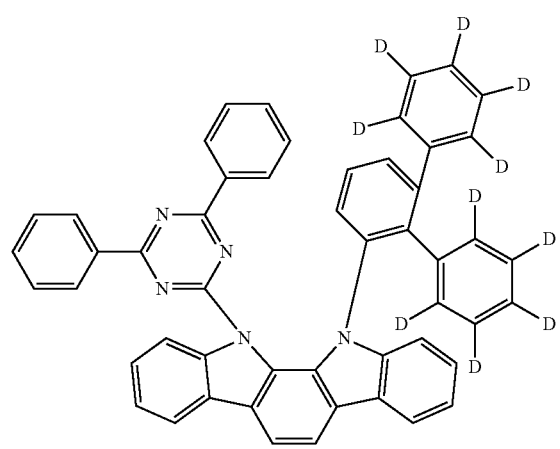
77
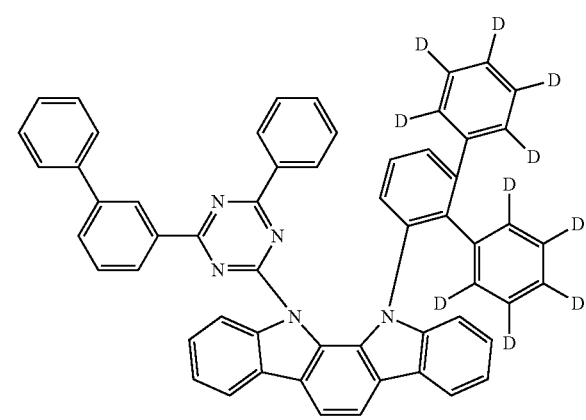
78
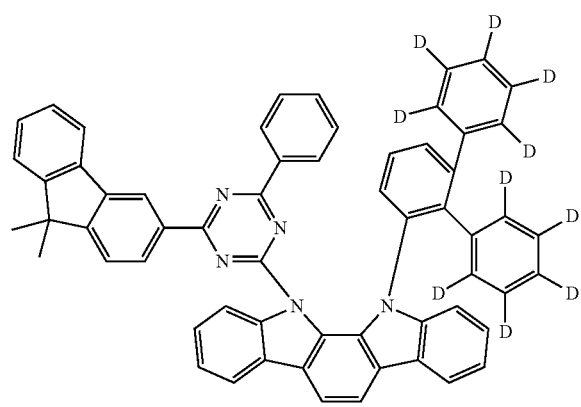
81
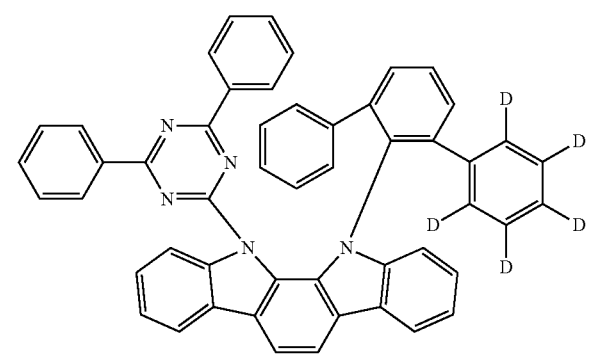

-continued
82
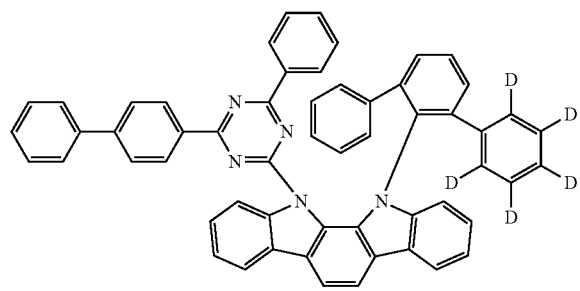
83
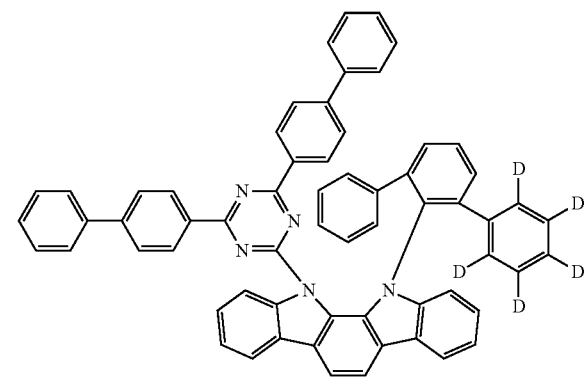
85
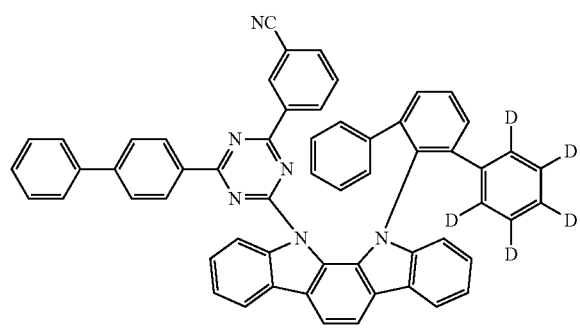
86
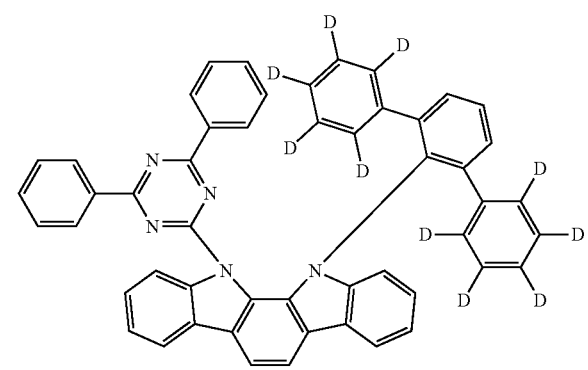
87
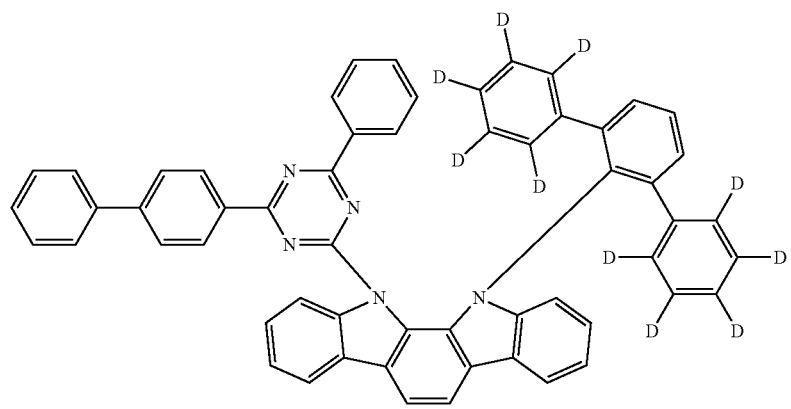
88
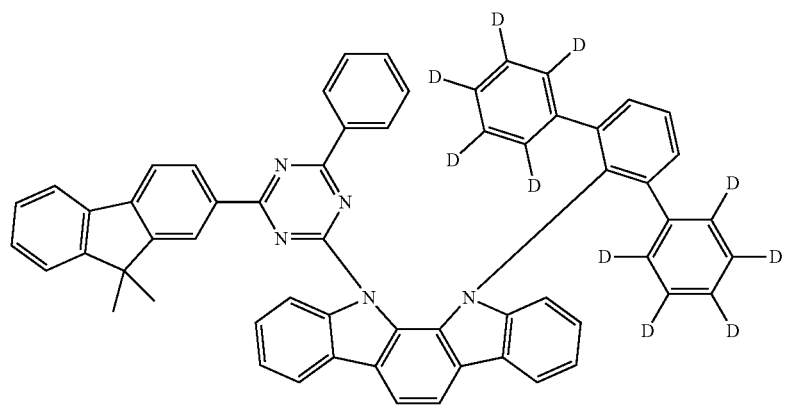

-continued

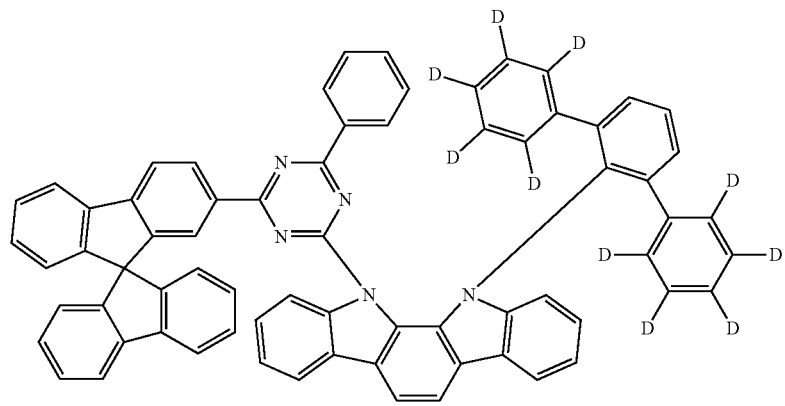

90

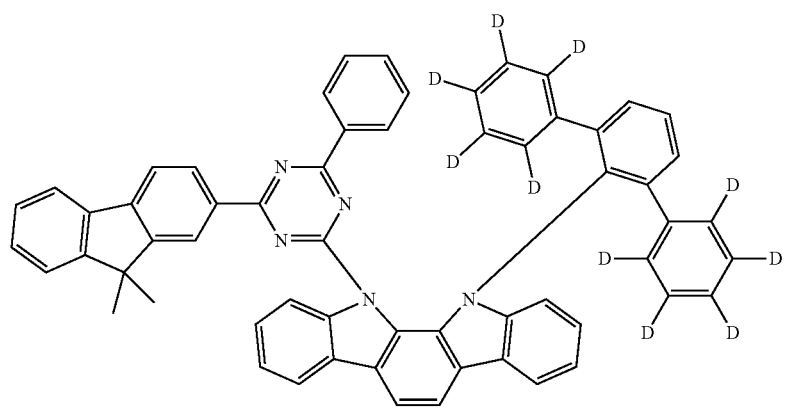

92

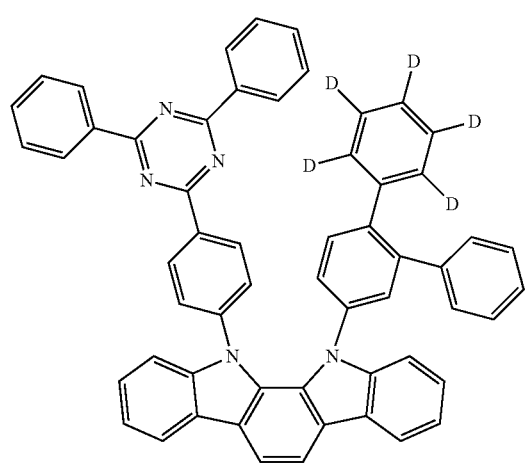

93

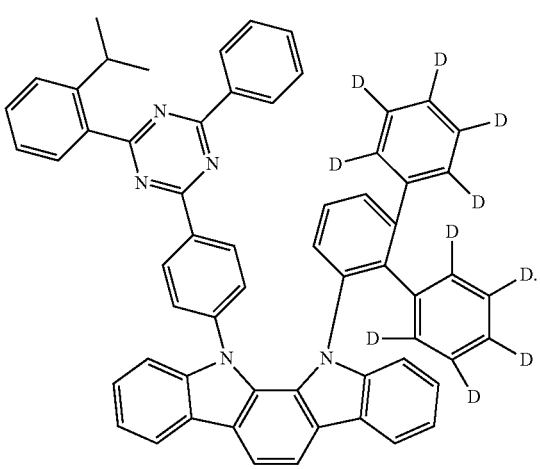

95

6. An organic electroluminescent device comprising an anode and a cathode which are oppositely disposed, and a functional layer disposed between the anode and the cathode; wherein the functional layer comprises an organic luminescent layer comprising the nitrogen-containing compound according to claim 1.

7. An electronic device comprising the organic electroluminescent device according to claim 6.

* * * * *